(12) United States Patent
Babler et al.

(10) Patent No.: US 9,572,811 B2
(45) Date of Patent: Feb. 21, 2017

(54) TREATMENT OF DRY EYE

(71) Applicant: PRINCIPIA BIOPHARMA INC., South San Francisco, CA (US)

(72) Inventors: Martin Babler, San Francisco, CA (US); Mary E. Gerritsen, San Mateo, CA (US)

(73) Assignee: PRINCIPIA BIOPHARMA INC., South San Francisco, CA (US)

(*) Notice: Subject to any disclaimer, the term of this patent is extended or adjusted under 35 U.S.C. 154(b) by 0 days.

(21) Appl. No.: 14/418,484

(22) PCT Filed: Jul. 31, 2013

(86) PCT No.: PCT/US2013/053042
§ 371 (c)(1),
(2) Date: May 20, 2015

(87) PCT Pub. No.: WO2014/022569
PCT Pub. Date: Feb. 6, 2014

(65) Prior Publication Data
US 2015/0182530 A1 Jul. 2, 2015

Related U.S. Application Data

(60) Provisional application No. 61/679,428, filed on Aug. 3, 2012.

(51) Int. Cl.
*A61K 31/519* (2006.01)
*A61K 31/5377* (2006.01)

(52) U.S. Cl.
CPC ......... *A61K 31/519* (2013.01); *A61K 31/5377* (2013.01)

(58) Field of Classification Search
None
See application file for complete search history.

(56) References Cited

FOREIGN PATENT DOCUMENTS

| WO | WO 2008/039218 A2 | 4/2008 |
|---|---|---|
| WO | WO 2009/140128 A2 | 11/2009 |
| WO | WO 2011/031896 A2 | 3/2011 |
| WO | WO 2013/010380 A1 | 1/2013 |
| WO | WO 2013/041605 A1 | 3/2013 |

OTHER PUBLICATIONS

Abdulahad et al., "Immune regulation and B-cell depletion therapy in patients with primary Sjögren's syndrome," *Journal of Autoimmunity*, 39(1): 103-111 (2012).
Lou et al., "Bruton's Tyrosine Kinase Inhibitors: Approaches to Potent and Selective Inhibition, Preclinical and Clinical Evaluation for Inflammatory Diseases and B Cell Malignancies," *J. Med. Chem.*, 55(10): 4539-4550 (2012).
Nakamura et al., "Diquafosol Ophthalmic Solution for Dry Eye Treatment," *Advances in Therapy*, 29(7): 579-589 (2012).
PCT Notification of Transmittal of the International Search Report and the Written Opinion of the International Searching Authority, or the Declaration in International Application No. PCT/US2013/053042, mailed Nov. 18, 2013 (13 pages).
2012 ICD-9-CM Diagnosis Code 372.30: Conjunctivitis, unspecified, retrieved Aug. 4, 2016 (1 page).
Johnson et al., "Coding for Dry Eye," *Optometric Management*, Issue: Mar. 2004 (7 pages).
Dry Eye vs. Conjunctivitis | WhatisDryEye.com, retrieved Aug. 4, 2016 (5 pages).

*Primary Examiner* — Samantha Shterengarts
(74) *Attorney, Agent, or Firm* — Finnegan, Henderson, Farabow, Garrett & Dunner LLP

(57) ABSTRACT

The present disclosure provides a method of treating dry eye by inhibition of Bruton's tyrosine kinase (hereinafter "BTK") inhibitors, pharmaceutical formulations comprising the same, and processes for preparing such compounds.

9 Claims, No Drawings

TREATMENT OF DRY EYE

This application is a national phase of international application number PCT/US2013/053042, filed Jul. 31, 2013 and claims the benefit of provisional application No. 61/679,428, filed Aug. 3, 2012, the content of which is incorporated herein by reference.

The present disclosure provides a method of treating dry eye by inhibition of Bruton's tyrosine kinase (hereinafter "BTK") inhibitors, pharmaceutical formulations comprising the same, and processes for preparing such compounds.

Dry eye disease ("DED") is a common, multifactorial syndrome characterized by ocular discomfort, visual disturbance, and tear film instability, and is associated with damage to the corneal and conjunctival surfaces. It affects approximately 13-20% of the adult population in the US. Common symptoms include foreign body sensation, itching, photophobia, and discomfort. It is accompanied by increased osmolarity of the tear film, and ocular surface inflammation.

Increasing evidence now indicates that chronic inflammation and autoimmunity play important roles in the pathogenesis and symptoms of DED. It is thought that ocular surface inflammation is sustained by the ongoing activation and infiltration of pathogenic immune cells. The influx of CD4+ T cells in the conjunctiva and infiltration of CD11b+ monocytic cells in the cornea have been documented by several groups (see De Paiva, C. S., et. al., Mucosal Immunol, 2: 243-253, 2009; Pflugfelder, S. C., et. al., Cornea, 27 Suppl 1: S9-11, 2008; and Barabino, S. and Dana, M. R. Chem Immunol Allergy, 92: 176-184, 2007). The dessication of the the ocular surface creates a stress response that results in the secretion of inflammatory cytokines, such as IL-1, TNFα and IL-6, which in turn facilitate the activation and migration of resident antigen presenting cells (APC) toward the draining lymph nodes. Once in the lymph node the APCs present antigen to naïve T cells (Th0), leading to the expansion of IL-17 secreting Th17 cells and interferon-γ secreting Th1 cells. The effector cells can then migrate to the ocular surface and secrete effector cytokines. Ultimately the ocular surface becomes enriched in a milieu of cytokines, chemokines, and immune/inflammatory cells, creating an ongoing and self-sustaining process of inflammation (see Pflugfelder, S. C., et. al., Cornea, 27 Suppl 1: S9-11, 2008; Chauhan, S. K. and Dana, R. Mucosal Immunol, 2: 375-376, 2009; Calonge, M., et. al., Ocul Immunol Inflamm, 18: 244-253; and Stevenson, W., et. al., Arch Ophthalmol, 130: 90-100). Further evidence for an important role of inflammation/autoimmunity in DED is provided by both preclinical and clinical studies that have demonstrated the effectiveness of drugs that target specific receptors/mediators or signaling pathways. Cyclosporine A, a potent immunosuppressive drug which inhibits the calcineurin phosphatase pathway, responsible for the transcription of T-cell activating cytokines such as IL-2, is effective, and widely used, as a topical treatment for DED in man (see Stevenson, D., et. al., Ophthalmology, 107: 967-974, 2000; and Sall, K., et. al., Ophthalmology, 107: 631-639, 2000). However, cyclosporine has a slow onset of action (up to 24 weeks), can cause drug related ocular burning, and may even require induction treatment with topical steroids to reduce the persistent stinging (see Sheppard, J. et. al., J. Ocul. Pharmacol Ther, 27: 23-27). Glucocorticoids can be used acutely in cases of severe DED (see Cordero-Coma, M., et. al., Ocul Immunol Inflamm, 15: 99-104, 2007), although long term corticosteroid use is associated with unacceptable toxicity including ocular hypertension and cataracts. There is a significant unmet medical need for a second generation pharmacological agent for dry eye with a faster onset of application, reduced need for multiple daily applications of drug, an enhanced tolerability profile, and the ability to improve patient's quality of life.

The majority of the anti-inflammatory agents under evaluation for the treatment of DED either preclinically or clinically target T-cells as their principal cellular target. However, B cells are well recognized players in a number of autoimmune diseases, including systemic lupus erythematosus, rheumatoid arthritis, and Sjögren's syndrome. B cells have multi-faceted roles in autoimmune disease, functioning as antigen presenting cells, cytokine secreting cells, and as autoantibody secreting plasma cells (which can damage target tissues by recruiting inflammatory cells via Fcγ receptor signaling and/or by complement activation). Moreover, the successful application of B-cell targeted therapies (e.g. Rituximab, Epratuzumab) in treatment of autoimmune diseases has refocused attention on these cells as powerful regulators of autoimmunity. While the presence of B cells in tissues of DED patients or experimental models has not been extensively evaluated, B-cells are present in the follicles of draining lymph nodes. The presence of autoantibodies to the type 3 muscarinic acetylcholine receptor (M3R) in sera from patients with Sjögren's syndrome-mediated dry eye, as well as in animal models has been documented by several independent laboratories (see, Bacman, S., et. a., Invest. Ophthalmol. Vis. Sci., 42: 321-327, 2001; Yamamoto, H., et. al., Clin. Immunol. Immunopathol., 78: 245-255, 1996; Kovacs, L., et. al., Rheumatology (Oxford), 44: 1021-1025, 2005; Marczinovits, I., et. al., J. Autoimmun, 24: 47-54, 2005; Borda, E., et. al., Mol. Cell. Biochem, 163-164: 335-341, 1996; and Bacman, S., et. al., Clin. Exp. Immunol., 104: 454-459, 1996). Passive transfer of IgG from patients with Sjögren's syndrome or rodent anti-M3R antibodies are sufficient to induce exocrine dysfunction in recipient animals (see Nguyen, K. H., et. al., Arthritis Rheum, 43: 2297-2306, 2000 and Robinson, C. P., et al., Proc Natl Acad Sci USA, 95: 7538-7543, 1998). Additionally autoantibodies to kallikrein family proteins (specifically Klk1 and Klk3) have been identified in the sera of mice with experimental DED (see Takada, K., et. al., J. Biol. Chem, 280: 3982-3988, 2005). It has recently been demonstrated that passive transfer of autoantibody containing serum or purified IgG derived from mice with experimental DED was sufficient to induce complement-dependent inflammation and tissue damage within the lacrimal functional unit of T-cell deficient nude recipient mice, suggesting that dry-eye specific antibodies can contribute to the pathogenesis CD4+ T-cell mediated dry eye (see Stern, M. E., et. al., Invest. Ophthalmol. Vis. Sci., 53: 2062-2075). A case report describing the successful use of the B-cell depleting antibody Rituximab for the treatment of severe Sjögren's dry eye also suggests that B-cell directed therapies may have utility in the treatment of DED (see Zapata, L. F., et. al., Cornea, 26: 886-887, 2007).

Bruton's tyrosine kinase (Btk) is a nonreceptor tyrosine kinase that is a member of the Src-related Tec tyrosine kinase family. The development and function of normal B-cells is dependent on Btk, which is activated through the B-cell receptor (BCR) upon binding to antigens. In mice, mutations or deletions of Btk lead to disruption of Btk function, preventing B-cell maturation and secretion of immunoglobulins (see Kerner, J. D., et. al., Immunity, 3: 301-312, 1995; and Khan, W. N., et. al., Immunity, 3: 283-299, 1995). Mutations in the human Btk gene are the cause of XLA (X-linked agammaglobulinemia), a male immune deficiency disorder characterized by the lack of mature, Ig-producing peripheral B cells (see de Weers, M., et. al., *Hum Mol Genet*, 3: 161-166, 1994; and Vihinen, M., et. al., *Proc Natl Acad Sci* USA, 91: 12803-12807, 1994). Btk has also been implicated in signaling pathways associated with several cytokine receptors (see Moon, B. G., et. al., *Immunology*, 102: 289-300, 2001; Sato, S., et. al., *J. Exp. Med.*, 180: 2101-2111, 1994; and Matsuda, T., et. al., *Blood*, 85: 627-633, 1995) and also in heterotrimeric G-protein coupled receptor signaling (see Qiu, Y. and Kung, H. J. *Oncogene*, 19: 5651-5661, 2000). In addition to its role in B-cells, Btk may also play important roles in inflammation associated neutrophil, monocyte/macrophage and dendritic cells responses (see Koprulu, A. D. and Ellmeier, W. *Crit. Rev. Immunol.*, 29: 317-333, 2009). For example, Btk-deficient mononuclear cells from XLA patients have impaired TNFα production, and overexpression of Btk in these cells results in enhanced TNFα production (see Horwood, N. J., et. al., *J. Exp. Med.*, 197: 1603-1611, 2003 and Sochorova, K., et. al., *Blood*, 109: 2553-2556, 2007). Btk also plays a role in the LPS stimulated (through activation of the TLR4 receptor) induction of NF-κB dependent genes (see Jefferies, C. A., et. al., *J. Biol. Chem.*, 278: 26258-26264, 2003; Wong, W. S. and Leong, K. P. *Biochim. Biophys. Acta*, 1697: 53-69, 2004 Wong, and Schmidt, N. W., et. al., *J. Immunol.*, 177: 7203-7210, 2006). In monocyte/macrophages, Btk has an important role in TLR2 induced cytokine production, and in TLR8 and TLR9 signaling (see Doyle, S. L., et. al., *J. Biol. Chem*, 282: 36953-36960, 2007). Btk is also important in the signal transduction events mediated by high-affinity IgE receptors (FcεRI) in mast cells (see Ellmeier, W., et. al., *Febs J.*, 278: 1990-2000; Hata, D., et. al., *J. Exp. Med.*, 187: 1235-1247, 1998; and Setoguchi, R., et. al., *Immunol. Lett.*, 64: 109-118, 1998). These observations suggest that inhibition of Btk activity would have potential therapeutic value in the treatment of inflammatory and allergic diseases. Indeed, antagonism of Btk has been shown to have potent inhibitory activity in a number of animal models of disease, including collagen induced arthritis (mouse and rat), collagen induced antibody induced arthritis, adjuvant induced arthritis, lupus (MLR-fas/lpr mouse) reverse passive anaphylactic reaction, cutaneous anaphylaxis as well as T-cell independent NP-Ficoll induced inflammation (see Xu, D., Kim, Y., et. al., *J. Pharmacol. Exp. Ther.*, 341: 90-103; Chang, B. Y., et. al., *Arthritis Res. Ther*, 13: R115; Di Paolo, J. A., et. al., *Nat Chem Biol*, 7: 41-50; Kyttaris, V. C. and Tsokos, G. C. *Curr Opin Rheumatol*, 23: 449-453; and Honigberg, L. A., et. al., *Proc. Natl. Acad. Sci.* USA, 107: 13075-13080).

It is well recognized that drug delivery to ocular tissues is a problem, with the majority of administered drug rapidly eliminated by the lacrimal fluid. The cornea itself is a major permeabiltiy barrier, and as a consequence only a small proportion of drug (<5%) administered topically to the eye reaches ocular tissues. Therefore a compound that inhibits BTK by forming a reversible or irreversible covalent bond with BTK thereby providing a long duration of action provides an entirely novel approach to ocular inflammatory disorders, including dry eye disease.

Accordingly, in one aspect, provided is a method of treating dry eye disease in a patient in need of such treatment comprising topically administering to the eye of said patient a BTK inhibitor. In one embodiment, a therapeutically effective amount of the BTK inhibitor is topically administered to the eye of the patient. In another embodiment, the BTK inhibitor is a reversible or irreversible covalent inhibitor wherein said reversible or irreversible covalent inhibitor forms a reversible or an irreversible covalent bond, respectively, with Cys 481 of BTK. In one embodiment of above aspect, the dry eye disease is associated with Sjogren's syndrome. In another embodiment of above aspect, the dry eye disease is not associated with Sjogren's syndrome. In one embodiment of the above aspects, the BTK inhibitor is a compound of Formula (I):

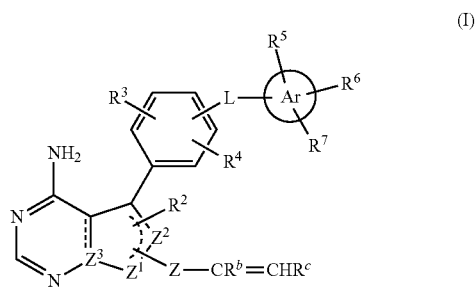

wherein:
dashed lines are an optional bond;
$Z^1$, $Z^2$, and $Z^3$ are —N— or —CH—, provided that one or two of $Z^1$, $Z^2$, and $Z^3$ are simultaneously —N—;
L is O, NR, or NR'CONR where each R and R' is independently hydrogen or alkyl;
Ar is aryl, heteroaryl, cycloalkyl or heterocyclyl;
$R^2$ is hydrogen, alkyl, hydroxy, alkoxy, cyano, halo or haloalkyl;
$R^3$ and $R^4$ are independently hydrogen, alkyl, cyclopropyl, hydroxy, alkoxy, cyano, halo, haloalkyl or haloalkoxy;
$R^5$, $R^6$ and $R^7$ are independently hydrogen, alkyl, hydroxy, alkoxy, halo, haloalkyl, haloalkoxy, carboxy, alkoxycarbonyl, cyano, —CONH$_2$, amino, alkylamino, or dialkylamino;
Z is -alkyleneCO—, -alkyleneOCO—, -alkyleneSO$_2$—,

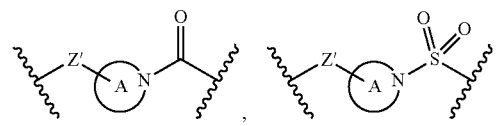

(where Z' is bond or alkylene, and ring A is heterocycloamino optionally substituted with one or two substituents independently selected from alkyl, hydroxy, or fluoro), -(alkylene)-NR$^a$CO— or -(alkylene)-NR$^a$SO$_2$— (where each R$^a$ is hydrogen, alkyl or cycloalkyl);
R$^b$ is hydrogen, cyano, nitro, halo, haloalkyl, haloalkoxy, alkylthio, or alkylsulfonyl;
R$^c$ is hydrogen, alkyl, haloalkoxy, substituted alkyl, cycloalkyl, cycloalkyleneNR$^d$R$^e$ (where R$^d$ and R$^e$ are independently hydrogen, alkyl, or cycloalkyl), or 3 to 6 membered saturated monocyclic heterocyclyl containing one or two heteroatoms selected from N, O, or S and optionally substituted with one or two substituents independently selected from hydroxy, alkyl or fluoro; or
a pharmaceutically acceptable salt thereof.

Without being bound to any specific mechanistic theory, in those embodiments wherein the compound of the present disclosure is a reversible covalent inhibitor, the inhibitor is substituted with an olefinic group such that the cysteine sulfhydryl group and a carbon atom of the carbon-carbon double bond (i.e. olefin) of the compound of the present disclosure can form a reversible, i.e., labile covalent bond.

For example, Cys 481 attacks an electron deficient carbon atom of the carbon-carbon double bond (olefin) in the compound of present disclosure to form a thiol adduct (e.g., Michael reaction with cysteine). In some embodiments, in the compound of Formula (I), Cys 481 of BTK can attack an electron deficient carbon atom of the carbon-carbon double bond in the —$CR^b$=$CHR^c$ group (where $R^b$ is not hydrogen) to form a labile, covalent bond thereby forming a thiol adduct.

In some embodiments, the electron deficient carbon atom of the olefin is distal to the carbon attached to the $R^b$ group, where $R^b$ is not hydrogen, and to the electron withdrawing Z moiety (see Formula I) in the compounds of the present disclosure. Therefore, the combination of the $R^b$ group ($R^b$ not hydrogen) and the "Z" moieties and the olefinic moiety to which they are bonded in the compounds of the present disclosure can increase the reactivity of the olefin to form a thiol adduct to Cys 481 in BTK to form a reversible covalent bond.

The reversible covalent inhibitors bind with BTK in two different manners. In addition to the labile covalent binding, discussed above, they also form non-covalent binding (e.g., via van der Waals binding, hydrogen binding, hydrophobic binding, hydrophilic binding, and/or electrostatic charge binding) with BTK, the non-covalent binding being sufficient to at least partially inhibit the kinase activity of the BTK.

Hence, the compounds of the present disclosure which are reversible covalent inhibitors have both a cysteine-mediated covalent binding and a non-covalent binding with the BTK. This is in contrast with non-covalent reversible inhibitors which inhibit the BTK only via non-covalent binding and lack the cysteine-mediated covalent binding.

The result of the binding of the reversible covalent compounds of the present disclosure with BTK in the two different manners is a reversible covalent inhibitor having a slow off-rate and a protracted duration of action, in some instances comparable to an irreversible covalent inhibitor (such as compound of Formula (I) where $R^b$ is hydrogen) without forming permanent irreversible protein adducts. The difference between irreversible and reversible covalent inhibitors can be ascertained utilizing assays disclosed herein.

In general, the binding involved in an inhibitor that forms a reversible covalent bond with BTK is stable when the BTK is in certain configurations and susceptible to being broken when the BTK is in different configurations (in both cases under physiologic conditions), whereas the interaction between an inhibitor that forms an irreversible covalent bond is stable under physiologic conditions even when the BTK is in different configurations.

A reversible covalent bond often imparts unique properties related to the residence time of the compound within the cysteine-containing binding site. In this context, residence time refers to the temporal duration of the compound-target complex under different conditions (see Copeland R A, Pompliano D L, Meek T D. Drug-target residence time and its implications for lead optimization. Nat. Rev. Drug Discov. 5(9), 730-739 (2006). The presence of a reversible covalent bond in a reversible covalent inhibitor disclosed herein can lead to an extended residence time when compared to a compound that does not form a covalent bond with BTK. In one embodiment disclosed herein the compounds of the present disclosure that are reversible covalent inhibitors have a residence time of at least about 1 h. Residence time may be measured using an occupancy assay in a biochemical or cellular environment (see Biological Example 5 below). Additionally, residence time may be measured using a functional assay following a defined wash-out period. Compounds that form an irreversible covalent bond in an irreversible covalent inhibitor share these extended residence time properties but may nonetheless be differentiated from reversible covalent inhibitor using a reversibility assay. The ability of the compound of the disclosure to form reversible or irreversible covalent bond with Cys481 of BTK (UniprotKB Sequence ID Q06187) and the olefinic bond in the compound of the disclosure, can be determined by the assays described in Biological Examples 3-6 below. In another embodiment of the above aspects, the BTK inhibitors are those disclosed on pages 4-6, 14-16, and specific compounds disclosed on pages 57-93, of PCT application publication no. WO 2009/158571, the disclosure of these pages is incorporated herein by reference in its entirety. The scope of the terms disclosed on pages 4-6 and 14-16 will be as defined on pages 6-14 of WO 2009/158571. In one embodiment, of this aspect, the compound is N-(3-((5-fluoro-2-((4-(2-methoxyethoxy)phenyl)amino)pyrimidin-4-yl)amino)phenyl)acrylamide or a pharmaceutically acceptable salt thereof.

DEFINITIONS

Unless otherwise stated, the following terms used in the specification and claims are defined for the purposes of this application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylthio" means a —SR radical where R is alkyl as defined above, e.g., methylthio, ethylthio, and the like.

"Alkylsulfonyl" means a —$SO_2R$ radical where R is alkyl as defined above, e.g., methylsulfonyl, ethylsulfonyl, and the like.

"Amino" means a —$NH_2$.

"Alkylamino" means a —NHR radical where R is alkyl as defined above, e.g., methylamino, ethylamino, propylamino, or 2-propylamino, and the like.

"Alkoxy" means a OR radical where R is alkyl as defined above, e.g., methoxy, ethoxy, propoxy, or 2-propoxy, n-, iso-, or Cert-butoxy, and the like.

"Alkoxyalkyl" means a linear monovalent hydrocarbon radical of one to six carbon atoms or a branched monovalent hydrocarbon radical of three to six carbons substituted with at least one alkoxy group, or one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Acyl" means a —COR radical where R is alkyl, haloalkyl, cycloalkyl, cycloalkylalkyl, aryl, aralkyl, heteroaryl, heteroaralkyl, heterocyclyl, or heterocyclylalkyl, each as defined herein, and wherein the aryl, heteroaryl, or heterocyclyl ring either alone or part of another group e.g., aralkyl, is optionally substituted with one, two, or three substituents independently selected from alkyl, hydroxy, alkoxy, halo, haloalkyl, haloalkoxy, carboxy, alkoxycarbonyl, alkylcarbonyl, cyano, —CONH$_2$, alkylaminocarbonyl, dialkylaminocarbonyl, substituted alkylaminocarbonyl, e.g., acetyl, propionyl, benzoyl, pyridinylcarbonyl, and the like. When R is alkyl, the radical is also referred to herein as alkylcarbonyl.

"Aryl" means a monovalent monocyclic or bicyclic aromatic hydrocarbon radical of 6 to 10 ring atoms e.g., phenyl or naphthyl.

"Cycloalkyl" means a cyclic saturated monovalent hydrocarbon radical of three to ten carbon atoms wherein one or two carbon atoms may be replaced by an oxo group, e.g., cyclopropyl, cyclobutyl, cyclopentyl, or cyclohexyl, and the like.

"Cycloalkylene" means a cyclic saturated divalent hydrocarbon radical of three to ten carbon atoms wherein one or two carbon atoms may be replaced by an oxo group, e.g., cyclopropylene, cyclobutylene, cyclopentylene, or cyclohexylene, and the like.

"Carboxy" means —COOH.

"Dialkylamino" means a —NRR' radical where R and R' are independently alkyl.

"Halo" means fluoro, chloro, bromo, or iodo. In one embodiment halo is fluoro or chloro.

"Haloalkyl" means alkyl radical as defined above, which is substituted with one or more halogen atoms or one to five halogen atoms (in one embodiment fluorine or chlorine), including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it is referred to in this application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl. In one embodiment, 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Heterocycloamino" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C provided that at least one of the ring atoms is N. Additionally, one or two ring carbon atoms in the heterocycloamino ring can optionally be replaced by a —CO— group. When the heterocycloamino ring is unsaturated it can contain one or two ring double bonds provided that the ring is not aromatic.

"Heteroaryl" means a monovalent monocyclic or bicyclic aromatic radical of 5 to 10 ring atoms where one or more, or one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

The present disclosure also includes the prodrugs of compounds of Formula (I) (or any of the embodiments thereof described herein). The term prodrug is intended to represent covalently bonded carriers, which are capable of releasing the active ingredient of Formula (I) (or any of the embodiments thereof described herein), when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) (or any of the embodiments thereof described herein), include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I) amides (e.g., trifluoroacetylamino, acetylamino, and the like), and the like. Prodrugs of compounds of Formula (I) (or any of the embodiments thereof described herein), are also within the scope of this disclosure.

The present disclosure also includes protected derivatives of compounds of Formula (I) (or any of the embodiments thereof described herein). For example, when compounds of Formula (I) (or any of the embodiments thereof described herein), contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (I) (or any of the embodiments thereof described herein), can be prepared by methods well known in the art.

The present disclosure also includes polymorphic forms (amorphous as well as crystalline) and deuterated forms of compounds of Formula (I) (or any of the embodiments thereof described herein).

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

The compounds of the present disclosure may have stereogenic centers. Compounds of the present disclosure containing an asymmetrically substituted atom may be isolated in optically active or racemic forms. It is well known in the art how to prepare optically active forms, such as by resolution of materials. All chiral, diastereomeric, racemic forms are within the scope of this disclosure, unless the specific stereochemistry or isomeric form is specifically indicated.

Compounds of Formula (I) (or any of the embodiments thereof described herein), can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (I) (or any of the embodiments thereof described herein), are within the scope of this disclosure.

"Oxo" or "carbonyl" means C=O group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Substituted alkyl" means alkyl group as defined herein which is substituted with one, two, or three substituents independently selected from hydroxyl, alkoxy, carboxy, cyano, carboxy, alkoxycarbonyl, alkylthio, alkylsulfonyl, halo, —CONRR' or —NRR' (where each R is hydrogen, alkyl, cycloalkyl, hydroxyalkyl, or alkoxyalkyl, and each R' is hydrogen, alkyl, or cycloalkyl) or heterocyclyl (in one embodiment heterocycloamino as defined herein) which is optionally substituted with one or two groups independently selected from alkyl, hydroxyl, alkoxy, alkylthio, alkylsulfonyl, halo, or —CONRR' where R and R' are as defined above.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of Formula (I) (or any of the embodiments thereof described herein), that, when administered to a mammal for treating a disease, is sufficient to effect such treatment for the disease. The "therapeutically effective amount" will vary depending on the compound, the disease and its severity and the age, weight, etc., of the mammal to be treated.

Embodiment A

In one embodiment, in the methods disclosed herein, the compound of Formula (I) as defined above (or a pharmaceutically acceptable salt thereof) is where the fused bicyclic moiety thereof has the structure:

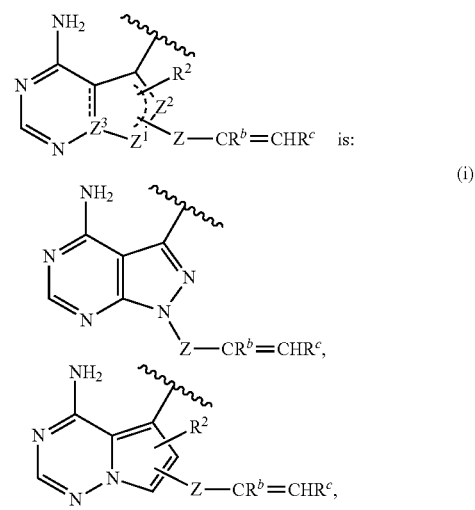

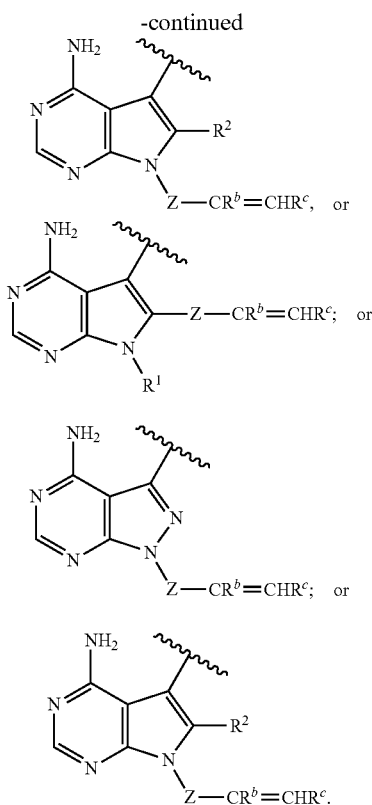

is a ring of formula:

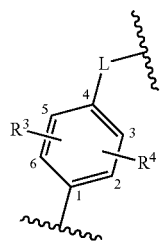

where $R^3$ is methyl, ethyl, chloro or fluoro. Within this embodiment and groups contained therein, in another group of compounds,

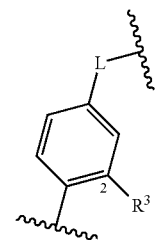

is a ring of formula:

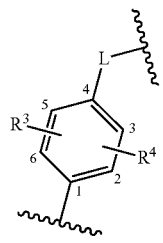

where $R^3$ is hydrogen or fluoro.

Embodiment B

In another embodiment, in the methods disclosed herein, in the compound of Formula (I) as defined above (or a pharmaceutically acceptable salt thereof) or as more specifically defined in embodiment (A) and groups contained therein, L is O. Within this embodiment, in another group of compounds L is NHCONH. Within this embodiment and groups contained therein, in one group of compounds $R^2$ is hydrogen, methyl, fluoro, or trifluoromethyl. Within this embodiment and groups contained therein, in another group of compounds $R^2$ is hydrogen or methyl. Within this embodiment and groups contained therein, in another group of compounds $R^2$ is hydrogen.

Embodiment C

In another embodiment, in the methods disclosed herein, the compound of Formula (I) as defined above (or a pharmaceutically acceptable salt thereof)) or as more specifically defined in embodiments (A) and/or (B) and groups contained therein, is one where $R^3$ and $R^4$ are independently hydrogen, alkyl, alkoxy, cyano, halo, haloalkyl or haloalkoxy. Within the groups in embodiment (C), in one group of compounds $R^3$ and $R^4$ are independently hydrogen, methyl, fluoro, methoxy, chloro, trifluoromethyl, or trifluoromethoxy. Within the groups in embodiment (C), in another group of compounds $R^3$ and $R^4$ are independently hydrogen or fluoro. Within this embodiment and groups contained therein, in another group of compounds,

Embodiment D

In another embodiment, in the methods disclosed herein, the compound of Formula (I) as defined above (or a pharmaceutically acceptable salt thereof) or as more specifically defined in embodiments (A), (B) and/or (C) and groups contained therein, is one where $R^5$, $R^6$ and $R^7$ are independently hydrogen, alkyl, alkoxy, halo, haloalkyl, haloalkoxy, or cyano.

Within the groups in this embodiment, in another group of compounds $R^6$ and $R^7$ are independently hydrogen, methyl, methoxy, fluoro, chloro, trifluoromethyl, trifluoromethoxy, or cyano.

Embodiment E

In another embodiment, in the methods disclosed herein, the compound of Formula (I) as defined above (or a pharmaceutically acceptable salt thereof) is or as more specifically defined in embodiments (A), (B), (C) and/or (D) and groups contained therein, is one where:

$R^b$ is CN;

Z is

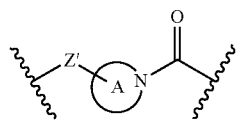

where Z' is bond or alkylene and $R^c$ is alkyl, substituted alkyl, cycloalkyl, cycloalkyleneNR$^d$R$^e$ (where R$^d$ and R$^e$ are independently hydrogen, alkyl, or cycloalkyl) or a 3 to 6 membered saturated monocyclic heterocyclyl containing one or two heteroatoms selected from N, O, or S and optionally substituted with one or two substituents independently selected from hydroxy, alkyl or fluoro.

(i). Within groups in embodiment (E), in one group of compounds, Z is

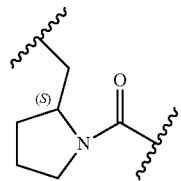

optionally substituted with one or two substituents independently selected from alkyl, hydroxy, or halo. Within (i), in one group of compounds Z is

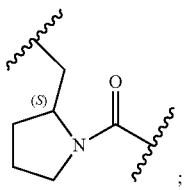

and $R^c$ is alkyl, cycloalkyl, cycloalkyleneNR$^d$R$^e$ (where R$^d$ and R$^e$ are independently hydrogen or alkyl), alkyl substituted with hydroxy, alkoxy, —NRR' (where R is alkyl, cycloalkyl, hydroxyalkyl, or alkoxyalkyl and R' is alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents independently selected from hydroxy, alkyl or fluoro. In one group of compounds, $R^c$ is isopropyl, tert-butyl, —C(CH$_3$)$_2$OCH$_2$CH$_3$, —C(CH$_3$)$_2$N(CH$_3$)$_2$, —C(CH$_3$)$_2$morpholine-4-yl, cyclopropyl, 2-pyrrolidinyl, 3- or 4-piperidinyl, 1-methylpiperidin-4-yl, 1-methylpiperidin-3-yl, or 4-tetrahydropyranyl; or $R^c$ is —C(CH$_3$)$_2$morpholine-4-yl, 2-pyrrolidinyl, 3- or 4-piperidinyl, 1-methylpiperidin-4-yl, 1-methylpiperidin-3-yl, or 4-tetrahydropyranyl.

(ii). Within groups in embodiment (E), in another group of compounds Z is

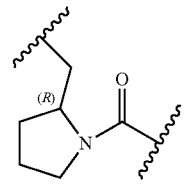

optionally substituted with one or two substituents independently selected from alkyl, hydroxy, or halo. Within (ii), in one group of compounds, Z is

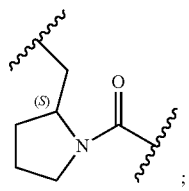

and $R^c$ is alkyl substituted with —NRR' (where each R is hydrogen, alkyl, cycloalkyl, hydroxyalkyl, or alkoxyalkyl and R' is hydrogen) or heterocycloamino which is attached to alkyl via nitrogen ring atom and which is optionally substituted with one or two groups independently selected from alkyl or hydroxyl. In one group of compounds, $R^c$ is —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, or —C(CH$_3$)$_2$morpholine-4-yl.

(iii). Within groups in embodiment (E) above, in one group of compounds Z is

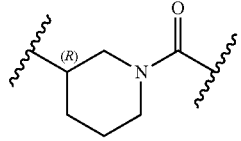

which is optionally substituted with one or two substituents independently selected from alkyl, hydroxy, or halo. Within (iii), in one group of Z is

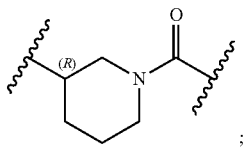

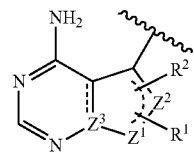

$R^c$ is alkyl, cycloalkyl, cycloalkyleneNR$^d$R$^e$ (where R$^d$ and R$^e$ are independently hydrogen or alkyl), alkyl substituted with hydroxy, alkoxy, —NRR' (where each R is alkyl, cycloalkyl, hydroxyalkyl, or alkoxyalkyl and R' is hydrogen or alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro. In one group of compounds, $R^c$ is isopropyl, tert-butyl, —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, —C(CH$_3$)$_2$OCH$_2$CH$_3$, —C(CH$_3$)$_2$N(CH$_3$)$_2$, —C(CH$_3$)$_2$morpholine-4-yl, cyclopropyl, 2-pyrrolidinyl, 3- or 4-piperidinyl, 1-methylpiperidin-4-yl, 1-methylpiperidin-3-yl, or 4-tetrahydropyranyl. In another group of compounds, $R^c$ is isopropyl, tert-butyl, or —C(CH$_3$)$_2$morpholine-4-yl.

Embodiment F

In another embodiment, in the methods disclosed herein, the compound of Formula (I) as defined above (or a pharmaceutically acceptable salt thereof) is or as more specifically defined in embodiments (A), (B), (C) and/or (D) and groups contained therein, is one where:

$R^b$ and $R^c$ are hydrogen; and Z is

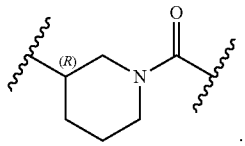

Embodiment G

In another embodiment, in the methods disclosed herein, the compound of Formula (I) as defined above (or a pharmaceutically acceptable salt thereof)) or as more specifically defined in embodiments (A), (B), (C), (D), (E) and/or (F), and groups contained therein, in one group of compounds the

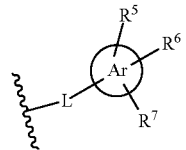

group is attached at the 4-position of the phenyl ring, the carbon atom of the phenyl ring attached to being carbon 1.

(i) Within the groups in embodiment F, in one group of compounds,

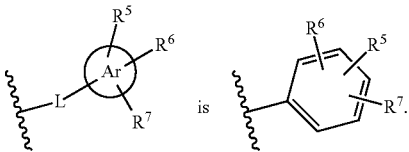

is

In one group of compounds

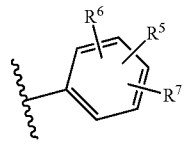

is a ring of formula:

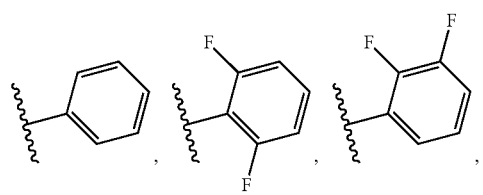

(i)

or (ii) phenyl or

Embodiment H

In yet another embodiment, in the methods disclosed herein, the compound of Formula (I) is chosen from:

2-(3-(4-amino-3-(4-phenoxyphenyl)-1H-pyrazolo[3,4-d]pyrimidin-1-yl)piperidine-1-carbonyl)-3-cyclopropylacrylonitrile; 1

2-(2-((4-amino-3-(4-phenoxyphenyl)-1H-pyrazolo[3,4-d]pyrimidin-1-yl)methyl)pyrrolidine-1-carbonyl)-3-cyclopropylacrylonitrile; 2

2-(4-(4-amino-3-(4-phenoxyphenyl)-1H-pyrazolo[3,4-d]pyrimidin-1-yl)piperidine-1-carbonyl)-3-cyclopropylacrylonitrile; 3

2-(3-(4-amino-3-(4-(3,4-dichlorophenoxy)-3-methoxyphenyl)-1H-pyrazolo[3,4-d]pyrimidin-1-yl)piperidine-1-carbonyl)-3-cyclopropylacrylonitrile; 4

2-(2-((4-amino-3-(4-(3,4-dichlorophenoxy(3-methoxyphenyl)-1H-pyrazolo[3,4-d]pyrimidin-1-yl)methyl)pyrrolidine-1-carbonyl)-3-cyclopropylacrylonitrile; 5

2-(4-(4-amino-3-(4-(3,4-dichlorophenoxy)-3-methoxyphenyl)-1H-pyrazolo[3,4-d]pyrimidin-1-yl)piperidine-1-carbonyl)-3-cyclopropylacrylonitrile; 6

2-(3-(4-amino-3-(4-phenoxyphenyl)-1H-pyrazolo[3,4-d]pyrimidin-1-yl)piperidine-1-carbonyl)-4,4-dimethylpent-2-enenitrile; 7

2-(4-(4-amino-3-(4-phenoxyphenyl)-1H-pyrazolo[3,4-d]pyrimidin-1-yl)piperidine-1-carbonyl)-4,4-dimethylpent-2-enenitrile; 8

2-(4-(4-amino-3-(4-(3,4-dichlorophenoxy)-3-methoxyphenyl)-1H-pyrazolo[3,4-d]pyrimidin-1-yl)piperidine-1-carbonyl)-4,4-dimethylpent-2-enenitrile; 9

2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile; 10

N-((1s,4s)-4-(4-amino-3-(4-phenoxyphenyl)-1H-pyrazolo[3,4-d]pyrimidin-1-yl)cyclohexyl)-2-cyano-3-cyclopropylacrylamide; 11

2-(2-((4-amino-3-(4-(3,4-dichlorophenoxy)-3-methoxyphenyl)-1H-pyrazolo[3,4-d]pyrimidin-1-yl)methyl)pyrrolidine-1-carbonyl)-4,4-dimethylpent-2-enenitrile; 12

N-((1r,4r)-4-(4-amino-3-(4-(3,4-dichlorophenoxy)-3-methoxyphenyl)-1H-pyrazolo[3,4-d]pyrimidin-1-yl)cyclohexyl)-2-cyano-3-cyclopropylacrylamide; 13

N-((1s,4s)-4-(4-amino-3-(4-phenoxyphenyl)-1H-pyrazolo[3,4-d]pyrimidin-1-yl)cyclohexyl)-2-cyano-4,4-dimethylpent-2-enamide; 14

(R)-2-(3-(4-amino-3-(4-(3-fluorophenoxy)phenyl)-1H-pyrazolo[3,4-d]pyrimidin-1-yl)piperidine-1-carbonyl)-3-cyclopropylacrylamide; 15A (S)-2-(3-(4-amino-3-(4-(3-fluorophenoxy)phenyl)-1H-pyrazolo[3,4-d]pyrimidin-1-yl)piperidine-1-carbonyl)-3-cyclopropylacrylamide; 15B N-((1r,4r)-4-(4-amino-3-(4-(3,4-dichlorophenoxy)-3-methoxyphenyl)-1H-pyrazolo[3,4-d]pyrimidin-1-yl)cyclohexyl)-2-cyano-4,4-dimethylpent-2-enamide; 16

(R)-2-(3-(4-amino-3-(4-(3,5-difluorophenoxy)phenyl)-1H-pyrazolo[3,4-d]pyrimidin-1-yl)piperidine-1-carbonyl)-3-cyclopropylacrylamide; 17A (S)-2-(3-(4-amino-3-(4-(3,5-difluorophenoxy)phenyl)-1H-pyrazolo[3,4-d]pyrimidin-1-yl)piperidine-1-carbonyl)-3-cyclopropylacrylamide; 17B (R)-2-(3-(4-amino-3-(2-fluoro-4-(phenoxy)phenyl)-1H-pyrazolo[3,4-d]pyrimidin-1-yl)piperidine-1-carbonyl)-3-cyclopropylacrylamide; 18A (S)-2-(3-(4-amino-3-(2-fluoro-4-(phenoxy)phenyl)-1H-pyrazolo[3,4-d]pyrimidin-1-yl)piperidine-1-carbonyl)-3-cyclopropylacrylamide; 18B 2-(3-(4-amino-3-(4-(3,4-dichlorophenoxy)-3-methoxyphenyl)-1H-pyrazolo[3,4-d]pyrimidin-1-yl)piperidine-1-carbonyl)-4,4-dimethylpent-2-enenitrile; 19

N-((1s,4s)-4-(4-amino-3-(4-(3,4-dichlorophenoxy)-3-methoxyphenyl)-1H-pyrazolo[3,4-d]pyrimidin-1-yl)cyclohexyl)-2-cyano-3-cyclopropylacrylamide; 20

N-((1s,4s)-4-(4-amino-3-(4-(3,4-dichlorophenoxy)-3-methoxyphenyl)-1H-pyrazolo[3,4-d]pyrimidin-1-yl)cyclohexyl)-2-cyano-4,4-dimethylpent-2-enamide; 21

(R)-2-(2-((4-amino-3-(4-phenoxyphenyl)-1H-pyrazolo[3,4-d]pyrimidin-1-yl)methyl)pyrrolidine-1-carbonyl)-3-cyclopropylacrylonitrile; 22

(R)-2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile; 23A (S)-2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile; 23B (R)-2-(2-((4-amino-3-(4-(3-fluorophenoxy)phenyl)-1H-pyrazolo[3,4-d]pyrimidin-1-yl)methyl)pyrrolidine-1-carbonyl)-3-cyclopropylacrylonitrile; 24A (S)-2-(2-((4-amino-3-(4-(3-fluorophenoxy)phenyl)-1H-pyrazolo[3,4-d]pyrimidin-1-yl)methyl)pyrrolidine-1-carbonyl)-3-cyclopropylacrylonitrile; 24B (R)-2-(2-((4-amino-3-(4-(3,5-difluorophenoxy)phenyl)-1H-pyrazolo[3,4-d]pyrimidin-1-yl)methyl)pyrrolidine-1-carbonyl)-3-cyclopropylacrylonitrile; 25A (S)-2-(2-((4-amino-3-(4-(3,5-difluorophenoxy)phenyl)-1H-pyrazolo[3,4-d]pyrimidin-1-yl)methyl)pyrrolidine-1-carbonyl)-3-cyclopropylacrylonitrile; 25B (R)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile; 27A (S)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile; 27B 2-(3-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile; 28

(R)-2-(3-(4-amino-3-(4-phenoxyphenyl)-1H-pyrazolo[3,4-d]pyrimidin-1-yl)piperidine-1-carbonyl)-4,4-dimethylpent-2-enenitrile; 29A (S)-2-(3-(4-amino-3-(4-phenoxyphenyl)-1H-pyrazolo[3,4-d]pyrimidin-1-yl)piperidine-1-carbonyl)-4,4-dimethylpent-2-enenitrile; 29B (R)-2-(3-(4-amino-3-(4-phenoxyphenyl)-1H-pyrazolo[3,4-d]pyrimidin-1-yl)piperidine-1-carbonyl)-3-cyclopropylacrylamide; 30A (R)-2-(2-((4-amino-3-(4-(2,3-difluorophenoxy)phenyl)-1H-pyrazolo[3,4-d]pyrimidin-1-yl)methyl)pyrrolidine-1-carbonyl)-3-cyclopropylacrylonitrile; 31A (S)-2-(2-((4-amino-3-(4-(2,3-difluorophenoxy)phenyl)-1H-pyrazolo[3,4-d]pyrimidin-1-yl)methyl)pyrrolidine-1-carbonyl)-3-cyclopropylacrylonitrile; 31B (R)-2-(2-((4-amino-3-(4-(2,6-difluorophenoxy)phenyl)-1H-pyrazolo[3,4-d]pyrimidin-1-yl)methyl)pyrrolidine-1-carbonyl)-3-cyclopropylacrylonitrile; 32A (S)-2-(2-((4-amino-3-(4-(2,6-difluorophenoxy)phenyl)-1H-pyrazolo[3,4-d]pyrimidin-1-yl)methyl)pyrrolidine-1-carbonyl)-3-cyclopropylacrylonitrile; 32B (R)-2-(3-(4-amino-3-(4-(2-fluorophenoxy)phenyl)-1H-pyrazolo[3,4-d]pyrimidin-1-yl)piperidine-1-carbonyl)-3-cyclopropylacrylamide; 33A (S)-2-(3-(4-amino-3-(4-(2-fluorophenoxy)phenyl)-1H-pyrazolo[3,4-d]pyrimidin-1-yl)piperidine-1-carbonyl)-3-cyclopropylacrylamide; 33B N-(2-(4-amino-3-(4-phenoxyphenyl)-1H-pyrazolo[3,4-d]pyrimidin-1-yl)ethyl)-2-cyano-3-cyclopropylacrylamide; 34

(R)-2-(3-(4-amino-3-(4-(2,3-difluorophenoxy)phenyl)-1H-pyrazolo[3,4-d]pyrimidin-1-yl)piperidine-1-carbonyl)-3-cyclopropylacrylamide; 35A (S)-2-(3-(4-amino-3-(4-(2,3-difluorophenoxy)phenyl)-1H-pyrazolo[3,4-d]pyrimidin-1-yl)piperidine-1-carbonyl)-3-cyclopropylacrylamide; 35B (R)-2-(3-(4-amino-3-(4-(2,6-difluorophenoxy)phenyl)-1H-pyrazolo[3,4-d]pyrimidin-1-yl)piperidine-1-carbonyl)-3-cyclopropylacrylamide; 36A (S)-2-(3-(4-amino-3-(4-(2,6-difluorophenoxy)phenyl)-1H-pyrazolo[3,4-d]pyrimidin-1-yl)piperidine-1-carbonyl)-3-cyclopropylacrylamide; 36B (R)-2-(3-(4-amino-3-(4-(2,5-difluorophenoxy)phenyl)-1H-pyrazolo[3,4-d]pyrimidin-1-yl)piperidine-1-carbonyl)-3-cyclopropylacrylamide; 37A (S)-2-(3-(4-amino-3-(4-(2,5-difluorophenoxy)phenyl)-1H-pyrazolo[3,4-d]pyrimidin-1-yl)piperidine-1-carbonyl)-3-cyclopropylacrylamide; 37B (R)-2-(2-((4-amino-3-(4-(2-fluorophenoxy)phenyl)-1H-pyrazolo[3,4-d]pyrimidin-1-yl)methyl)pyrrolidine-1-carbonyl)-3-cyclopropylacrylonitrile; 38A (S)-2-(2-((4-amino-3-(4-(2-fluorophenoxy)phenyl)-1H-pyrazolo[3,4-d]pyrimidin-1-yl)methyl)pyrrolidine-1-carbonyl)-3-cyclopropylacrylonitrile; 38B (R)-2-(2-((4-amino-3-(4-(2,5-difluorophenoxy)phenyl)-1H-pyrazolo[3,4-d]pyrimidin-1-yl)methyl)pyrrolidine-1-carbonyl)-3-cyclopropylacrylonitrile; 39A (S)-2-(2-((4-amino-3-(4-(2,5-difluorophenoxy)phenyl)-1H-pyrazolo[3,4-d]pyrimidin-1-yl)methyl)pyrrolidine-1-carbonyl)-3-cyclopropylacrylonitrile; 39B (R)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-3-cyclopropylacrylonitrile; 40A (S)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-3-cyclopropylacrylonitrile; 40B (R)-2-(2-((4-amino-3-(2-fluoro-4-(3,5-difluorophenoxy)phenyl)-1H-pyrazolo[3,4-d]pyrimidin-1-yl)methyl)pyrrolidine-1-carbonyl)-3-cyclopropylacrylonitrile; 41A (S)-2-(2-((4-amino-3-(2-fluoro-4-(3,5-difluorophenoxy)phenyl)-1H-pyrazolo[3,4-d]pyrimidin-1-yl)methyl)pyrrolidine-1-carbonyl)-3-cyclopropylacrylonitrile; 41B (R)-2-(2-((4-amino-3-(3-fluoro-4-(phenoxy)phenyl)-1H-pyrazolo[3,4-d]pyrimidin-1-yl)methyl)pyrrolidine-1-carbonyl)-3-cyclopropylacrylonitrile; 42A (S)-2-(2-((4-amino-3-(3-fluoro-4-(phenoxy)phenyl)-1H-pyrazolo[3,4-d]pyrimidin-1-yl)methyl)pyrrolidine-1-carbonyl)-3-cyclopropylacrylonitrile; 42B (R)-2-(2-((4-amino-3-(2-fluoro-4-(2,3-difluorophenoxy)phenyl)-1H-pyrazolo[3,4-d]pyrimidin-1-yl)methyl)pyrrolidine-1-carbonyl)-3-cyclopropylacrylonitrile; 43A (S)-2-(2-((4-amino-3-(2-fluoro-4-(2,3-difluorophenoxy)phenyl)-1H-pyrazolo[3,4-d]pyrimidin-1-yl)methyl)pyrrolidine-1-carbonyl)-3-cyclopropylacrylonitrile; 43B (R)-2-(2-((4-amino-3-(2-fluoro-4-(2,6-difluorophenoxy)phenyl)-1H-pyrazolo[3,4-d]pyrimidin-1-yl)methyl)pyrrolidine-1-carbonyl)-3-cyclopropylacrylonitrile; 44A (S)-2-(2-((4-amino-3-(2-fluoro-4-(2,6-difluorophenoxy)phenyl)-1H-pyrazolo[3,4-d]pyrimidin-1-yl)methyl)pyrrolidine-1-carbonyl)-3-cyclopropylacrylonitrile; 44B N-(2-(4-amino-3-(2-fluoro-4-phenoxyphenyl)-1H-pyrazolo[3,4-d]pyrimidin-1-yl)ethyl)-2-cyano-3-cyclopropylacrylamide; 45

N-(2-(4-amino-3-(2-fluoro-4-phenoxyphenyl)-1H-pyrazolo[3,4-d]pyrimidin-1-yl)-2-methylpropyl)-2-cyano-3-cyclopropylacrylamide; 46

N-(1-(4-amino-3-(2-fluoro-4-phenoxyphenyl)-1H-pyrazolo[3,4-d]pyrimidin-1-yl)-2-methylpropan-2-yl)-2-cyano-3-cyclopropylacrylamide; 47

N-(2-(4-amino-3-(2-fluoro-4-phenoxyphenyl)-1H-pyrazolo[3,4-d]pyrimidin-1-yl)ethyl)-1-cyano-2-cyclopropylethenesulfonamide; 48

N-(2-(4-amino-3-(2-fluoro-4-phenoxyphenyl)-1H-pyrazolo[3,4-d]pyrimidin-1-yl)ethyl)-1-cyano-2-cyclopropyl-N-methylethenesulfonamide; 49

2-(4-amino-3-(2-fluoro-4-phenoxyphenyl)-1H-pyrazolo[3,4-d]pyrimidin-1-yl)ethyl 2-cyano-3-cyclopropylacrylate; 50

1-(4-amino-3-(2-fluoro-4-phenoxyphenyl)-1H-pyrazolo[3,4-d]pyrimidin-1-yl)-2-methylpropan-2-yl 2-cyano-3-cyclopropylacrylate; 51

2-((2-(4-amino-3-(2-fluoro-4-phenoxyphenyl)-1H-pyrazolo[3,4-d]pyrimidin-1-yl)ethyl)sulfonyl)-3-cyclopropylacrylonitrile; 52

2-(5-((4-amino-3-(2-fluoro-4-phenoxyphenyl)-1H-pyrazolo[3,4-d]pyrimidin-1-yl)methyl)oxazol-2-yl)-3-cyclopropylacrylonitrile; 53

(R)-2-(3-(4-amino-5-(4-phenoxyphenyl)-7H-pyrrolo[2,3-d]pyrimidin-7-yl)piperidine-1-carbonyl)-3-cyclopropylacrylonitrile; 54A (S)-2-(3-(4-amino-5-(4-phenoxyphenyl)-7H-pyrrolo[2,3-d]pyrimidin-7-yl)piperidine-1-carbonyl)-3-cyclopropylacrylonitrile; 54B (R)-2-(3-(4-amino-5-(4-(3,5-difluorophenoxy)phenyl)-7H-pyrrolo[2,3-d]pyrimidin-7-yl)piperidine-1-carbonyl)-3-cyclopropylacrylonitrile; 55A (S)-2-(3-(4-amino-5-(4-(3,5-difluorophenoxy)phenyl)-7H-pyrrolo[2,3-d]pyrimidin-7-yl)piperidine-1-carbonyl)-3-cyclopropylacrylonitrile; 55B (R)-2-(3-(4-amino-5-(2-fluoro-4-phenoxyphenyl)-7H-pyrrolo[2,3-d]pyrimidin-7-yl)piperidine-1-carbonyl)-3-cyclopropylacrylonitrile; 56A (S)-2-(3-(4-amino-5-(2-fluoro-4-phenoxyphenyl)-7H-pyrrolo[2,3-d]pyrimidin-7-yl)piperidine-1-carbonyl)-3-cyclopropylacrylonitrile; 56B (R)-2-(2-((4-amino-5-(4-phenoxyphenyl)-7H-pyrrolo[2,3-d]pyrimidin-7-yl)methyl)pyrrolidine-1-carbonyl)-3-cyclopropylacrylonitrile; 57A (S)-2-(2-((4-amino-5-(4-phenoxyphenyl)-7H-pyrrolo[2,3-d]pyrimidin-7-yl)methyl)pyrrolidine-1-carbonyl)-3-cyclopropylacrylonitrile; 57B (R)-2-(2-((4-amino-5-(4-(3,5-difluorophenoxy)phenyl)-7H-pyrrolo[2,3-d]pyrimidin-7-yl)methyl)pyrrolidine-1-carbonyl)-3-cyclopropylacrylonitrile; 58A (S)-2-(2-((4-amino-5-(4-(3,5-difluorophenoxy)phenyl)-7H-pyrrolo[2,3-d]pyrimidin-7-yl)methyl)pyrrolidine-1-carbonyl)-3-cyclopropylacrylonitrile; 58B (R)-2-(2-((4-amino-5-(2-fluoro-4-phenoxyphenyl)-7H-pyrrolo[2,3-d]pyrimidin-7-yl)methyl)pyrrolidine-1-carbonyl)-3-cyclopropylacrylonitrile; 59A (S)-2-(2-((4-amino-5-(2-fluoro-4-phenoxyphenyl)-7H-pyrrolo[2,3-d]pyrimidin-7-yl)methyl)pyrrolidine-1-carbonyl)-3-cyclopropylacrylonitrile; 59B (R)-2-(3-(4-amino-6-methyl-5-(4-phenoxyphenyl)-7H-pyrrolo[2,3-d]pyrimidin-7-yl)piperidine-1-carbonyl)-3-cyclopropylacrylonitrile; 60A (S)-2-(3-(4-amino-6-methyl-5-(4-phenoxyphenyl)-7H-pyrrolo[2,3-d]pyrimidin-7-yl)piperidine-1-carbonyl)-3-cyclopropylacrylonitrile; 60B (R)-2-(3-(4-amino-5-(4-(3,5-difluorophenoxy)phenyl)-6-methyl-7H-pyrrolo[2,3-d]pyrimidin-7-yl)piperidine-1-carbonyl)-3-cyclopropylacrylonitrile; 61A (S)-2-(3-(4-amino-5-(4-(3,5-difluorophenoxy)phenyl)-6-methyl-7H-pyrrolo[2,3-d]pyrimidin-7-yl)piperidine-1-carbonyl)-3-cyclopropylacrylonitrile; 61B 2-((3R)-3-(4-amino-5-(2-fluoro-4-phenoxyphenyl)-6-methyl-7H-pyrrolo[2,3-d]pyrimidin-7-yl)piperidine-1-carbonyl)-3-cyclopropylacrylonitrile; 62A 2-((3S)-3-(4-amino-5-(2-fluoro-4-phenoxyphenyl)-6-methyl-7H-pyrrolo[2,3-d]pyrimidin-7-yl)piperidine-1-carbonyl)-3-cyclopropylacrylonitrile; 62B (R)-(2-(2-((4-amino-6-methyl-5-(4-phenoxyphenyl)-7H-pyrrolo[2,3-d]pyrimidin-7-yl)methyl)pyrrolidine-1-carbonyl)-3-cyclopropylacrylonitrile; 63A (S)-(2-(2-((4-amino-6-methyl-5-(4-phenoxyphenyl)-7H-pyrrolo[2,3-d]pyrimidin-7-yl)methyl)pyrrolidine-1-carbonyl)-3-cyclopropylacrylonitrile; 63B (R)-2-(2-((4-amino-5-(4-(3,5-difluorophenoxy)phenyl)-6-methyl-7H-pyrrolo[2,3-d]pyrimidin-7-yl)methyl)pyrrolidine-1-carbonyl)-3-cyclopropylacrylonitrile; 64A (S)-2-(2-((4-amino-5-(4-(3,5-difluorophenoxy)phenyl)-6-methyl-7H-pyrrolo[2,3-d]pyrimidin-7-yl)methyl)pyrrolidine-1-carbonyl)-3-cyclopropylacrylonitrile; 64B (R)-2-(2-((4-amino-5-(2-fluoro-4-phenoxyphenyl)-6-methyl-7H-pyrrolo[2,3-d]pyrimidin-7-yl)methyl)pyrrolidine-1-carbonyl)-3-cyclopropylacrylonitrile; 65A (S)-2-(2-((4-amino-5-(2-fluoro-4-phenoxyphenyl)-6-methyl-7H-pyrrolo[2,3-d]pyrimidin-7-yl)methyl)pyrrolidine-1-carbonyl)-3-cyclopropylacrylonitrile; 65B 2-(3-((4-amino-3-(4-phenoxyphenyl)-1H-pyrazolo[3,4-d]pyrimidin-1-yl)methyl)pyrrolidine-1-carbonyl)-3-cyclopropylacrylonitrile; 66

N-(3-(4-amino-3-(4-phenoxyphenyl)-1H-pyrazolo[3,4-d]pyrimidin-1-yl)-2,2-dimethylpropyl)-2-cyano-3-cyclopropylacrylamide; 67

2-(4-(4-amino-3-(4-phenoxyphenyl)-1H-pyrazolo[3,4-d]pyrimidin-1-yl)pyridin-2-yl)-3-cyclopropylacrylonitrile; 68

(R)-2-(2-((4-amino-3-(2-methyl-4-phenoxyphenyl)-1H-pyrazolo[3,4-d]pyrimidin-1-yl)methyl)pyrrolidine-1-carbonyl)-3-cyclopropylacrylonitrile; 69A (S)-2-(2-((4-amino-3-(2-methyl-4-phenoxyphenyl)-1H-pyrazolo[3,4-d]pyrimidin-1-yl)methyl)pyrrolidine-1-carbonyl)-3-cyclopropylacrylonitrile; 69B (R)-2-(2-((4-amino-3-(2-chloro-4-phenoxyphenyl)-1H-pyrazolo[3,4-d]pyrimidin-1-yl)methyl)pyrrolidine-1-carbonyl)-3-cyclopropylacrylonitrile; 70A (S)-2-(2-((4-amino-3-(2-chloro-4-phenoxyphenyl)-1H-pyrazolo[3,4-d]pyrimidin-1-yl)methyl)pyrrolidine-1-carbonyl)-3-cyclopropylacrylonitrile; 70B (R)-2-(2-((4-amino-3-(4-(2,5-difluorophenoxy)phenyl)-1H-pyrazolo[3,4-d]pyrimidin-1-yl)methyl)pyrrolidine-1-carbonyl)-4-methylpent-2-enenitrile; 71A (S)-2-(2-((4-amino-3-(4-(2,5-difluorophenoxy)phenyl)-1H-pyrazolo[3,4-d]pyrimidin-1-yl)methyl)pyrrolidine-1-carbonyl)-4-methylpent-2-enenitrile; 71B (R)-4-amino-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile; 72A (S)-4-amino-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile; 72B (R)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile; 73A (S)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile; 73B (R)-2-(2-((4-amino-3-(2-fluoro-4-phenoxyphenyl)-1H-pyrazolo[3,4-d]pyrimidin-1-yl)methyl)pyrrolidine-1-carbonyl)-4,4-dimethylpent-2-enenitrile; 74A (S)-2-(2-((4-amino-3-(2-fluoro-4-phenoxyphenyl)-1H-pyrazolo[3,4-d]pyrimidin-1-yl)methyl)pyrrolidine-1-carbonyl)-4,4-dimethylpent-2-enenitrile; 74B (R)-2-(2-((4-amino-3-(4-(2,6-difluorophenoxy)phenyl)-1H-pyrazolo[3,4-d]pyrimidin-1-yl)methyl)pyrrolidine-1-carbonyl)-4-methylpent-2-enenitrile; 75A (S)-2-(2-((4-amino-3-(4-(2,6-difluorophenoxy)phenyl)-1H-pyrazolo[3,4-d]pyrimidin-1-yl)methyl)pyrrolidine-1-carbonyl)-4-methylpent-2-enenitrile; 75B (R)-2-(2-((4-amino-3-(4-(2,3-difluorophenoxy)phenyl)-1H-pyrazolo[3,4-d]pyrimidin-1-yl)methyl)pyrrolidine-1-carbonyl)-4-methylpent-2-enenitrile; 76A (S)-2-(2-((4-amino-3-(4-(2,3-difluorophenoxy)phenyl)-1H-pyrazolo[3,4-d]pyrimidin-1-yl)methyl)pyrrolidine-1-carbonyl)-4-methylpent-2-enenitrile; 76B (R)-2-(2-((4-amino-6-methyl-5-(4-phenoxyphenyl)-7H-pyrrolo[2,3-d]pyrimidin-7-yl)methyl)pyrrolidine-1-carbonyl)-4-(dimethylamino)-4-methylpent-2-enenitrile; 77A (S)-2-(2-((4-amino-6-methyl-5-(4-phenoxyphenyl)-7H-pyrrolo[2,3-d]pyrimidin-7-yl)methyl)pyrrolidine-1-carbonyl)-4-(dimethylamino)-4-methylpent-2-enenitrile; 77B (R)-2-(2-((4-amino-3-(4-(2,6-difluorophenoxy)-2-fluorophenyl)-1H-pyrazolo[3,4-d]pyrimidin-1-yl)methyl)pyrrolidine-1-carbonyl)-4-methylpent-2-enenitrile; 78A (S)-2-(2-((4-amino-3-(4-(2,6-difluorophenoxy)-2-fluorophenyl)-1H-pyrazolo[3,4-d]pyrimidin-1-yl)methyl)pyrrolidine-1-carbonyl)-4-methylpent-2-enenitrile; 78B (R)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-3-cyclopropylacrylonitrile; 79A (S)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-3-cyclopropylacrylonitrile; 79B (R)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-4-methylpent-2-enenitrile; 80A (S)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-4-methylpent-2-enenitrile; 80B (R)-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile; 81A (S)-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile; 81B (S)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile; 82B (R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile; 82A (S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(methylamino)pent-2-enenitrile; 83B (R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(methylamino)pent-2-enenitrile; 84A (S)-2-(2-((4-amino-3-(2-fluoro-4-phenoxyphenyl)-1H-pyrazolo[3,4-d]pyrimidin-1-yl)methyl)pyrrolidine-1-carbonyl)-4-(dimethylamino)-4-methylpent-2-enenitrile; 84B (R)-2-(2-((4-amino-3-(2-fluoro-4-phenoxyphenyl)-1H-pyrazolo[3,4-d]pyrimidin-1-yl)methyl)pyrrolidine-1-carbonyl)-4-(dimethylamino)-4-methylpent-2-enenitrile; 84A (S)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile; 85B (R)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile; 85A (S)-2-(2-((4-amino-3-(2-fluoro-4-phenoxyphenyl)-1H-pyrazolo[3,4-d]pyrimidin-1-yl)methyl)pyrrolidine-1-carbonyl)-4-(isopropylamino)-4-methylpent-2-enenitrile; 86B (R)-2-(2-((4-amino-3-(2-fluoro-4-phenoxyphenyl)-1H-pyrazolo[3,4-d]pyrimidin-1-yl)methyl)pyrrolidine-1-carbonyl)-4-(isopropylamino)-4-methylpent-2-enenitrile; 86A (S)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropylamino)-4-methylpent-2-enenitrile; 87B (R)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropylamino)-4-methylpent-2-enenitrile; 87A (S)-2-(2-((4-amino-3-(2-fluoro-4-phenoxyphenyl)-1H-pyrazolo[3,4-d]pyrimidin-1-yl)methyl)pyrrolidine-1-carbonyl)-4-((2-methoxyethyl)amino)-4-methylpent-2-enenitrile; 88B (R)-2-(2-((4-amino-3-(2-fluoro-4-phenoxyphenyl)-1H-pyrazolo[3,4-d]pyrimidin-1-yl)methyl)pyrrolidine-1-carbonyl)-4-((2-methoxyethyl)amino)-4-methylpent-2-enenitrile; 88A (S)-2-(2-((4-amino-3-(2-fluoro-4-phenoxyphenyl)-1H-pyrazolo[3,4-d]pyrimidin-1-yl)methyl)pyrrolidine-1-carbonyl)-4-ethoxy-4-methylpent-2-enenitrile; 89B (R)-2-(2-((4-amino-3-(2-fluoro-4-phenoxyphenyl)-1H-pyrazolo[3,4-d]pyrimidin-1-yl)methyl)pyrrolidine-1-carbonyl)-4-ethoxy-4-methylpent-2-enenitrile; 89A (S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-aminocyclopropyl)acrylonitrile; 90B (R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-aminocyclopropyl)acrylonitrile; 90A (S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(methylamino)cyclopropyl)acrylonitrile; 91B (R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(methylamino)cyclopropyl)acrylonitrile; 91A (S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(ethylamino)cyclopropyl)acrylonitrile; 92B (R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(ethylamino)cyclopropyl)acrylonitrile; 92A (S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(isopropylamino)cyclopropyl)acrylonitrile; 93B (R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(isopropylamino)cyclopropyl)acrylonitrile; 93A 2-((S)-2-((4-amino-3-(2-fluoro-4-phenoxyphenyl)-1H-pyrazolo[3,4-d]pyrimidin-1-yl)methyl)pyrrolidine-1-carbonyl)-3-(pyrrolidin-2-yl)acrylonitrile; 94B 2-((R)-2-((4-amino-3-(2-fluoro-4-phenoxyphenyl)-1H-pyrazolo[3,4-d]pyrimidin-1-yl)methyl)pyrrolidine-1-carbonyl)-3-(pyrrolidin-2-yl)acrylonitrile; 94A (S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile; 95B (R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile; 95A (S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-((dimethylamino)methyl)cyclopentyl)acrylonitrile; 97B (R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-((dimethylamino)methyl)cyclopentyl)acrylonitrile; 97A (S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-methylpiperidin-4-yl)acrylonitrile; 98B (R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-methylpiperidin-4-yl)acrylonitrile; 98A (S)-2-(2-((4-amino-3-(2-fluoro-4-phenoxyphenyl)-1H-pyrazolo[3,4-d]pyrimidin-1-yl)methyl)pyrrolidine-1-carbonyl)-3-(tetrahydro-2H-pyran-4-yl)acrylonitrile; 99B (R)-2-(2-((4-amino-3-(2-fluoro-4-phenoxyphenyl)-1H-pyrazolo[3,4-d]pyrimidin-1-yl)methyl)pyrrolidine-1-carbonyl)-3-(tetrahydro-2H-pyran-4-yl)acrylonitrile; 99A (S)-2-(2-((4-amino-3-(2-fluoro-4-phenoxyphenyl)-1H-pyrazolo[3,4-d]pyrimidin-1-yl)methyl)pyrrolidine-1-carbonyl)-3-(piperidin-4-yl)acrylonitrile; 100B (R)-2-(2-((4-amino-3-(2-fluoro-4-phenoxyphenyl)-1H-pyrazolo[3,4-d]pyrimidin-1-yl)methyl)pyrrolidine-1-carbonyl)-3-(piperidin-4-yl)acrylonitrile; 100A 2-((S)-2-((4-amino-3-(2-fluoro-4-phenoxyphenyl)-1H-pyrazolo[3,4-d]pyrimidin-1-yl)methyl)pyrrolidine-1-carbonyl)-3-(piperidin-3-yl)acrylonitrile; 101B 2-((R)-2-((4-amino-3-(2-fluoro-4-phenoxyphenyl)-1H-pyrazolo[3,4-d]pyrimidin-1-yl)methyl)pyrrolidine-1-carbonyl)-3-(piperidin-3-yl)acrylonitrile; 101A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile; 102B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile; 102A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4,4-dimethylpent-2-enenitrile; 103B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4,4-dimethylpent-2-enenitrile; 103A (S)-4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile; 104B (R)-4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile; 104A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-(methylamino)pent-2-enenitrile; 105B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-(methylamino)pent-2-enenitrile; 105A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(dimethylamino)-4-methylpent-2-enenitrile; 106B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(dimethylamino)-4-methylpent-2-enenitrile; 106A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(ethylamino)-4-methylpent-2-enenitrile; 107B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(ethylamino)-4-methylpent-2-enenitrile; 107A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(isopropylamino)-4-methylpent-2-enenitrile; 108B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(isopropylamino)-4-methylpent-2-enenitrile; 108A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(cyclopropylamino)-4-methylpent-2-enenitrile; 109B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(cyclopropylamino)-4-methylpent-2-enenitrile; 109A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-((2-methoxyethyl)amino)-4-methylpent-2-enenitrile; 110B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-((2-methoxyethyl)amino)-4-methylpent-2-enenitrile; 110A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-ethoxy-4-methylpent-2-enenitrile; 111B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-ethoxy-4-methylpent-2-enenitrile; 111A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-aminocyclopropyl)acrylonitrile; 112B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-aminocyclopropyl)acrylonitrile; 112A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(methylamino)cyclopropyl)-acrylonitrile; 113B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(methylamino)cyclopropyl)-acrylonitrile; 113A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(ethylamino)cyclopropyl)acrylonitrile; 114B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(ethylamino)cyclopropyl)acrylonitrile; 114A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(isopropylamino)cyclopropyl)-acrylonitrile; 115B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(isopropylamino)cyclopropyl)-acrylonitrile; 115A 2-((S)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(pyrrolidin-2-yl)acrylonitrile; 116B 2-((R)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(pyrrolidin-2-yl)acrylonitrile; 116A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-morpholinopent-2-enenitrile; 117B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-morpholinopent-2-enenitrile; 117A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((diethylamino)methyl)cyclopentyl)-acrylonitrile; 118B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((diethylamino)methyl)cyclopentyl)-acrylonitrile; 118A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((dimethylamino)methyl)-cyclopentyl)acrylonitrile; 119B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((dimethylamino)-methyl)-cyclopentyl)acrylonitrile; 119A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-methylpiperidin-4-yl)acrylonitrile; 120B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-methylpiperidin-4-yl)acrylonitrile; 120A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(tetrahydro-2H-pyran-4-yl)acrylonitrile; 121B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(tetrahydro-2H-pyran-4-yl)acrylonitrile; 121A (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-4-yl)acrylonitrile; 122B (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-4-yl)acrylonitrile; 122A 2-((S)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-3-yl)acrylonitrile; 123B 2-((R)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-3-yl)acrylonitrile; 123A (R)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile; 124A (S)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile; 124B (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile; 125A (S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile; 125B (R)-4-amino-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile; 126A (S)-4-amino-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile; 126B (R)-2-(3-(4-amino-3-(2-fluoro-4-phenoxyphenyl)-1H-pyrazolo[3,4-d]pyrimidin-1-yl)piperidine-1-carbonyl)-4-methyl-4-(methylamino)pent-2-enenitrile; 127A (S)-2-(3-(4-amino-3-(2-fluoro-4-phenoxyphenyl)-1H-pyrazolo[3,4-d]pyrimidin-1-yl)piperidine-1-carbonyl)-4-methyl-4-(methylamino)pent-2-enenitrile; 127B (R)-2-(3-(4-amino-3-(2-fluoro-4-phenoxyphenyl)-1H-pyrazolo[3,4-d]pyrimidin-1-yl)piperidine-1-carbonyl)-4-(dimethylamino)-4-methylpent-2-enenitrile; 128A (S)-2-(3-(4-amino-3-(2-fluoro-4-phenoxyphenyl)-1H-pyrazolo[3,4-d]pyrimidin-1-yl)piperidine-1-carbonyl)-4-(dimethylamino)-4-methylpent-2-enenitrile; 128B (R)-2-(3-(4-amino-3-(2-fluoro-4-phenoxyphenyl)-1H-pyrazolo[3,4-d]pyrimidin-1-yl)piperidine-1-carbonyl)-4-(ethylamino)-4-methylpent-2-enenitrile; 129A (S)-2-(3-(4-amino-3-(2-fluoro-4-phenoxyphenyl)-1H-pyrazolo[3,4-d]pyrimidin-1-yl)piperidine-1-carbonyl)-4-(ethylamino)-4-methylpent-2-enenitrile; 129B (R)-2-(3-(4-amino-3-(2-fluoro-4-phenoxyphenyl)-1H-pyrazolo[3,4-d]pyrimidin-1-yl)piperidine-1-carbonyl)-4-(isopropylamino)-4-methylpent-2-enenitrile; 130A (S)-2-(3-(4-amino-3-(2-fluoro-4-phenoxyphenyl)-1H-pyrazolo[3,4-d]pyrimidin-1-yl)piperidine-1-carbonyl)-4-(isopropylamino)-4-methylpent-2-enenitrile; 130B (R)-2-(3-(4-amino-3-(2-fluoro-4-phenoxyphenyl)-1H-pyrazolo[3,4-d]pyrimidin-1-yl)piperidine-1-carbonyl)-4-(cyclopropylamino)-4-methylpent-2-enenitrile; 131A (S)-2-(3-(4-amino-3-(2-fluoro-4-phenoxyphenyl)-1H-pyrazolo[3,4-d]pyrimidin-1-yl)piperidine-1-carbonyl)-4-(cyclopropylamino)-4-methylpent-2-enenitrile; 131B (R)-2-(3-(4-amino-3-(2-fluoro-4-phenoxyphenyl)-1H-pyrazolo[3,4-d]pyrimidin-1-yl)piperidine-1-carbonyl)-4-((2-methoxyethyl)amino)-4-methylpent-2-enenitrile; 132A (S)-2-(3-(4-amino-3-(2-fluoro-4-phenoxyphenyl)-1H-pyrazolo[3,4-d]pyrimidin-1-yl)piperidine-1-carbonyl)-4-((2-methoxyethyl)amino)-4-methylpent-2-enenitrile; 132B (R)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile; 133A (S)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile; 133B (R)-2-(3-(4-amino-3-(2-fluoro-4-phenoxyphenyl)-1H-pyrazolo[3,4-d]pyrimidin-1-yl)piperidine-1-carbonyl)-3-(1-aminocyclopropyl)acrylonitrile; 134A (S)-2-(3-(4-amino-3-(2-fluoro-4-phenoxyphenyl)-1H-pyrazolo[3,4-d]pyrimidin-1-yl)piperidine-1-carbonyl)-3-(1-aminocyclopropyl)acrylonitrile; 134B (R)-2-(3-(4-amino-3-(2-fluoro-4-phenoxyphenyl)-1H-pyrazolo[3,4-d]pyrimidin-1-yl)piperidine-1-carbonyl)-3-(1-(methylamino)cyclopropyl)acrylonitrile; 135A (S)-2-(3-(4-amino-3-(2-fluoro-4-phenoxyphenyl)-1H-pyrazolo[3,4-d]pyrimidin-1-yl)piperidine-1-carbonyl)-3-(1-(methylamino)cyclopropyl)acrylonitrile; 135B (R)-2-(3-(4-amino-3-(2-fluoro-4-phenoxyphenyl)-1H-pyrazolo[3,4-d]pyrimidin-1-yl)piperidine-1-carbonyl)-3-(1-(ethylamino)cyclopropyl)acrylonitrile; 136A (S)-2-(3-(4-amino-3-(2-fluoro-4-phenoxyphenyl)-1H-pyrazolo[3,4-d]pyrimidin-1-yl)piperidine-1-carbonyl)-3-(1-(ethylamino)cyclopropyl)acrylonitrile; 136B (R)-2-(3-(4-amino-3-(2-fluoro-4-phenoxyphenyl)-1H-pyrazolo[3,4-d]pyrimidin-1-yl)piperidine-1-carbonyl)-3-(1-(isopropylamino)cyclopropyl)acrylonitrile; 137A (S)-2-(3-(4-amino-3-(2-fluoro-4-phenoxyphenyl)-1H-pyrazolo[3,4-d]pyrimidin-1-yl)piperidine-1-carbonyl)-3-(1-(isopropylamino)cyclopropyl)acrylonitrile; 137B 2-((R)-3-(4-amino-3-(2-fluoro-4-phenoxyphenyl)-1H-pyrazolo[3,4-d]pyrimidin-1-yl)piperidine-1-carbonyl)-3-(pyrrolidin-2-yl)acrylonitrile; 138A 2-((S)-3-(4-amino-3-(2-fluoro-4-phenoxyphenyl)-1H-pyrazolo[3,4-d]pyrimidin-1-yl)piperidine-1-carbonyl)-3-(pyrrolidin-2-yl)acrylonitrile; 138B (S)-2-(3-(4-amino-3-(2-fluoro-4-phenoxyphenyl)-1H-pyrazolo[3,4-d]pyrimidin-1-yl)piperidine-1-carbonyl)-4-methyl-4-morpholinopent-2-enenitrile; 139B (R)-2-(3-(4-amino-3-(2-fluoro-4-phenoxyphenyl)-1H-pyrazolo[3,4-d]pyrimidin-1-yl)piperidine-1-carbonyl)-4-methyl-4-morpholinopent-2-enenitrile; 139A (R)-2-(3-(4-amino-3-(2-fluoro-4-phenoxyphenyl)-1H-pyrazolo[3,4-d]pyrimidin-1-yl)piperidine-1-carbonyl)-3-(1-((diethylamino)methyl)-cyclopentyl)acrylonitrile; 140A (S)-2-(3-(4-amino-3-(2-fluoro-4-phenoxyphenyl)-1H-pyrazolo[3,4-d]pyrimidin-1-yl)piperidine-1-carbonyl)-3-(1-((diethylamino)methyl)-cyclopentyl)acrylonitrile; 140B (R)-2-(3-(4-amino-3-(2-fluoro-4-phenoxyphenyl)-1H-pyrazolo[3,4-d]pyrimidin-1-yl)piperidine-1-carbonyl)-3-(1-((dimethylamino)methyl)cyclopentyl)-acrylonitrile; 141A (S)-2-(3-(4-amino-3-(2-fluoro-4-phenoxyphenyl)-1H-pyrazolo[3,4-d]pyrimidin-1-yl)piperidine-1-carbonyl)-3-(1-((dimethylamino)methyl)cyclopentyl)-acrylonitrile; 141B (R)-2-(3-(4-amino-3-(2-fluoro-4-phenoxyphenyl)-1H-pyrazolo[3,4-d]pyrimidin-1-yl)piperidine-1-carbonyl)-3-(1-methylpiperidin-4-yl)acrylonitrile; 142A
(S)-2-(3-(4-amino-3-(2-fluoro-4-phenoxyphenyl)-1H-pyrazolo[3,4-d]pyrimidin-1-yl)piperidine-1-carbonyl)-3-(1-methylpiperidin-4-yl)acrylonitrile; 142B
(R)-2-(3-(4-amino-3-(2-fluoro-4-phenoxyphenyl)-1H-pyrazolo[3,4-d]pyrimidin-1-yl)piperidine-1-carbonyl)-3-(tetrahydro-2H-pyran-4-yl)acrylonitrile; 143A
(S)-2-(3-(4-amino-3-(2-fluoro-4-phenoxyphenyl)-1H-pyrazolo[3,4-d]pyrimidin-1-yl)piperidine-1-carbonyl)-3-(tetrahydro-2H-pyran-4-yl)acrylonitrile; 143B
(R)-2-(3-(4-amino-3-(2-fluoro-4-phenoxyphenyl)-1H-pyrazolo[3,4-d]pyrimidin-1-yl)piperidine-1-carbonyl)-3-(piperidin-4-yl)acrylonitrile; 144A
(S)-2-(3-(4-amino-3-(2-fluoro-4-phenoxyphenyl)-1H-pyrazolo[3,4-d]pyrimidin-1-yl)piperidine-1-carbonyl)-3-(piperidin-4-yl)acrylonitrile; 144B
2-((R)-3-(4-amino-3-(2-fluoro-4-phenoxyphenyl)-1H-pyrazolo[3,4-d]pyrimidin-1-yl)piperidine-1-carbonyl)-3-(piperidin-3-yl)acrylonitrile; 145A
2-((S)-3-(4-amino-3-(2-fluoro-4-phenoxyphenyl)-1H-pyrazolo[3,4-d]pyrimidin-1-yl)piperidine-1-carbonyl)-3-(piperidin-3-yl)acrylonitrile; 145B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-cyclopropylacrylonitrile; 146A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-cyclopropylacrylonitrile; 146B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile; 147A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile; 147B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4,4-dimethylpent-2-enenitrile; 148A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-4,4-dimethylpent-2-enenitrile; 148B
(R)-4-amino-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile; 149A
(S)-4-amino-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile; 149B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-(methylamino)pent-2-enenitrile; 150A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-(methylamino)pent-2-enenitrile; 150B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(dimethylamino)-4-methylpent-2-enenitrile; 151A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(dimethylamino)-4-methylpent-2-enenitrile; 151B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(ethylamino)-4-methylpent-2-enenitrile; 152A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(ethylamino)-4-methylpent-2-enenitrile; 152B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(isopropylamino)-4-methylpent-2-enenitrile; 153A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(isopropylamino)-4-methylpent-2-enenitrile; 153B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(cyclopropylamino)-4-methylpent-2-enenitrile; 154A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(cyclopropylamino)-4-methylpent-2-enenitrile 154B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-((2-methoxyethyl)amino)-4-methylpent-2-enenitrile; 155A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-((2-methoxyethyl)amino)-4-methylpent-2-enenitrile; 155B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-ethoxy-4-methylpent-2-enenitrile; 156A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-ethoxy-4-methylpent-2-enenitrile; 156B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-aminocyclopropyl)-acrylonitrile; 157A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-aminocyclopropyl)-acrylonitrile; 157B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(methylamino)cyclopropyl)-acrylonitrile; 158A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(methylamino)cyclopropyl)-acrylonitrile; 158B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(ethylamino)cyclopropyl)-acrylonitrile; 159A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(ethylamino)cyclopropyl)-acrylonitrile; 159B
(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(isopropylamino)-cyclopropyl)acrylonitrile; 160A
(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(isopropylamino)-cyclopropyl)acrylonitrile; 160B
2-((R)-3-(4-amino-3-(4-(2,3-difluorophenoxy)-2-fluorophenyl)-1H-pyrazolo[3,4-d]pyrimidin-1-yl)piperidine-1-carbonyl)-3-(pyrrolidin-2-yl)acrylonitrile; 161A 2-((S)-3-(4-amino-3-(4-(2,3-difluorophenoxy)-2-fluorophenyl)-1H-pyrazolo[3,4-d]pyrimidin-1-yl)piperidine-1-carbonyl)-3-(pyrrolidin-2-yl)acrylonitrile; 161B (R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-morpholinopent-2-enenitrile; 162A (S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-morpholinopent-2-enenitrile; 162B (R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((diethylamino)methyl)-cyclopentyl)-acrylonitrile; 163A (S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((diethylamino)methyl)-cyclopentyl)-acrylonitrile; 163B (R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((dimethylamino)-methyl)cyclopentyl)-acrylonitrile; 164A (S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((dimethylamino)-methyl)cyclopentyl)-acrylonitrile; 164B (R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-methylpiperidin-4-yl)acrylonitrile; 165A (S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-methylpiperidin-4-yl)acrylonitrile; 165B (R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(tetrahydro-2H-pyran-4-yl)acrylonitrile; 166A (S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(tetrahydro-2H-pyran-4-yl)acrylonitrile; 166B (R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(piperidin-4-yl)acrylonitrile; 167A (S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(piperidin-4-yl)acrylonitrile; 167B 2-((R)-3-(4-amino-3-(4-(2,3-difluorophenoxy)-2-fluorophenyl)-1H-pyrazolo[3,4-d]pyrimidin-1-yl)piperidine-1-carbonyl)-3-(piperidin-3-yl)acrylonitrile; 168A 2-((S)-3-(4-amino-3-(4-(2,3-difluorophenoxy)-2-fluorophenyl)-1H-pyrazolo[3,4-d]pyrimidin-1-yl)piperidine-1-carbonyl)-3-(piperidin-3-yl)acrylonitrile; 168B (R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile; 169A (S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile; 169B (R)-2-(2-((4-amino-5-(2-fluoro-4-phenoxyphenyl)-7H-pyrrolo[2,3-d]pyrimidin-7-yl)methyl)pyrrolidine-1-carbonyl)-4-(dimethylamino)-4-methylpent-2-enenitrile; 170A (S)-2-(2-((4-amino-5-(2-fluoro-4-phenoxyphenyl)-7H-pyrrolo[2,3-d]pyrimidin-7-yl)methyl)pyrrolidine-1-carbonyl)-4-(dimethylamino)-4-methylpent-2-enenitrile; 170B (R)-2-(2-((4-amino-5-(4-(2,3-difluorophenoxy)phenyl)-7H-pyrrolo[2,3-d]pyrimidin-7-yl)methyl)pyrrolidine-1-carbonyl)-3-cyclopropylacrylonitrile; 171A (S)-2-(2-((4-amino-5-(4-(2,3-difluorophenoxy)phenyl)-7H-pyrrolo[2,3-d]pyrimidin-7-yl)methyl)pyrrolidine-1-carbonyl)-3-cyclopropylacrylonitrile; 171B (R)-2-(2-((4-amino-5-(4-(2,3-difluorophenoxy)phenyl)-7H-pyrrolo[2,3-d]pyrimidin-7-yl)methyl)pyrrolidine-1-carbonyl)-4-methylpent-2-enenitrile; 172A (S)-2-(2-((4-amino-5-(4-(2,3-difluorophenoxy)phenyl)-7H-pyrrolo[2,3-d]pyrimidin-7-yl)methyl)pyrrolidine-1-carbonyl)-4-methylpent-2-enenitrile; 172B (R)-2-(2-((4-amino-5-(4-(2,3-difluorophenoxy)phenyl)-7H-pyrrolo[2,3-d]pyrimidin-7-yl)methyl)pyrrolidine-1-carbonyl)-4,4-dimethylpent-2-enenitrile; 173A (S)-2-(2-((4-amino-5-(4-(2,3-difluorophenoxy)phenyl)-7H-pyrrolo[2,3-d]pyrimidin-7-yl)methyl)pyrrolidine-1-carbonyl)-4,4-dimethylpent-2-enenitrile; 173B (R)-2-(2-((4-amino-5-(4-(2,3-difluorophenoxy)phenyl)-7H-pyrrolo[2,3-d]pyrimidin-7-yl)methyl)pyrrolidine-1-carbonyl)-4-(dimethylamino)-4-methylpent-2-enenitrile; 174A (S)-2-(2-((4-amino-5-(4-(2,3-difluorophenoxy)phenyl)-7H-pyrrolo[2,3-d]pyrimidin-7-yl)methyl)pyrrolidine-1-carbonyl)-4-(dimethylamino)-4-methylpent-2-enenitrile; 174B (R)-2-(2-((4-amino-5-(4-phenoxyphenyl)-7H-pyrrolo[2,3-d]pyrimidin-7-yl)methyl)-pyrrolidine-1-carbonyl)-4-(dimethylamino)-4-methylpent-2-enenitrile; 175A (S)-2-(2-((4-amino-5-(4-phenoxyphenyl)-7H-pyrrolo[2,3-d]pyrimidin-7-yl)methyl)-pyrrolidine-1-carbonyl)-4-(dimethylamino)-4-methylpent-2-enenitrile; 175B (R)-2-(2-((4-amino-5-(4-phenoxyphenyl)-7H-pyrrolo[2,3-d]pyrimidin-7-yl)methyl)-pyrrolidine-1-carbonyl)-4-methylpent-2-enenitrile; 176A (S)-2-(2-((4-amino-5-(4-phenoxyphenyl)-7H-pyrrolo[2,3-d]pyrimidin-7-yl)methyl)-pyrrolidine-1-carbonyl)-4-methylpent-2-enenitrile; 176B (R)-4-amino-2-(2-((4-amino-5-(2-fluoro-4-phenoxyphenyl)-7H-pyrrolo[2,3-d]-pyrimidin-7-yl)methyl)pyrrolidine-1-carbonyl)-4-methylpent-2-enenitrile; 177A (S)-4-amino-2-(2-((4-amino-5-(2-fluoro-4-phenoxyphenyl)-7H-pyrrolo[2,3-d]-pyrimidin-7-yl)methyl)pyrrolidine-1-carbonyl)-4-methylpent-2-enenitrile; 177B (R)-2-(2-((4-amino-5-(4-phenoxyphenyl)-7H-pyrrolo[2,3-d]pyrimidin-7-yl)-methyl)pyrrolidine-1-carbonyl)-4-(dimethylamino)-4-methylpent-2-enenitrile; 178A (S)-2-(2-((4-amino-5-(4-phenoxyphenyl)-7H-pyrrolo[2,3-d]pyrimidin-7-yl)-methyl)pyrrolidine-1-carbonyl)-4-(dimethylamino)-4-methylpent-2-enenitrile; 178B (R)-2-(2-((4-amino-5-(4-phenoxyphenyl)-7H-pyrrolo[2,3-d]pyrimidin-7-yl)-methyl)pyrrolidine-1-carbonyl)-4-methyl-4-morpholinopent-2-enenitrile 179A (S)-2-(2-((4-amino-5-(4-phenoxyphenyl)-7H-pyrrolo[2,3-d]pyrimidin-7-yl)-methyl)pyrrolidine-1-carbonyl)-4-methyl-4-morpholinopent-2-enenitrile; 179B (R)-2-(2-((4-amino-5-(4-phenoxyphenyl)-7H-pyrrolo[2,3-d]pyrimidin-7-yl)-methyl)pyrrolidine-1-carbonyl)-4-(diethylamino)-4-methylpent-2-enenitrile; 180A (S)-2-(2-((4-amino-5-(4-phenoxyphenyl)-7H-pyrrolo[2,3-d]pyrimidin-7-yl)-methyl)pyrrolidine-1-carbonyl)-4-(diethylamino)-4-methylpent-2-enenitrile; 180B (R)-2-(2-((4-amino-5-(4-phenoxyphenyl)-7H-pyrrolo[2,3-d]pyrimidin-7-yl)-methyl)pyrrolidine-1-carbonyl)-4-ethoxy-4-methylpent-2-enenitrile; 181A (S)-2-(2-((4-amino-5-(4-phenoxyphenyl)-7H-pyrrolo[2,3-d]pyrimidin-7-yl)-methyl)pyrrolidine-1-carbonyl)-4-ethoxy-4-methylpent-2-enenitrile; 181B (R)—N-(1-(4-amino-3-(2-fluoro-4-phenoxyphenyl)-1H-pyrazolo[3,4-d]pyrimidin-1-yl)-propan-2-yl)-2-cyano-4,4-dimethylpent-2-enamide; 182A (S)—N-(1-(4-amino-3-(2-fluoro-4-phenoxyphenyl)-1H-pyrazolo[3,4-d]pyrimidin-1-yl)propan-2-yl)-2-cyano-4,4-dimethylpent-2-enamide; 182B (R)—N-(1-(4-amino-3-(2-fluoro-4-phenoxyphenyl)-1H-pyrazolo[3,4-d]pyrimidin-1-yl)propan-2-yl)-2-cyano-4-methylpent-2-enamide; 183A (S)—N-(1-(4-amino-3-(2-fluoro-4-phenoxyphenyl)-1H-pyrazolo[3,4-d]pyrimidin-1-yl)propan-2-yl)-2-cyano-4-methylpent-2-enamide; 183B (R)—N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide; 184A (S)—N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide; 184B (R)—N-(1-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide; 185A (S)—N-(1-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide; 185B 2-((R)-2-((4-amino-3-(2-fluoro-4-phenoxyphenyl)-1H-pyrazolo[3,4-d]pyrimidin-1-yl)methyl)pyrrolidine-1-carbonyl)-3-((S)-pyrrolidin-2-yl)acrylonitrile; 186

2-((R)-2-((4-amino-3-(2-fluoro-4-phenoxyphenyl)-1H-pyrazolo[3,4-d]pyrimidin-1-yl)methyl)pyrrolidine-1-carbonyl)-3-((R)-pyrrolidin-2-yl)acrylonitrile; 187

(R)-4-amino-N-(1-(4-amino-3-(2-fluoro-4-phenoxyphenyl)-1H-pyrazolo[3,4-d]-pyrimidin-1-yl)propan-2-yl)-2-cyano-4-methylpent-2-enamide; 188A (S)-4-amino-N-(1-(4-amino-3-(2-fluoro-4-phenoxyphenyl)-1H-pyrazolo[3,4-d]-pyrimidin-1-yl)propan-2-yl)-2-cyano-4-methylpent-2-enamide; 188B N-(2-(4-amino-3-(4-phenoxyphenyl)-1H-pyrazolo[3,4-d]pyrimidin-1-yl)ethyl)-2-cyano-3-cyclopropyl-N-methyl-acrylamide; 189

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile; 190A (S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile; 190B (S)—N-(1-(4-amino-3-(2-fluoro-4-phenoxyphenyl)-1H-pyrazolo[3,4-d]pyrimidin-1-yl)propan-2-yl)-2-cyano-4,4-dimethylpent-2-enamide; 191

(S)—N-(1-(4-amino-3-(2-fluoro-4-phenoxyphenyl)-1H-pyrazolo[3,4-d]pyrimidin-1-yl)propan-2-yl)-2-cyano-4-methylpent-2-enamide; 192

(S)—N-(1-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide; 193

(S)—N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide; 194

(S)-4-amino-N-(1-(4-amino-3-(2-fluoro-4-phenoxyphenyl)-1H-pyrazolo[3,4-d]-pyrimidin-1-yl)propan-2-yl)-2-cyano-4-methylpent-2-enamide; 195 or (S)—N-(1-(4-amino-3-(2-fluoro-4-phenoxyphenyl)-1H-pyrazolo[3,4-d]pyrimidin-1-yl)propan-2-yl)-2-cyano-3-cyclopropylacrylamide; 196 or R and S mixtures thereof;
or an individual (E) or (Z) isomer thereof;
and/or a pharmaceutically acceptable salt thereof.

In another embodiment, the BTK inhibitor is chosen from:

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile;

(R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(R)-4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-ethoxy-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-morpholinopent-2-enenitrile; or (R)-2-(3-(4-amino-3-(2,3-difluoro-4-phenoxyphenyl)-1H-pyrazolo[3,4-d]pyrimidin-1-yl)piperidine-1-carbonyl)-4-methyl-4-morpholinopent-2-enenitrile;

or an R and S mixture thereof;
or an individual (E) or (Z) isomer thereof;
and/or a pharmaceutically acceptable salt thereof.

In yet another embodiment, the compound BTK inhibitor is chosen from:

(R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(S)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;

or R and S mixtures thereof;
or an individual (E) or (Z) isomer thereof;
and/or a pharmaceutically acceptable salt thereof.

In yet another embodiment the BTK inhibitor is chosen from:

(R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(S)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;

or an R and S mixture thereof;
or an individual (E) or (Z) isomer thereof;
and/or a pharmaceutically acceptable salt thereof.

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., or from about 0° C. to about 125° C. or at about room (or ambient) temperature, e.g., about 20° C.

Compounds of Formula (I) where $Z^1$ is nitrogen, $Z^2$ is carbon or nitrogen and $Z^3$ is carbon Ar, $R^3$, $R^4$, $R^5$, $R^6$, $R^7$, Z, $R^b$ and $R^c$ are as defined above can be prepared as illustrated and described in Scheme A below.

Scheme A

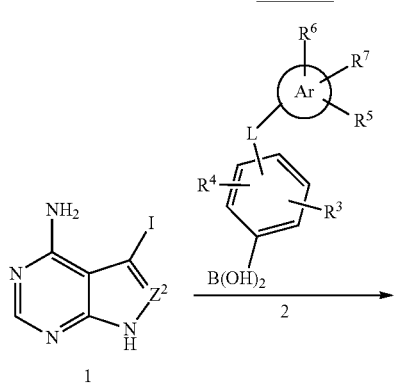

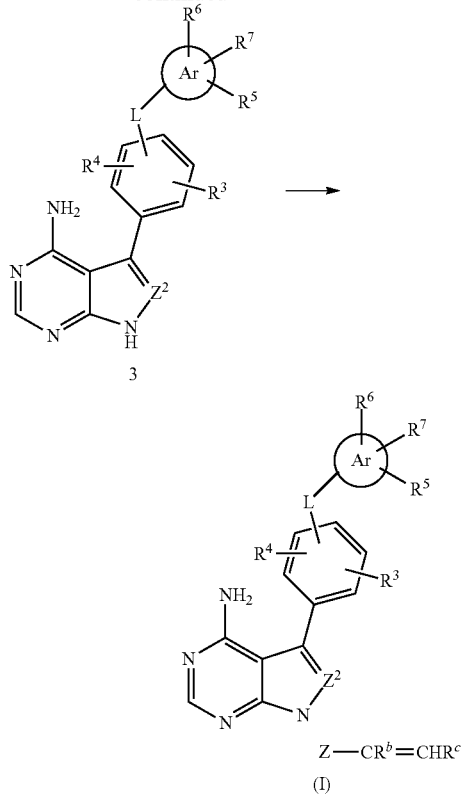

Coupling of an iodo compound of formula 1 where with a boronic acid compound of formula 2 or boronate esters thereof Ar, $R^1$, $R^3$, $R^4$, $R^5$, $R^6$, $R^7$, L, and Ar are as defined above under Suzuki coupling reaction conditions provides a compound of formula 3. The Suzuki coupling reaction can be carried out in organic solvents (such as toluene, benzene, N,N-dimethylformamide (DMF), tetrahydrofuran, methanol, ethanol, acetonitrile, dimethoxyethane, acetone and the like) or water in the presence of base (such as sodium ethylate, sodium hydroxide, potassium hydroxide, sodium bicarbonate, potassium bicarbonate, potassium carbonate, sodium carbonate, triethylamine, and the like) and a palladium catalyst (such as tetrakis(triphenylphosphine)palladium, dichlorobis(triphenyl-phosphine)palladium, palladium acetate, and the like). The reaction is carried out at room temperature to 120° C. Compounds of formula 1 are either commercially available or can be readily prepared by methods well known in the art.

Treatment of a compound of formula 3 with a compound of formula $R^1$-LG where LG is a suitable leaving group such as halo, tosylate, mesylate, triflate, and the like provides a compound of Formula (I). The alkylation or arylation reaction is typically carried out in the presence of a base such as sodium hydride or potassium tert-butoxide, potassium carbonate, and the like, and a catalyst such as 18-crown-6 in a suitable solvent such as N-methylpyrolidone, dimethylformamide, tetrahydrofuran, toluene, and the like.

It will be recognized by a person skilled in the art that precursors to —Z—$CR^b$=$CHR^c$ group can be substituted at any step in the synthetic procedure illustrated in Scheme A above and converted to —Z—$CR^b$=$CHR^c$ group as defined above at alternate stages in the synthetic process based on feasibility of the transformations. Some such examples are described below:

Substitution of precursors to —Z—CR$^b$=CHR$^c$ in the synthesis of compounds of Formula (I) when —Z—CR$^b$=CHR$^c$ is —Z—C(CN)=CHR$^c$ where Z is

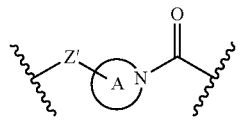

is illustrated and described in Method (a) below.

Method (a):

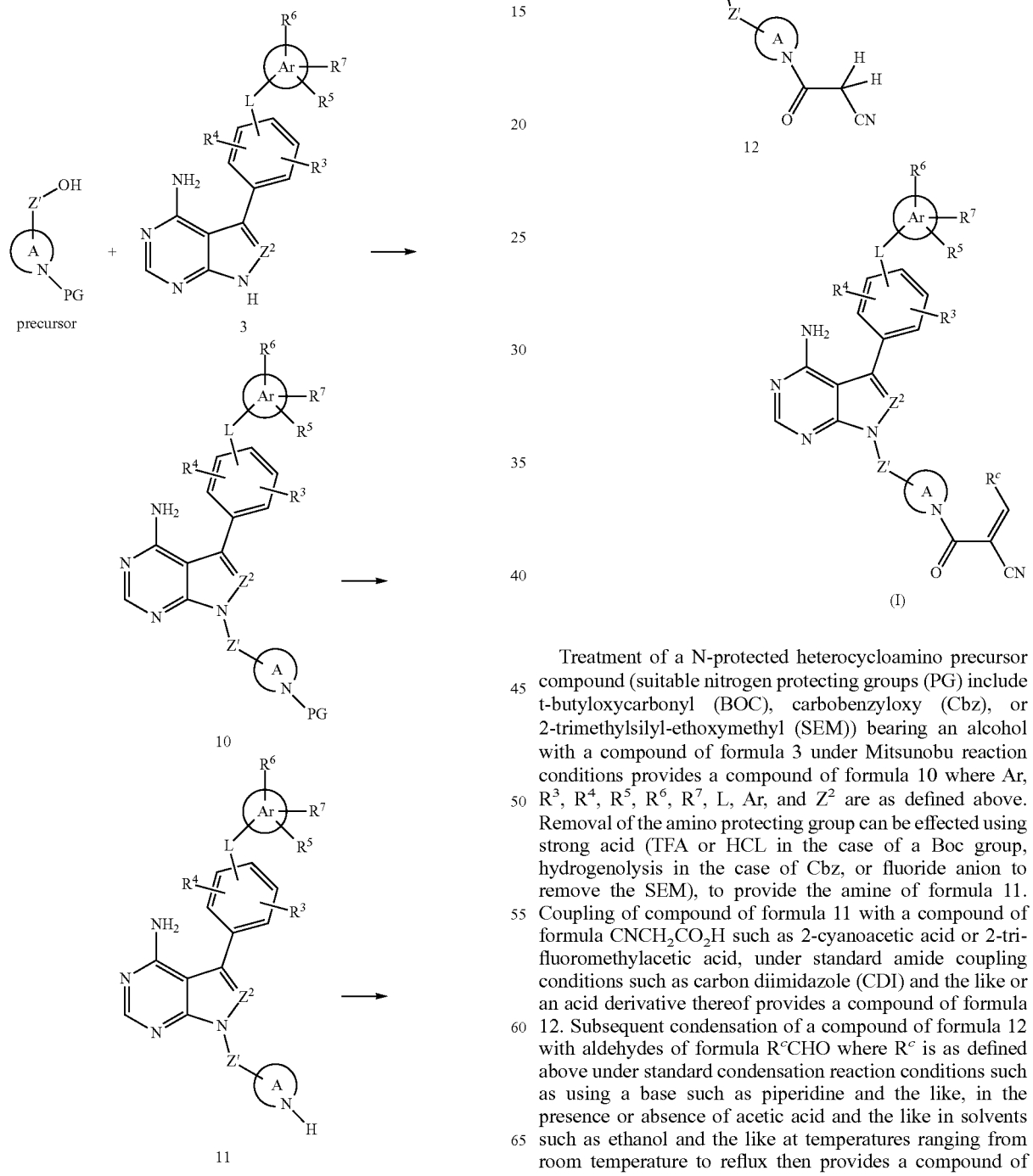

Treatment of a N-protected heterocycloamino precursor compound (suitable nitrogen protecting groups (PG) include t-butyloxycarbonyl (BOC), carbobenzyloxy (Cbz), or 2-trimethylsilyl-ethoxymethyl (SEM)) bearing an alcohol with a compound of formula 3 under Mitsunobu reaction conditions provides a compound of formula 10 where Ar, $R^3$, $R^4$, $R^5$, $R^6$, $R^7$, L, Ar, and $Z^2$ are as defined above. Removal of the amino protecting group can be effected using strong acid (TFA or HCL in the case of a Boc group, hydrogenolysis in the case of Cbz, or fluoride anion to remove the SEM), to provide the amine of formula 11. Coupling of compound of formula 11 with a compound of formula CNCH$_2$CO$_2$H such as 2-cyanoacetic acid or 2-trifluoromethylacetic acid, under standard amide coupling conditions such as carbon diimidazole (CDI) and the like or an acid derivative thereof provides a compound of formula 12. Subsequent condensation of a compound of formula 12 with aldehydes of formula R$^c$CHO where R$^c$ is as defined above under standard condensation reaction conditions such as using a base such as piperidine and the like, in the presence or absence of acetic acid and the like in solvents such as ethanol and the like at temperatures ranging from room temperature to reflux then provides a compound of Formula (I). Aldehydes of formula R$^c$CHO are either commercially available or they can be prepared by methods know in the art. For example tert-butylaldehyde, isopropylaldehyde and cyclopropylaldehyde are commerically available. Compounds of Formula (I) where $R^c$—$C(CH_3)_2NH_2$, and —$C(CH_3)_2NHCH_3$ can be prepared by reacting a compound of formula 12 with an aldehyde of formula BocNHC($CH_3)_2$CHO and BocN($CH_3$)C($CH_3)_2$CHO respectively, followed by removal of the Boc group. Aldehydes of formula BocNHC($CH_3)_2$CHO can be prepared as shown below:

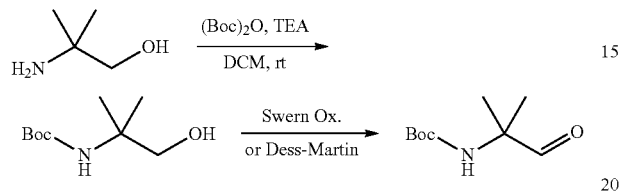

Treatment of 2-amino-2-methylpropan-1-ol with (Boc)$_2$O in the presence of organic amine provides the corresponding 2-BocNH-2-methylpropan-1-ol which upon reaction with a suitable oxidizing agent provide the desired aldehyde of formula 2-BocNH-2-methylpropanaldehyde.

Aldehydes of formula BocN(CH$_3$)C(CH$_3$)$_2$CHO can be prepared as shown below:

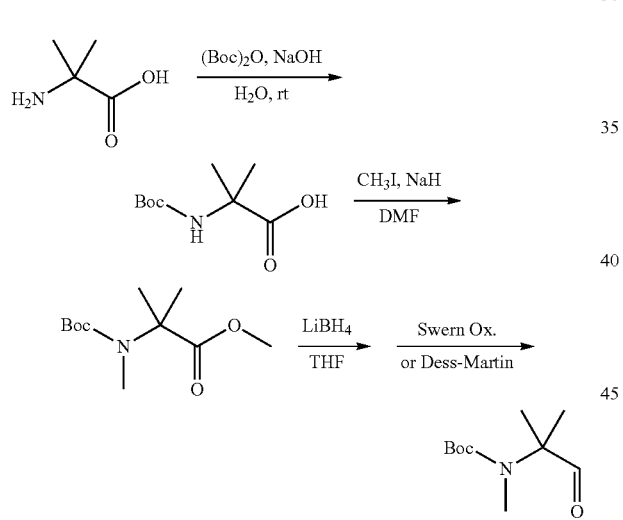

Treatment of 2-amino-2-methylpropanoic with (Boc)$_2$O in the presence of organic amine provides the corresponding 2-BocNH-2-methylpropanoic which upon reaction with an alkylating agent such as methyl iodide in the presence of sodium hydride provide 2-BocN(CH$_3$)-2-methylpropanoic ester. Reduction of the ester group in BocN(CH$_3$)-2-methylpropanoic ester with a suitable reducing agent provides the corresponding alcohol which is then covered to the desired aldehyde as described previously.

Compounds of Formula (I) where $Z^1$ and $Z^3$ are nitrogen and $Z^2$ is carbon, Ar, $R^3$, $R^4$, $R^6$, $R^7$, L, Z, $R^b$ and $R^c$ are as defined above and $R^5$ is hydrogen, alkyl, hydroxy, alkoxy, halo, haloalkyl, or haloalkoxy can be prepared as illustrated and described in Scheme B below.

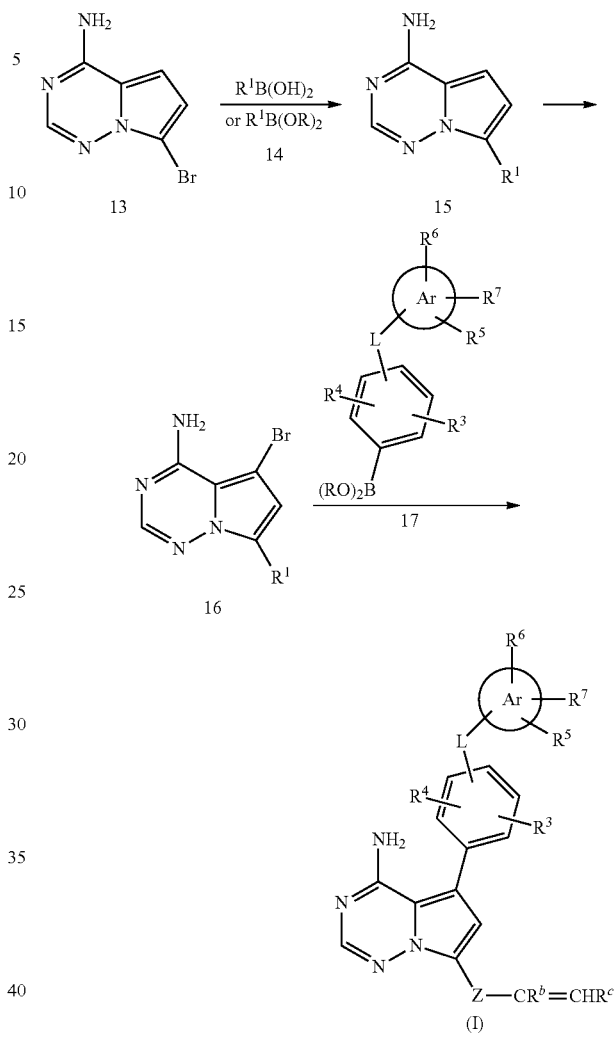

Cross coupling (Suzuki) of a compound of formula 13 (available commercially) with an appropriately substituted boronic acid or boronate esters of formula 13 (as described in Scheme A) provides a compound of formula 15 where $R^1$ is as defined above. Halogenation of compound 15 with a suitable halogenating agent such as N-bromosuccinamide, bromine, and the like, in an organic solvent (such as DMF, dichloromethane, tetrahydrofuran, toluene, acetic acid, water and the like) at temperatures ranging from −78° C. to reflux temperature provides a compound of formula 16. Compound 16 is then coupled with a compound of formula 17 under Suzuki coupling reaction conditions to provide a compound of Formula (I).

It will be recognized by a person skilled in the art that precursors to $R^1$ can be substituted at any step in Scheme 2 above where $R^1$ exists and converted to $R^1$ at alternate stages in the synthetic process based on feasibility of the transformations. Some such transformations are described below:

Substitution of precursors to —Z—$CR^b$=$CHR^c$ in the synthesis of compounds of Formula (I) when —Z—$CR^b$=$CHR^c$ is —Z—C(CN)=$CHR^c$ where Z is

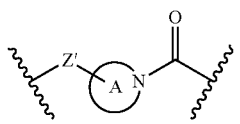

where Z' is bond, is illustrated and described in method (b) below. Standard protecting group (PG) strategies employed by those skilled in the art can be employed as required.

Method (b):

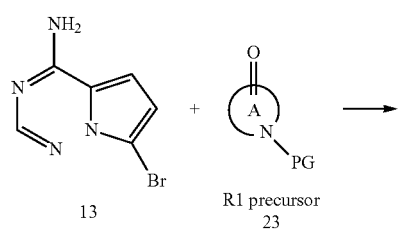

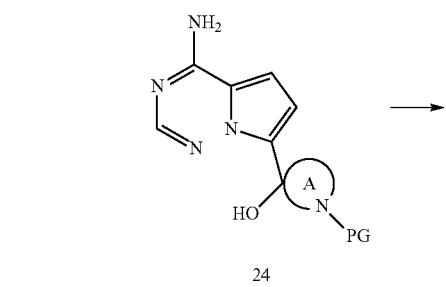

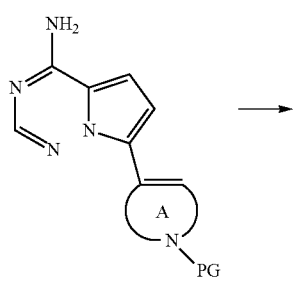

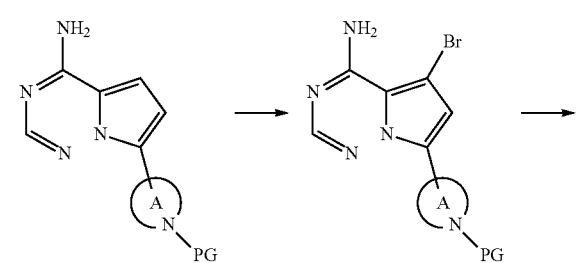

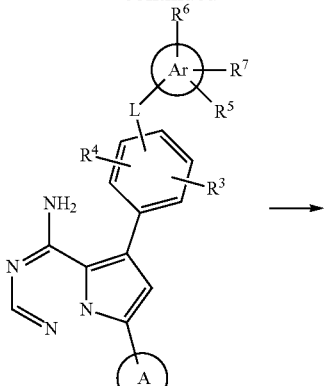

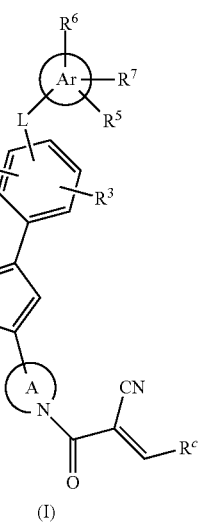

Treatment of compound 13 with trimethylsilyl chloride in solvents such as tetrahydrofuran (THF) at temperatures ranging from 0° C. to room temperature prior to treatment by a Grignard reaction (for example by treatment with isopropyl magnesium chloride in THF at temperatures ranging from 0° C. to room temperature) and subsequent addition of precursor compound of formula 23 bearing a ketone moiety where PG is a suitable protecting group such as tert-butoxycarbonyl (Boc), benzyl (Bn) or 2-trimethylsilyl-ethoxymethyl (SEM)), provides a compound of formula 24 which is converted to a compound of formula 25 under dehydration reaction conditions e.g., treatment of compound 24 with acids such as trifluoroacetic anhydride or trifluoroacetic acid, and the like, in solvents such as pyridine, toluene, methanol, and the like and temperatures ranging from −20° C. to reflux. Reduction of the double bond in the compound of formula 25 with a suitable hydrogenation reaction conditions e.g., with platinum oxide or palladium hydroxide or palladium on carbon in alcoholic solvents such as methanol or ethanol, and the like in the presence or absence of acetic acid and under a hydrogen atmosphere provides a compound of formula 26.

Halogenation of a compound of formula 26 with a suitable halogenating agent as described in scheme B above provides a compound of formula 27 which can then be converted to a compound of Formula (I) as described in method (a) above.

The compounds of this disclosure will be administered in a topical formulation which can be liquids, suspension, emulsions, and the like, and can be prepared by methods well known in the art. The formulation will contain, on a weight percent (wt %) basis, from about 0.01-99.99 wt % of a compound of the present disclosure such as Formula (I) based on the total formulation, with the balance being one or more suitable pharmaceutical excipients amd can be administered in single or multiple doses. Suitable excipients include polymers, surfactants, buffering or pH adjusting agents, tonicity or osmotic adjusting agent(s), preservatives, and/or dispersing agents.

Suitable polymers include hydroxyalkyl celluloses and polyalkylene glycols e.g., hydroxypropylmethyl cellulose, hydroxyethylmethyl cellulose, hydroxypropyl cellulose, carboxymethyl cellulose, alginates, and the like. Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Other surfactants include polyoxyethylene fatty acid glycerides and vegetable oils, e.g., polyoxyethylene (60) hydrogenated castor oil; polyoxyethylene alkylethers and alkylphenyl ethers, e.g. octoxynol 10, octoxynol 40; or cyclodextrins such as α-cyclodextrin, β-cyclodextrin, 2-hydroxyl-β-cyclodextrin, methylated β-cyclodextrin, sulfobutyl ether β-cyclodextrin, hydroxypropyl β-cyclodextrin, and the like. pH Adjusting agent(s) include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate, borates, ammonium chloride, and the like. Such acids, bases and buffers are included in an amount required to maintain pH of the composition in an acceptable range. Preservatives are added to inhibit microbial activity and include mercury-containing substances such as merfen and thiomersal; stabilized chlorine dioxide; and quaternary ammonium compounds such as benzalkonium chloride, cetyltrimethylammonium bromide and cetylpyridinium chloride. Tonicity or osmotic adjusting agent include mannitol, sorbitol, dextrose, sucrose, urea, glycerol, and mixtures thereof; ionic salt selected from the group consisting of alkali metal halides sodium chloride, potassium chloride, zinc chloride, calcium chloride, and mixtures thereof. In certain embodiments, the formulations may also include dispersing agents and/or viscosity modulating agents. Dispersing agents and/or viscosity modulating agents include materials that control the diffusion and homogeneity of a drug through liquid media. Exemplary diffusion facilitators/dispersing agents include, e.g., hydrophilic polymers, electrolytes, Tween®60 or 80, PEG, polyvinylpyrrolidone (PVP; commercially known as Plasdone®), and the carbohydrate-based dispersing agents such as, for example, hydroxypropyl celluloses (e.g., HPC, H-PC-SL, and HPC-L), hydroxypropyl methylcelluloses (e.g., HPMC K100, RPMC K4M, HPMC K15M, and HPMC K100M), carboxymethylcellulose sodium, methylcellulose, hydroxyethyl-cellulose, hydroxypropyl-cellulose, hydroxypropyl-methylcellulose phthalate, hydroxypropyl-methylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®., and F10®8, which are block copolymers of ethylene oxide and propylene oxide); and poloxamines (e.g., Tetronic 908®, also known as Poloxamine 908®, which is a tetrafonctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. In certain embodiments, the formulations may also include one or more viscosity enhancing agents which include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol alginates, acacia, chitosans and combinations thereof.

Any of the well-known techniques and excipients may be used as suitable and as understood in the art can be used to prepare the topical formulations, see for example, Remington: The Science and Practice of Pharmacy, Nineteenth Ed., (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), which are herein incorporated by reference in their entirety.

EXAMPLES

The following preparations of compounds of Formula (I) intermediates (References) are given to enable those skilled in the art to more clearly understand and to practice the present disclosure. They should not be considered as limiting the scope of the disclosure, but merely as being illustrative and representative thereof. The ⁓ line at the alkene carbon, in the compounds below denotes that the compounds are isolated as an undefined mixture of (E) and (Z) isomers.

Example 1

Synthesis of (R)-2-(3-(4-amino-3-(4-phenoxyphenyl)-1H-pyrazolo[3,4-d]pyrimidin-1-yl)piperidine-1-carbonyl)-3-cyclopropylacrylonitrile

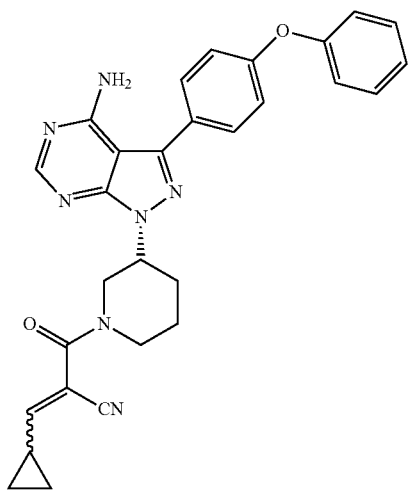

Step 1

A solution of 5-amino-1H-pyrazole-4-carbonitrile (10 g, 92.51 mmol, 1.00 equiv) in formamide (80 mL) was stirred under nitrogen at 165° C. for 5 h. The reaction mixture was cooled to room temperature and the solid was collected by filtration. The filter cake was washed first with 20 mL of water then 20 mL of methanol and dried to yield 9.5 g (76%) of 1H-pyrazolo[3,4-d]pyrimidin-4-amine as a white solid.

Step 2

A mixture of 1H-pyrazolo[3,4-d]pyrimidin-4-amine (150 g, 1.11 mol, 1.00 equiv) and N-iodo-succinimide (375 g, 1.67 mol, 1.58 equiv) in N,N-dimethylformamide (2.5 L) was stirred at 80° C. for 5 h. The reaction mixture was cooled to room temperature and then diluted with 10 L of water. The solid was collected by filtration, washed with 2×1 L of saturated aqueous sodium sulfite and dried under vacuum to give 150 g (52%) of 3-iodo-1H-pyrazolo[3,4-d]pyrimidin-4-amine as a yellow solid.

Step 3

To a stirred mixture of 3-iodo-1H-pyrazolo[3,4-d]pyrimidin-4-amine (5.9 g, 22.6 mmol, 1.00 equiv), (S)-tert-butyl 3-hydroxypiperidine-1-carboxylate (10 g, 50 mmol, 2.2 equiv) and triphenylphosphine (11.8 g, 45 mmol, 2.0 equiv) in tetrahydrofuran (300 mL) at 10° C. was added a solution of diisopropyl azodicarboxylate in tetrahydrofuran (30 mL) dropwise in 30 min. The resulting mixture was stirred at room temperature for 12 h and then concentrated under vacuum. The residue was purified on a silica gel column eluted with dichloromethane/methanol (100/1) to give 3 g (33%) of (R)-tert-butyl 3-(4-amino-3-iodo-1H-pyrazolo[3,4-d]pyrimidin-1-yl)piperidine-1-carboxylate as a yellow solid.

Step 4

A mixture of tert-butyl 3-[4-amino-3-iodo-1H-pyrazolo[3,4-d]pyrimidin-1-yl]piperidine-1-carboxylate (1 g, 2.25 mmol, 1.00 equiv), (4-phenoxyphenyl)boronic acid (530 mg, 2.48 mmol, 1.10 equiv), sodium carbonate (480 mg, 4.53 mmol, 2.01 equiv) and tetrakis(triphenylphosphine)palladium (78 mg, 0.07 mmol, 0.03 equiv) in 1,4-dioxane (60 mL) and water (15 mL) was stirred under nitrogen at 90° C. for 24 h. The reaction mixture was cooled to room temperature and then concentrated under vacuum. The residue was dissolved in 500 mL of dichloromethane. The resulting solution was washed with 200 mL of water, dried over anhydrous sodium sulfate and concentrated under vacuum. The residue was purified on a silica gel column eluted with dichloromethane/methanol (100/1) to give 700 mg (64%) of tert-butyl 3-[4-amino-3-(4-phenoxyphenyl)-1H-pyrazolo[3,4-d]pyrimidin-1-yl]piperidine-1-carboxylate as a yellow solid.

Step 5

A mixture of tert-butyl 3-[4-amino-3-(4-phenoxyphenyl)-1H-pyrazolo[3,4-d]pyrimidin-1-yl]piperidine-1-carboxylate (700 mg, 1.44 mmol, 1.00 equiv) in dichloromethane (100 mL) and trifluoroacetic acid (20 mL) was stirred at room temperature for 12 h. The reaction mixture was concentrated under vacuum to yield 580 mg of crude 3-(4-phenoxyphenyl)-1-(piperidin-3-yl)-1H-pyrazolo[3,4-d]pyrimidin-4-amine as a yellow oil.

Step 6

A mixture of 3-(4-phenoxyphenyl)-1-(piperidin-3-yl)-1H-pyrazolo[3,4-d]pyrimidin-4-amine (580 mg, 1.50 mmol, 1.00 equiv), carbonyldiimidazole (365 mg, 2.25 mmol, 1.50 equiv) and 2-cyanoacetic acid (190 mg, 2.24 mmol, 1.49 equiv) in dichloromethane (100 mL) was stirred at room temperature for 24 h. The reaction mixture was diluted with 100 mL of dichloromethane and washed with 3×100 mL of saturated aqueous ammonium chloride solution. The organic layer was dried over anhydrous sodium sulfate and concentrated under vacuum. The residue was purified on a silica gel column eluted with dichloromethane/methanol (100/1) to give 380 mg (56%) of 3-[3-[4-amino-3-(4-phenoxyphenyl)-1H-pyrazolo[3,4-d]pyrimidin-1-yl]piperidin-1-yl]-3-oxopropanenitrile as a white solid.

Step 7

A mixture of 3-[3-[4-amino-3-(4-phenoxyphenyl)-1H-pyrazolo[3,4-d]pyrimidin-1-yl]piperidin-1-yl]-3-oxopropanenitrile (120 mg, 0.26 mmol, 1.00 equiv), piperidine (27 mg, 0.28 mmol, 1.07 equiv) and cyclopropanecarbaldehyde (28 mg, 0.40 mmol, 1.51 equiv) in methanol (8 mL) was stirred in sealed tube at room temperature for 24 h. The resulting mixture was concentrated under vacuum and the residue was purified on a silica gel column eluted with dichloromethane/methanol (100/1) to give 85.4 mg (64%) of the title compound as a white solid. MS (ESI, pos. ion) m/z: 506 (M+1). $^1$HNMR (300 MHz, CDCl$_3$, ppm) 8.392 (1H, s), 7.676~7.581 (2H, t), 7.445~7.393 (2H, t), 7.202~7.097 (5H, m), —6.601~6.566 (1H, d, J=10.5), 5.737 (2H, s), 5.010~4.912 (1H, m), 4.691~3.185 (4H, m), 2.464~2.035 (5H, m), 1.275~0.876 (4H, m).

Example 2

Synthesis of 2-((R)-3-(4-amino-3-(4-(3,4-dichlorophenoxy)-3-methoxyphenyl)-1H-pyrazolo[3,4-d]pyrimidin-1-yl)piperidine-1-carbonyl)-3-cyclopropylacrylonitrile

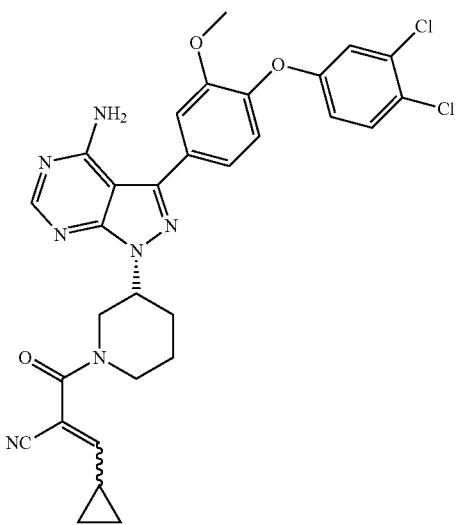

Step 1

A mixture of 3,4-dichlorophenol (38 g, 233.13 mmol, 1.00 equiv), 1-fluoro-2-methoxy-4-nitrobenzene (40 g, 233.75 mmol, 1.00 equiv) and potassium carbonate (64 g, 463.77 mmol, 1.99 equiv) in N,N-dimethylformamide (250 mL) was stirred overnight at 60° C. The resulting solution was diluted with 1000 mL of water, extracted with 3×200 mL of ethyl acetate and the organic layers combined. The resulting mixture was washed with 3×500 mL of brine. The mixture was dried over anhydrous sodium sulfate and concentrated under vacuum to yield 60 g (82%) of 1,2-dichloro-4-(2-methoxy-4-nitrophenoxy)benzene as a brown solid.

Step 2

A mixture of 1,2-dichloro-4-(2-methoxy-4-nitrophenoxy)benzene (60 g, 190.40 mmol, 1.00 equiv), Fe (53 g, 946.43 mmol, 4.97 equiv) and ammonium chloride (10 g, 188.68 mmol, 0.99 equiv) in tetrahydrofuran/water (1/2) (600 mL) was stirred overnight at 60° C. under an inert atmosphere of nitrogen. The mixture was filtered through Celite and the filtrate was concentrated under vacuum. The resulting solution was extracted with 3×500 mL of dichloromethane and the organic layers combined. The resulting mixture was washed with 3×500 mL of brine. The mixture was dried over anhydrous magnesium sulfate and concentrated under vacuum to give 40 g (74%) of 4-(3,4-dichlorophenoxy)-3-methoxyaniline as a light gray solid.

Step 3

A solution of sodium nitrite (14.4 g, 208.70 mmol, 1.98 equiv) in water (500 mL) was added dropwise into a solution of 4-(3,4-dichlorophenoxy)-3-methoxyaniline (30 g, 105.58 mmol, 1.00 equiv) in sulfuric acid (1000 mL) with stirring at 0° C. and the mixture was stirred for 30 min at 0° C. The above mixture was added dropwise to a solution of potassium iodide (1000 mL, 5%) in water with stirring at 50° C. The reaction was completed immediately. The reaction mixture was cooled to room temperature, extracted with 3×500 mL of ethyl acetate and the organic layers combined. The resulting mixture was washed with 3×500 mL of saturated aqueous sodium bicarbonate and 3×500 mL of brine. The mixture was dried over anhydrous sodium sulfate and concentrated under vacuum to give 24 g (crude) of 1,2-dichloro-4-(4-iodo-2-methoxyphenoxy)benzene as red oil.

Step 4

A mixture of 1,2-dichloro-4-(4-iodo-2-methoxyphenoxy)benzene (93 g, 235.43 mmol, 1.00 equiv) in 1,4-dioxane (500 mL), potassium acetate (46 g, 469.39 mmol, 1.99 equiv), 4,4,5,5-tetramethyl-2-(4,4,5,5-tetramethyl-1,3,2-dioxaborolan-2-yl)-1,3,2-dioxaborolane (89 g, 350.39 mmol, 1.49 equiv) and Pd(dppf)Cl$_2$ (4.65 g) was stirred overnight at 90° C. under an inert atmosphere of nitrogen. The reaction mixture was cooled to room temperature and concentrated under vacuum. The residue was dissolved in 500 mL of ethyl acetate and washed with mL of water and brine. The mixture was dried over anhydrous sodium sulfate and concentrated under vacuum. The residue was applied onto a silica gel column with ethyl acetate/petroleum ether (1/100) to yield 10 g (11%) of 2-[4-(3,4-dichlorophenoxy)-3-methoxyphenyl]-4,4,5,5-tetramethyl-1,3,2-dioxaborolane as light yellow oil.

2-[4-(3,4-Dichlorophenoxy)-3-methoxyphenyl]-4,4,5,5-tetramethyl-1,3,2-dioxaborolane was then covered to the title compound following the procedures described in Example 1, steps 4-7 above.

Example 3

Synthesis of (R)-2-(3-(4-amino-3-(4-phenoxyphenyl)-1H-pyrazolo[3,4-d]pyrimidin-1-yl)piperidine-1-carbonyl)-4,4-dimethylpent-2-enenitrile

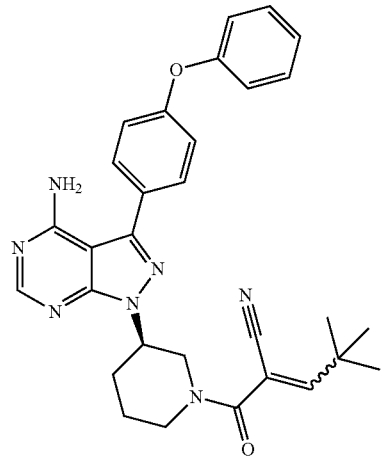 [SMILES: CC(C)(C)C=C(C#N)C(=O)N1CCC[C@@H](n2nc(-c3ccc(Oc4ccccc4)cc3)c3c(N)ncnc32)C1]

A mixture of 3-[3-[4-amino-3-(4-phenoxyphenyl)-1H-pyrazolo[3,4-d]pyrimidin-1-yl]piperidin-1-yl]-3-oxopropanenitrile (150 mg, 0.33 mmol, 1.00 equiv), methanol (15 mL), dichloromethane (5 mL), piperidine (56 mg, 0.66 mmol, 2 equiv) and pivaldehyde (142 mg, 1.66 mmol, 5 equiv) was stirred for 48 h at 30° C. in a 25-mL sealed tube. The resulting mixture was concentrated under vacuum. The residue was applied onto a silica gel column with dichloromethane/methanol (100/1) to give 45 mg (26%) of (R)-2-(3-(4-amino-3-(4-phenoxyphenyl)-1H-pyrazolo[3,4-d]pyrimidin-1-yl)piperidine-1-carbonyl)-4,4-dimethylpent-2-enenitrile as a white solid. MS (ESI, pos. ion) m/z: 522

(M+1) ¹HNMR (300 MHz, CDCl₃, ppm) 8.396 (1H, s), 7.684~7.656 (2H, d, J=8.4), 7.440~7.388 (2H, t), 7.222~7.092 (5H, m), 6.956 (1H, s), 5.613 (2H, s), 5.006~4.909 (1H, m), 4.626~3.290 (4H, m), 2.419~1.732 (4H, m), 1.275 (9H, s).

Example 4

Synthesis of 2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile

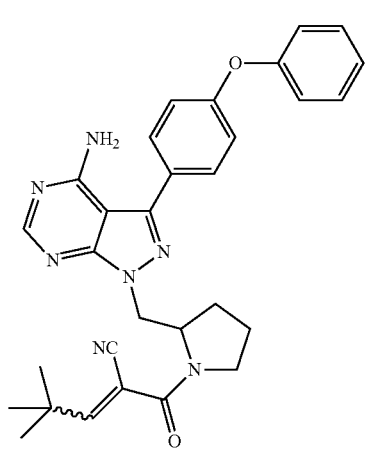 [SMILES: CC(C)(C)C=C(C#N)C(=O)N1CCCC1Cn1nc(-c2ccc(Oc3ccccc3)cc2)c2c(N)ncnc21]

Synthesized as Examples 1 and 3 above but using tert-butyl 2-(hydroxymethyl)-pyrrolidine-1-carboxylate instead of (S)-tert-butyl-3-hydroxypiperidine-1-carboxylate. MS (ESI, pos. ion) m/z: 522 (M+1).

Example 5

Synthesis of (N-((1r,4r)-4-(4-amino-3-(4-phenoxyphenyl)-1H-pyrazolo[3,4-d]pyrimidin-1-yl)cyclohexyl)-2-cyano-3-cyclopropylacrylamide

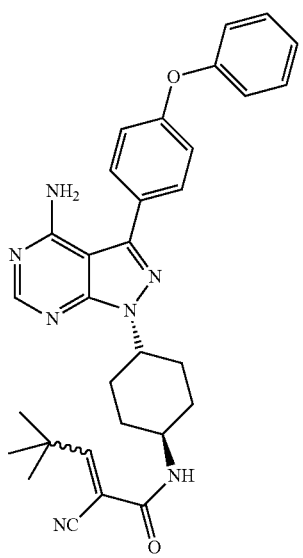

Synthesized as described in Examples 1 and 3 above except using tert-butyl(1r,4r)-4-hydroxycyclohexylcarbamate instead of (S)-tert-butyl3-hydroxypiperidine-1-carboxylate. MS (ESI, pos. ion) m/z: 536 (M+1).

Example 6

Synthesis of 2-(4-(4-amino-3-(4-phenoxyphenyl)-1H-pyrazolo[3,4-d]pyrimidin-1-yl)piperidine-1-carbonyl)-4,4-dimethylpent-2-enenitrile

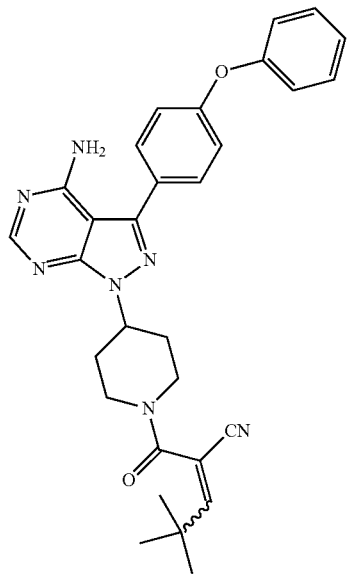 [SMILES: CC(C)(C)C=C(C#N)C(=O)N1CCC(n2nc(-c3ccc(Oc4ccccc4)cc3)c3c(N)ncnc32)CC1]

Synthesized as described in Examples 1 and 3 above except using, tert-butyl-4-hydroxypiperidine-1-carboxylate instead of (S)-tert-butyl3-hydroxypiperidine-1-carboxylate. MS (ESI, pos. ion) m/z: 522 (M+1).

Example 8

Synthesis of (R)-2-(3-(4-amino-3-(4-(3,4-dichlorophenoxy)-3-methoxyphenyl)-1H-pyrazolo-[3,4-d]pyrimidin-1-yl)piperidine-1-carbonyl)-4,4-dimethylpent-2-enenitrile

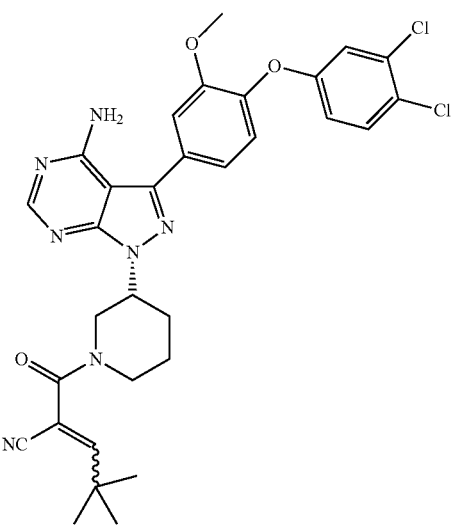

Synthesized as described in Examples 7 and 3 above using pivaldehyde instead of cyclopropanecarbaldehyde. MS (ESI, pos. ion) m/z: 620 (M+1).

Example 9

Synthesis of (R)—N-(4-(4-amino-1-(1-(2-cyano-3-cyclopropylacryloyl)piperidin-3-yl)-1H-pyrazolo[3,4-d]pyrimidin-3-yl)phenyl)-4-(trifluoromethyl)benzamide

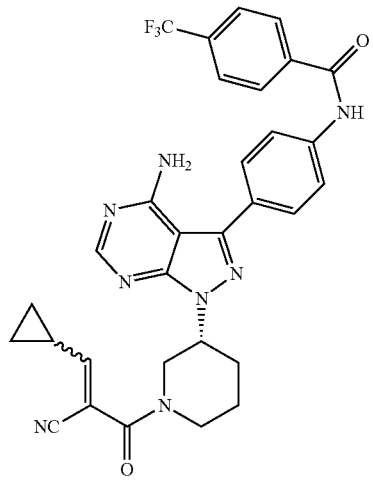 [SMILES: N#CC(=CC1CC1)C(=O)N1CCC[C@@H](n2nc(-c3ccc(NC(=O)c4ccc(C(F)(F)F)cc4)cc3)c3c(N)ncnc32)C1]

Step 1

A mixture of 3-iodo-1H-pyrazolo[3,4-d]pyrimidin-4-amine (5.9 g, 22.6 mmol, 1.00 equiv), (S)-tert-butyl3-hydroxypiperidine-1-carboxylate (10 g, 50 mmol, 2.2 equiv), triphenylphosphine (11.8 g, 45 mmol, 2 equiv) in tetrahydrofuran (300 mL) was stirred at 10° C. Diisopropyl azodicarboxylate in tetrahydrofuran (30 mL) was dropped in the mixture slowly in 30 min. The resulting mixture was stirred for 12 h at room temperature was and then concentrated under vacuum. The residue was loaded onto a silica gel column and eluted with dichloromethane/methanol (100/1) to give 3 g (33%) of (R)-tert-butyl 3-(4-amino-3-iodo-1H-pyrazolo[3,4-d]pyrimidin-1-yl)piperidine-1-carboxylate as yellow solid. MS (ESI, pos. ion) m/z: 445 (M+1).

Step 2

Into a 250-mL 3-necked round-bottom flask purged and maintained with an inert atmosphere of nitrogen, was placed (R)-tert-butyl 3-[4-amino-3-iodo-1H-pyrazolo[3,4-d]pyrimidin-1-yl]piperidine-1-carboxylate (2 g, 4.50 mmol, 1.00 equiv), 4-borono-benzenaminium chloride (0.934 g), Pd(PPh$_3$)$_4$ (0.312 g), ethylene glycol dimethyl ether (100 mL), sodium carbonate (1.194 g), and water (20 mL). The resulting solution was stirred for 12 h at 80° C. in an oil bath. The resulting mixture was concentrated under vacuum and residue was loaded onto a silica gel column and eluted with dichloromethane/methanol (50:1) to give 1.5 g (81%) of (R)-tert-butyl 3-(4-amino-3-(4-aminophenyl)-1H-pyrazolo[3,4-d]pyrimidin-1-yl)piperidine-1-carboxylate as a brown solid. MS (ESI, pos. ion) m/z: 410 (M+1)

Step 3

Into a 250-mL round-bottom flask, was placed (R)-tert-butyl 3-[4-amino-3-(4-aminophenyl)-1H-pyrazolo[3,4-d]pyrimidin-1-yl]piperidine-1-carboxylate (1.0 g, 2.44 mmol, 1.00 equiv), HATU (0.746 g), 4-(trifluoromethyl)benzoic acid (374 mg, 1.97 mmol, 0.81 equiv), triethylamine (500 mg, 4.94 mmol, 2.02 equiv), and N,N-dimethylformamide (50 mL). The resulting solution was stirred for 5 h at 25° C. The resulting mixture was quenched with water. The resulting solution was extracted with ethyl acetate and washed with sodium chloride (sat). The organic layers dried over anhydrous magnesium sulfate and concentrated under vacuum and residue was loaded onto a silica gel column and eluted with dichloromethane/methanol (50:1 to give 1.15 g (81%) of tert-butyl 3-[4-amino-3-(4-[[4-(trifluoromethyl)benzene]amido]phenyl)-1H-pyrazolo[3,4-d]pyrimidin-1-yl]piperidine-1-carboxylate as a brown solid. MS (ESI, pos. ion) m/z: 582 (M+1)

Step 4

Into a 250-mL round-bottom flask, was placed (R)-tert-butyl 3-[4-amino-3-(4-[[4-(trifluoromethyl)benzene]amido]phenyl)-1H-pyrazolo[3,4-d]pyrimidin-1-yl]piperidine-1-carboxylate (1.1 g, 1.89 mmol, 1.00 equiv), and dichloromethane (100 mL). This was followed by the addition of CF$_3$COOH (20 mL) dropwise with stirring at 25° C. over 10 min. The resulting solution was stirred for 3 h at 25° C. The resulting mixture was concentrated under vacuum to give 0.829 g (91%) of (R)—N-[4-[4-amino-1-(piperidin-3-yl)-1H-pyrazolo[3,4-d]pyrimidin-3-yl]phenyl]-4-(trifluoromethyl)benzamide as brown oil. MS (ESI, pos. ion) m/z: 382 (M+1)

Step 5

Into a 250-mL round-bottom flask, was placed (R)—N-[4-[4-amino-1-(piperidin-4-yl)-1H-pyrazolo[3,4-d]pyrimidin-3-yl]phenyl]-4-(trifluoromethyl)benzamide (828 mg, 1.72 mmol, 1.00 equiv), 2-cyanoacetic acid (220 mg, 2.59 mmol, 1.50 equiv), CDI (420 mg, 2.59 mmol, 1.51 equiv), in dichloromethane (80 mL). The resulting solution was stirred for 12 h at 25° C. The resulting mixture was washed with NH$_4$Cl and concentrated under vacuum. The residue was loaded onto a silica gel column and eluted with dichloromethane/methanol (50:1) to give 300 mg (32%) of N-(4-[4-amino-1-[1-(2-cyanoacetyl)piperidin-4-yl]-1H-pyrazolo[3,4-d]pyrimidin-3-yl]phenyl)-4-(trifluoromethyl)benzamide as a yellow solid. MS (ESI, pos. ion) m/z: 549 (M+1)

Step 6

Into a 10-mL round-bottom flask, was placed (R)—N-(4-[4-amino-1-[1-(2-cyanoacetyl)piperidin-3-yl]-1H-pyrazolo[3,4-d]pyrimidin-3-yl]phenyl)-4-(trifluoromethyl)-benzamide (65 mg, 0.12 mmol, 1.00 equiv), cyclopropanecarbaldehyde (16.6 mg, 0.24 mmol, 2.00 equiv), piperidine (10 mg, 0.12 mmol, 0.99 equiv), methanol (5 mL). The resulting solution was stirred for 12 h at 25° C. The resulting mixture was concentrated under vacuum and the residue was loaded onto a silica gel column and eluted with dichloromethane/methanol (50:1) to give 43 mg (60%) of (R)—N-[4-(4-amino-1-[1-[2-cyano-2-(cyclopropylmethylidene)acetyl]piperidin-3-yl]-1H-pyrazolo[3,4-d]pyrimidin-3-yl)phenyl]-4-(trifluoromethyl)benzamide as a white solid. MS (ESI, pos. ion) m/z: 601 (M+1), $^1$HNMR (300 MHz, CDCl$_3$, ppm), 8.6 (1H, s), 8.348 (1Hs), 8.065~8.038 (2H, d, J=8.1), 7.880~7.852 (1H, d, J=8.4), 7.768~7.659 (4H, m), 6.532~6.496 (1H, dJ=10.8), 5.949 (2H, s), 4.976~4.907 (1H, m), 4.638~3.218 (4H, m), 2.436~1.818 (5H, m), 1.221~1.198 (2H, m), 0.89~0.772 (2H, m).

Example 10
Preparation of (R)—N-(4-(4-amino-1-(1-(2-cyano-4,4-dimethylpent-2-enoyl)piperidin-3-yl)-1H-pyrazolo[3,4-d]pyrimidin-3-yl)phenyl)-4-(trifluoromethyl)benzamide

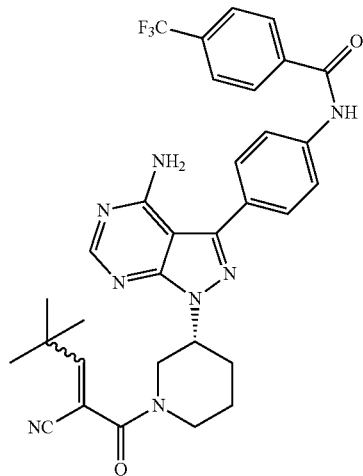 [SMILES: CC(C)(C)C=C(C#N)C(=O)N1CCC[C@@H](n2nc(-c3ccc(NC(=O)c4ccc(C(F)(F)F)cc4)cc3)c3c(N)ncnc32)C1]

Into a 50-mL round-bottom flask, was placed N-(4-[4-amino-1-[1-(2-cyanoacetyl)-piperidin-3-yl]-1H-pyrazolo[3,4-d]pyrimidin-3-yl]phenyl)-4-(trifluoromethyl)benzamide (130 mg, 0.24 mmol, 1.00 equiv), 2,2-dimethylpropanal (2 mL), piperidine (1 mL), and methanol (30 mL). The resulting solution was stirred for 24 h at 30° C. in an oil bath. The resulting mixture was concentrated under vacuum and residue was loaded onto a silica gel column and eluted with dichloromethane/methanol (50/1 to give 40 mg (27%) of N-[4-(4-amino-1-[1-[2-cyano-2-(2,2-dimethylpropylidene)acetyl]piperidin-3-yl]-1H-pyrazolo[3,4-d]pyrimidin-3-yl)phenyl]-4-(trifluoromethyl)benzamide as a white solid. MS (ESI, pos. ion) m/z: 617 (M+1), $^1$HNMR (300 MHz, CDCl$_3$, ppm), 8.364 (1H, s), 8.212 (1H, s), 8.086~8.059 (2H, t), 7.929~7.901 (2H, d, J=8.4), 7.827~7.800 (2H, d, J=8.1), 7.742~7.715 (2H, d, J=8.1), 6.963 (1H, s), 6.3 (2H, s), 5.031~4.934 (1H, m), 4.8~3.05 (4H, m), 2.738~2.067 (5H, m), 1.274 (9H, s).

Example 11
Synthesis of (R)-2-(2-((4-amino-3-(4-(3-fluorophenoxy)phenyl)-1H-pyrazolo[3,4-d]pyrimidin-1-yl)methyl)pyrrolidine-1-carbonyl)-3-cyclopropylacrylonitrile

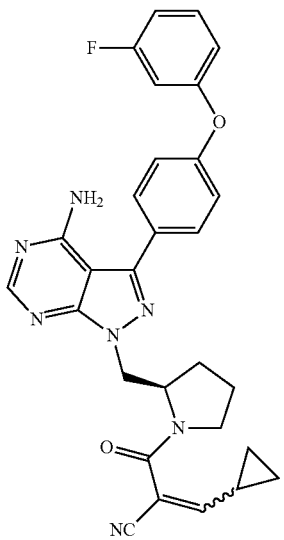 [SMILES: N#CC(=CC1CC1)C(=O)N1CCC[C@@H]1Cn1nc(-c2ccc(Oc3cccc(F)c3)cc2)c2c(N)ncnc21]

Step 1
Into a 100-mL 3-necked round-bottom flask purged and maintained under an inert atmosphere of nitrogen, was placed tert-butyl (2R)-2-([4-amino-3-iodo-1H-pyrazolo[3,4-d]pyrimidin-1-yl]methyl)pyrrolidine-1-carboxylate (300 mg, 0.68 mmol, 1.00 equiv), prepared as described in Example 1 except in the Mitsunobu reaction using (R)-tert-butyl 2-(hydroxymethyl)pyrrolidine-1-carboxylate instead of (S)-tert-butyl 3-hydroxypiperidine-1-carboxylate, 2-[4-(3-fluorophenoxy)phenyl]-4,4,5,5-tetramethyl-1,3,2-dioxaborolane (254 mg, 0.81 mmol, 1.20 equiv), tetrakis(triphenylphosphane)palladium (47 mg, 0.04 mmol, 0.06 equiv), ethylene glycol dimethyl ether (50 mL), sodium carbonate (180 mg, 1.70 mmol, 2.50 equiv), and water (10 mL). The resulting solution was stirred for 12 h at 80° C. in an oil bath. The resulting mixture was concentrated under vacuum and extracted with dichloromethane. The organic layers were combined, dried and concentrated under vacuum. The residue was loaded on a silica gel column and eluted with dichloromethane/methanol (50/1) to give 0.27 g (79%) of tert-butyl (2R)-2-([4-amino-3-[4-(3-fluorophenoxy)phenyl]-1H-pyrazolo[3,4-d]pyrimidin-1-yl]methyl)pyrrolidine-1-carboxylate as a brown solid.

Step 2
Into a 100-mL round-bottom flask, was placed a solution of tert-butyl (2R)-2-([4-amino-3-[4-(3-fluorophenoxy)phenyl]-1H-pyrazolo[3,4-d]pyrimidin-1-yl]methyl)pyrrolidine-1-carboxylate (270 mg, 0.54 mmol, 1.00 equiv) in dichloromethane (50 mL). This was followed by the addition of trifluoroacetic acid (10 mL) dropwise with stirring over 10 min. The resulting solution was stirred for 3 h at 25° C. The resulting mixture was concentrated under vacuum to give 0.216 g (crude) of 3-[4-(3-fluorophenoxy)phenyl]-1-[(2R)-pyrrolidin-2-ylmethyl]-1H-pyrazolo[3,4-d]pyrimidin-4-amine as brown oil.

Step 3
Into a 100-mL round-bottom flask, was placed 3-[4-(3-fluorophenoxy)phenyl]-1-[(2R)-pyrrolidin-2-ylmethyl]-1H-pyrazolo[3,4-d]pyrimidin-4-amine (216 mg, 0.53 mmol, 1.00 equiv), 2-cyanoacetic acid (36.8 mg, 0.43 mmol, 0.80 equiv), HATU (166 mg, 0.44 mmol, 0.80 equiv), triethylamine (109 mg, 1.08 mmol, 2.00 equiv), N,N-dimethylformamide (50 mL). The resulting solution was stirred for 3 h at 25° C. The resulting solution was extracted with ethyl acetate and the organic layers combined and concentrated under vacuum. The residue was loaded on a silica gel column and eluted with dichloromethane methanol (50 l) to give 150 mg (60%) of 3-[(2R)-2-([4-amino-3-[4-(3-fluorophenoxy)phenyl]-1H-pyrazolo[3,4-d]pyrimidin-1-yl]methyl)pyrrolidin-1-yl]-3-oxopropanenitrile as a yellow solid.

Step 4
Into a 10-mL round-bottom flask, was placed 3-[(2R)-2-([4-amino-3-[4-(3-fluorophenoxy)phenyl]-1H-pyrazolo[3,4-d]pyrimidin-1-yl]methyl)pyrrolidin-1-yl]-3-oxopropanenitrile (150 mg, 0.32 mmol, 1.00 equiv), piperidine (27 mg, 0.32 mmol, 1.00 equiv), cyclopropanecarbaldehyde (44.5 mg, 0.63 mmol, 2.00 equiv), methanol (5 mL). The resulting solution was stirred for 12 h at 25° C. and then concentrated under vacuum. The residue was loaded on a silica gel column and eluted with dichloromethane/methanol (50/1) to give 48.5 mg (29%) of the title compound as a off-white solid. LC-MS: (ES, m/z): MS (ESI, pos. ion) m/z: 524 (M+1). H-NMR: (CDCl$_3$, ppm): 1HNMR (300 MHz, CD$_3$OD, ppm), 8.253 (1H, s), 7.686~7.749 (2H, t), 7.363~7.440 (1H, t), 7.185~7.232 (2H, t), 6.833~6.941 (3H, m), 6.450~6.600 (1H, d), 4.301~4.555 (3H, m), 3.604~3.638 (2H, m), 1.868~2.005 (5H, m), 1.200~1.294 (3H, m), 0.798~0.810 (2H, m).

Example 12

Synthesis of (R)-2-(2-((4-amino-3-(4-(2,6-difluorophenoxy)phenyl)-1H-pyrazolo[3,4-d]pyrimidin-1-yl)methyl)pyrrolidine-1-carbonyl)-3-cyclopropylacrylonitrile

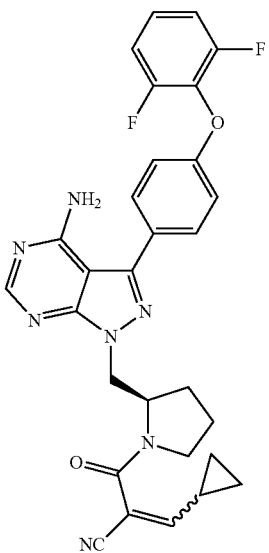 [SMILES: N#CC(=CC1CC1)C(=O)N1CCC[C@@H]1Cn1nc(-c2ccc(Oc3c(F)cccc3F)cc2)c2c(N)ncnc21]

Step 1

Into a 1 L, 2-necked round-bottom flask purged and maintained under an inert atmosphere of nitrogen, was placed 3-iodo-1H-pyrazolo[3,4-d]pyrimidin-4-amine (10 g, 38.31 mmol, 1.00 equiv), tert-butyl (2R)-2-(hydroxymethyl)pyrrolidine-1-carboxylate (15.4 g, 76.52 mmol, 2.00 equiv), PPh$_3$ (20.1 g, 76.63 mmol, 2.00 equiv), and N,N-dimethylformamide (400 mL). DIAD (15.5 g, 76.65 mmol, 2.00 equiv) was added dropwise over 30 min. The resulting solution was stirred for 12 h at 25° C. and then diluted with 1 L of water. The resulting solution was extracted with ethyl acetate and the organic layers combined and washed with brine. The mixture was dried over anhydrous sodium sulfate and concentrated under vacuum and the residue was placed on a silica gel column and eluted with chloroform/methanol (100/1) to give 1.2 g (6%) of tert-butyl (2R)-2-([4-amino-3-iodo-1H-pyrazolo[3,4-d]pyrimidin-1-yl]methyl)pyrrolidine-1-carboxylate as a off-white solid.

Step 2

Into a 500-mL 4-necked round-bottom flask, was placed a solution of sodium hydride (4.05 g, 168.75 mmol, 1.70 equiv) in N,N-dimethylformamide (200 mL). A solution of 1-fluoro-4-nitrobenzene (14 g, 99.22 mmol, 1.00 equiv) in N,N-dimethylformamide (50 mL) was added dropwise with stirring at 0° C. over 20 min. The resulting solution was stirred for 2 hr at room temperature. Cu$_2$Cl$_2$ (9.83 g, 100.31 mmol, 1.01 equiv) was added and a solution of 2,6-difluorophenol (15.5 g, 119.15 mmol, 1.20 equiv) in N,N-dimethylformamide (50 mL) was added dropwise with stirring at 25° C. over 10 min. The resulting solution was stirred for 12 h at 100° C. in an oil bath, diluted with 500 mL of water and extracted with ethyl acetate. The combined organic layers were washed with water and brine, dried over anhydrous sodium sulfate and concentrated under vacuum. The residue was placed on a silica gel column and eluted with ethyl acetate/petroleum ether (1/8) to give 20 g (80%) of 1,3-difluoro-2-(4-nitrophenoxy)benzene as brown oil.

Step 3

Into a 500 mL, 3-necked round-bottom flask purged and maintained under an inert atmosphere of nitrogen, was placed a solution of 1,3-difluoro-2-(4-nitrophenoxy)benzene (20 g, 79.62 mmol, 1.00 equiv) in methanol (200 mL), Raney Nickel (2 g). A solution of hydrazine hydrate (12.67 g) in methanol (50 mL) was added dropwise with stirring in 15 min. The resulting solution was stirred for 12 h at 25° C., then filtrated and the filtrate was concentrated under vacuum. The residue was diluted with f ethyl acetate, washed with water and brine, and dried over anhydrous sodium sulfate and concentrated under vacuum to give 16 g (91%) of 4-(2,6-difluorophenoxy)aniline as black oil.

Step 4

Into a 250-mL 4-necked round-bottom flask, was placed 4-(2,6-difluorophenoxy)-aniline (8.84 g, 39.96 mmol, 1.00 equiv), hydrogen chloride (37%) (10.14 g, 277.81 mmol, 6.95 equiv) and water (20 mL). NaNO$_2$ (3.04 g, 44.06 mmol, 1.10 equiv) in water (10 mL) was added dropwise with stirring at 0° C. over 5 min., and the reaction mixture was stirred for 30 mins at 0° C. The reaction mixture was added into a solution of NaI (18 g, 120.00 mmol, 3.00 equiv) in water (20 mL) at 25° C. in batches over 5 min. The resulting solution was stirred for 2 h at 25° C. and then extracted with of ethyl acetate and the organic layers were combined. The combined organic layers were washed with water and brine, dried over anhydrous sodium sulfate and concentrated under vacuum to give 10.2 g (77%) of 1,3-difluoro-2-(4-iodophenoxy)benzene as brown oil.

Step 5

Into a 100 mL 3-necked round-bottom flask purged and maintained in an inert atmosphere of nitrogen, was placed a solution of 1,3-difluoro-2-(4-iodophenoxy)benzene (2 g, 6.02 mmol, 1.00 equiv) in N,N-dimethylformamide (50 mL), 4,4,5,5-tetramethyl-2-(tetramethyl-1,3,2-dioxaborolan-2-yl)-1,3,2-dioxaborolane (1.68 g, 6.62 mmol, 1.10 equiv), potassium acetate (1.76 g, 17.93 mmol, 3.0 equiv), and Pd(OAc)$_2$ (68 mg, 0.30 mmol, 0.05 equiv). The resulting solution was stirred for 12 h at 85° C. in an oil bath. The reaction mixture was then quenched with water. The resulting solution was extracted with ethyl acetate and the organic layers combined and washed with water and brine. The organics were dried over anhydrous sodium sulfate and concentrated under vacuum. The residue was loaded onto a silica gel column and eluted with ethyl acetate/petroleum ether (1/8) to give 1.5 g (75%) of 2-[4-(2,6-difluorophenoxy)phenyl]-4,4,5,5-tetramethyl-1,3,2-dioxaborolane as a light yellow solid.

Step 6

Into a 100 mL, 3-necked round-bottom flask purged and maintained in an inert atmosphere of nitrogen, was placed a solution of tert-butyl (2R)-2-([4-amino-3-iodo-1H-pyrazolo[3,4-d]pyrimidin-1-yl]methyl)pyrrolidine-1-carboxylate (300 mg, 0.68 mmol, 1.00 equiv) in 1,4-dioxane/water (60/15 mL), 2-[4-(2,6-difluorophenoxy)phenyl]-4,4,5,5-tetramethyl-1,3,2-dioxaborolane (290 mg, 0.87 mmol, 1.3 equiv), sodium carbonate (180 mg, 1.68 mmol, 2.5 equiv), and tetrakis(triphenylphosphane)palladium (40 mg, 0.03 mmol, 0.05 equiv). The resulting solution was stirred for 12 h at 90° C. in an oil bath and then concentrated under vacuum. The resulting solution was diluted with 50 mL of dichloromethane, washed with water and brine. The organics were dried over anhydrous sodium sulfate and concentrated under vacuum. The residue was loaded onto a silica gel column and eluted with dichloromethane/methanol (20/1) to give 280 mg (79%) of tert-butyl (2R)-2-([4-amino-3-[4-(2,6-difluorophenoxy)phenyl]-1H-pyrazolo[3,4-d]pyrimidin-1-yl]methyl)pyrrolidine-1-carboxylate as a white solid.

Step 7

Into a 50 mL round-bottom flask, was placed a solution of tert-butyl (2R)-2-([4-amino-3-[4-(2,6-difluorophenoxy)phenyl]-1H-pyrazolo[3,4-d]pyrimidin-1-yl]methyl)-pyrrolidine-1-carboxylate (280 mg, 0.54 mmol, 1.00 equiv) in dichloromethane (10 mL). Trifluoroacetic acid (2 mg, 0.02 mmol, 0.03 equiv) was added dropwise with stirring at 25° C. The resulting solution was stirred for 3 h at 25° C. and then concentrated under vacuum. The resulting solution was diluted with 50 mL of dichloromethane, washed with ethyl acetate and H$_2$O, brine and concentrated under vacuum to give 200 mg (88%) of 3-[4-(2,6-difluorophenoxy)phenyl]-1-[(2R)-pyrrolidin-2-ylmethyl]-1H-pyrazolo[3,4-d]pyrimidin-4-amine as a white solid.

Step 8

Into a 100 mL round-bottom flask, was placed a solution of 3-[4-(2,6-difluoro-phenoxy)phenyl]-1-[(2R)-pyrrolidin-2-ylmethyl]-1H-pyrazolo[3,4-d]pyrimidin-4-amine (200 mg, 0.47 mmol, 1.00 equiv) in dichloromethane (10 mL), 2-cyanoacetic acid (121 mg, 1.42 mmol, 3.00 equiv), and 1,1-carbonyldiimidazole (230 mg, 1.42 mmol, 3.00 equiv). The resulting solution was stirred for 12 h at 25° C. and then washed with water and brine. The mixture was dried over anhydrous sodium sulfate and concentrated under vacuum. The residue was loaded onto a silica gel column and eluted with dichloromethane/methanol (50/1) to give 112 mg (48%) of 3-[(2R)-2-([4-amino-3-[4-(2,6-difluorophenoxy)phenyl]-1H-pyrazolo[3,4-d]pyrimidin-1-yl]methyl)pyrrolidin-1-yl]-3-oxopropanenitrile as a white solid.

Step 9

Into a 10 mL sealed tube, was placed a solution of 3-[(2R)-2-([4-amino-3-[4-(2,6-difluorophenoxy)phenyl]-1H-pyrazolo[3,4-d]pyrimidin-1-yl]methyl)pyrrolidin-1-yl]-3-oxopropanenitrile (100 mg, 0.20 mmol, 1.00 equiv) in methanol (3 mL), cyclopropanecarbaldehyde (1 mL), and piperidine (1 mL). The resulting solution was stirred for 12 h at 25° C. and then concentrated under vacuum. The resulting solution was diluted with 10 mL of dichloromethane, washed with saturated aqueous NH$_4$Cl, water and brine. The organics were dried over anhydrous sodium sulfate and concentrated under vacuum and the residue was purified via column chromatography using dichloromethane/methanol (20/1) to give 26 mg (23%) of the title compound as a white solid. LC-MS: (ES, m/z): 542 [M+H].

Example 13

Synthesis of (R)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile

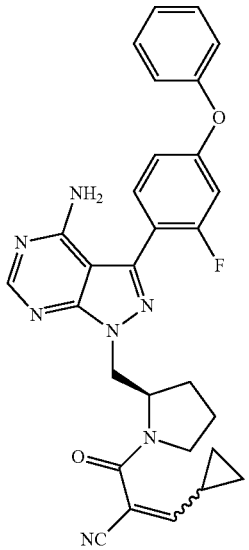 [SMILES: N#CC(=CC1CC1)C(=O)N1CCC[C@@H]1Cn1nc(-c2ccc(Oc3ccccc3)cc2F)c2c(N)ncnc21]

Step 1

Into a 250 mL round-bottom flask, was placed a solution of 4-bromo-3-fluorophenol (5 g, 26.18 mmol, 1.00 equiv) in dichloromethane (100 mL), phenylboronic acid (3.5 g, 28.70 mmol, 1.10 equiv), Cu(AcO)$_2$ (5.7 g), triethylamine (5.3 g), and 4 A molecular sieves (15 g). The resulting solution was stirred overnight at room temperature. The solids were filtered out. The filtrate was dried over anhydrous sodium sulfate and concentrated under vacuum. The residue was loaded onto a silica gel column and eluted with ethyl acetate/petroleum ether (1:100-1:50). This resulted in 2 g (29%) of 1-bromo-2-fluoro-4-phenoxybenzene as colorless oil.

Step 2

Into a 100 mL 3-necked round-bottom flask purged and maintained under an inert atmosphere of nitrogen, was placed a solution of 1-bromo-2-fluoro-4-phenoxybenzene (2 g, 7.49 mmol, 1.00 equiv) in tetrahydrofuran (20 mL). BuLi (1M) (8 mL) was added dropwise with stirring at −70 to −80° C. The resulting solution was stirred for 30 min at −70-80° C. in a liquid nitrogen bath. Tris(propan-2-yl)borate (1.7 g, 9.04 mmol, 1.21 equiv) was added dropwise with stirring at −70 to −80° C. The resulting solution was allowed to react, with stirring, for an additional 2 h while the temperature was maintained at −70 to −80° C. The reaction was then quenched by the addition of 100 mL of water, extracted with ethyl acetate and the organic layers were combined and dried over anhydrous sodium sulfate and concentrated under vacuum. The residue was loaded onto a silica gel column and eluted with ethyl acetate/petroleum ether (1:20) to give 1.6 g (92%) of (2-fluoro-4-phenoxyphenyl)-boronic acid as a white solid.

Step 3

Into a 100 mL, 3-necked round-bottom flask purged and maintained under an inert atmosphere of nitrogen, was placed tert-butyl (2R)-2-([4-amino-3-iodo-1H-pyrazolo[3,4- d]pyrimidin-1-yl]methyl)pyrrolidine-1-carboxylate (380 mg, 0.86 mmol, 1.00 equiv), (2-fluoro-4-phenoxyphenyl) boronic acid (240 mg, 1.03 mmol, 1.20 equiv), tetrakis-(triphenylphosphane) palladium (60 mg, 0.05 mmol, 0.06 equiv), dioxane (50 mL), sodium carbonate (228 mg, 2.15 mmol, 2.50 equiv) and water (10 mL). The resulting solution was stirred for 12 h at 80° C. in an oil bath. The resulting mixture was concentrated under vacuum and the resulting solution was extracted with dichloromethane and the organic layers combined, dried and concentrated under vacuum. The residue was loaded onto a silica gel column and eluted with dichloromethane/methanol (50/1) to give 0.347 g (80%) of tert-butyl (2R)-2-[[4-amino-3-(2-fluoro-4-phenoxyphenyl)-1H-pyrazolo[3,4-d]pyrimidin-1-yl]methyl]pyrrolidine-1-carboxylate as a brown solid.

Step 4

Into a 100 mL, round-bottom flask, was placed a solution of tert-butyl (2R)-2-[[4-amino-3-(2-fluoro-4-phenoxyphenyl)-1H-pyrazolo[3,4-d]pyrimidin-1-yl]methyl]pyrrolidine-1-carboxylate (347 mg, 0.69 mmol, 1.00 equiv) in dichloromethane (50 mL). Trifluoroacetic acid (10 mL) dropwise with stirring over 10 min and the resulting solution was stirred for 3 h at 25° C. The resulting mixture was concentrated under vacuum to give 0.278 g (crude) of 3-(2-fluoro-4-phenoxyphenyl)-1-[(2R)-pyrrolidin-2-ylmethyl]-1H-pyrazolo[3,4-d]pyrimidin-4-amine as brown oil.

Step 5

Into a 100 mL round-bottom flask, was placed 3-(2-fluoro-4-phenoxyphenyl)-1-[(2R)-pyrrolidin-2-ylmethyl]-1H-pyrazolo[3,4-d]pyrimidin-4-amine (278 mg, 0.69 mmol, 1.00 equiv), 2-cyanoacetic acid (36.8 mg, 0.43 mmol, 0.80 equiv), HATU (210 mg, 0.55 mmol, 0.80 equiv), triethylamine (109 mg, 1.08 mmol, 2.00 equiv), and N,N-dimethylformamide (50 mL). The resulting solution was stirred for 3 h at 25° C., then diluted with 200 mL of water and extracted with ethyl acetate and the organic layers combined, dried and concentrated under vacuum. The residue was loaded onto a silica gel column and eluted with dichloromethane/methanol (50/1) to give 200 mg (62%) of 3-[(2R)-2-[[4-amino-3-(2-fluoro-4-phenoxyphenyl)-1H-pyrazolo[3,4-d]pyrimidin-1-yl]methyl]pyrrolidin-1-yl]-3-oxo-propanenitrile as a yellow solid.

Step 6

Into a 10 mL round-bottom flask, was placed 3-[(2R)-2-[[4-amino-3-(2-fluoro-4-phenoxyphenyl)-1H-pyrazolo[3,4-d]pyrimidin-1-yl]methyl]pyrrolidin-1-yl]-3-oxopropanenitrile (100 mg, 0.21 mmol, 1.00 equiv), piperidine (18 mg, 0.21 mmol, 1.00 equiv), cyclopropanecarbaldehyde (30 mg, 0.43 mmol, 2.00 equiv), and methanol (5 mL). The resulting solution was stirred for 12 h at 25° C. and then concentrated under vacuum. The residue was loaded onto a silica gel column and eluted with dichloromethane/methanol (50/1) to give 38 mg (33%) of the title compound as a off-white solid.

LC-MS; (ES, m/z): MS (ESI, pos. ion) m/z: 524 (M+1).

Example 14

Synthesis of (R)-2-(2-((4-amino-3-(4-(2,3-difluorophenoxy)phenyl)-1H-pyrazolo[3,4-d]pyrimidin-1-yl) methyl)pyrrolidine-1-carbonyl)-3-cyclopropylacrylonitrile

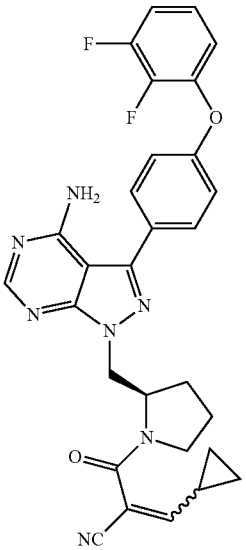 [SMILES: N#CC(=CC1CC1)C(=O)N1CCC[C@@H]1Cn1nc(-c2ccc(Oc3cccc(F)c3F)cc2)c2c(N)ncnc21]

Step 1

Into a 500 mL round-bottom flask, was placed a solution of (2,3-difluorophenyl)-boronic acid (30 g, 189.98 mmol, 1.00 equiv) in dichloromethane (250 mL). $H_2O_2$ (30 mL) was added dropwise with stirring. The resulting solution was stirred for 2 h at 25° C. The resulting mixture was washed with water and brine, dried over anhydrous magnesium sulfate and concentrated under vacuum to give 23 g (93%) of 2,3-difluorophenol as brown oil.

Step 2

Into a 500 mL, 4-necked round-bottom flask purged and maintained under an inert atmosphere of nitrogen, was placed a solution of sodium hydride (6.8 g, 170.00 mmol, 1.70 equiv, 60%) in N,N-dimethylformamide (200 mL). A solution of 1-fluoro-4-nitrobenzene (14.1 g, 99.93 mmol, 1.00 equiv) in N, N-dimethylformamide (50 mL) was added dropwise with stirring at 0° C. in 15 min. The resulting solution was stirred for 2 h at room temperature. CuCl (10 g, 101.01 mmol, 1.00 equiv) was added and a solution of 2,3-difluorophenol (15.6 g, 119.91 mmol, 1.20 equiv) in N,N-dimethylformamide (50 mL) was added dropwise with stirring. The resulting solution was allowed to react, with stirring, for an additional 12 h while the temperature was maintained at 100° C. in an oil bath. The resulting solution was extracted with ether and the organic layers combined. The organic layers was washed with water and brine, dried over anhydrous sodium sulfate and concentrated under vacuum. The residue was loaded onto a silica gel column and eluted with ethyl acetate/petroleum ether (1:8) to give 21.2 g (84%) of 1,2-difluoro-3-(4-nitrophenoxy)benzene as a brown solid.

Step 3

Into a 500 mL, 3-necked round-bottom flask purged and maintained under an inert atmosphere of nitrogen, was placed a solution of 1,2-difluoro-3-(4-nitrophenoxy)benzene (21.2 g, 84.40 mmol, 1.00 equiv) in methanol (200 mL), and Raney Nickel (2 g). A solution of hydrazine hydrate (12.67 g, 3.00 equiv) in methanol (50 mL) was added dropwise with stirring in 15 min. The resulting solution was stirred for 12 h at 25° C. The solids were filtered out and the filtrate was concentrated under vacuum. The residue was diluted with 200 mL of ethyl acetate and washed with water and brine, dried over anhydrous sodium sulfate and concentrated under vacuum to give 16.3 g (87%) of 4-(2,3-difluorophenoxy) aniline as black oil.

Step 4

Into a 250-mL 4-necked round-bottom flask, was placed 4-(2,3-difluorophenoxy)-aniline (8.84 g, 39.96 mmol, 1.00 equiv), hydrogen chloride (10.14 g, 100.01 mmol, 2.50 equiv), and water (20 mL). A solution of NaNO$_2$ (3.04 g, 44.06 mmol, 1.10 equiv) in water (10 mL) was added dropwise with stirring in portions at 0° C. The mixture was stirred at 0° C. for half an hour. To this was added urea (1 g, 16.65 mmol). The mixture was stirred at 0° C. for 20 min and poured into the solution of NaI (18 g, 120.00 mmol, 3.00 equiv) in water (20 mL) at room temperature. The resulting solution was stirred at room temperature for 1 h and then extracted with ethyl acetate. The organic layers combined and dried over anhydrous sodium sulfate and concentrated under vacuum to give 10.5 g (79%) of 1,2-difluoro-3-(4-iodophenoxy)benzene as brown oil.

Step 5

Into a 100 mL, 3-necked round-bottom flask purged and maintained under an inert atmosphere of nitrogen, was placed a solution of 1,2-difluoro-3-(4-iodophenoxy)benzene (2 g, 6.02 mmol, 1.00 equiv) in N,N-dimethylformamide (50 mL), 4,4,5,5-tetramethyl-2-(tetramethyl-1,3,2-dioxaborolan-2-yl)-1,3,2-dioxaborolane (1.68 g, 6.62 mmol, 1.10 equiv), potassium acetate (68 mg, 0.69 mmol, 0.05 equiv), and Pd(OAc)$_2$ (1.76 g, 7.84 mmol, 3.00 equiv). The resulting solution was stirred for 12 h at 85° C. in an oil bath. The reaction was then diluted with water, extracted with ethyl acetate and the organic layers were combined. The organics were washed with water and brine, dried over anhydrous sodium sulfate and concentrated under vacuum. The residue was loaded onto a silica gel column and eluted with ethyl acetate/petroleum ether (1/8) to give 1.5 g (75%) of 2-[4-(2,3-difluorophenoxy)phenyl]-4,4,5,5-tetramethyl-1,3,2-dioxaborolane as a light yellow solid.

Step 6

Into a 100 mL, 3-necked round-bottom flask purged and maintained under an inert atmosphere of nitrogen, was placed tert-butyl (2R)-2-([4-amino-3-iodo-1H-pyrazolo[3,4-d]pyrimidin-1-yl]methyl)pyrrolidine-1-carboxylate (300 mg, 0.68 mmol, 1.00 equiv), a solution of 2-[4-(2,3-difluorophenoxy)phenyl]-4,4,5,5-tetramethyl-1,3,2-dioxaborolane (290 mg, 0.87 mmol, 1.10 equiv) in dioxane (9 mL), tetrakis(triphenylphosphane)-palladium (40 mg, 0.03 mmol, 0.05 equiv), and a solution of sodium carbonate (179 mg, 1.67 mmol, 2.50 equiv) in water (3 mL). The resulting solution was stirred for 12 h at 100° C. in an oil bath. The resulting mixture was concentrated under vacuum, and the solution was diluted with ethyl acetate. The resulting mixture was washed with water and brine, dried over anhydrous sodium sulfate and concentrated under vacuum. The residue was loaded onto a silica gel column and eluted with dichloromethane/methanol (20/1) to give 250 mg (71%) of tert-butyl (2R)-2-([4-amino-3-[4-(2,3-difluorophenoxy)phenyl]-1H-pyrazolo[3,4-d]pyrimidin-1-yl]methyl)pyrrolidine-1-carboxylate as a white solid.

Step 7

Into a 100 mL, round-bottom flask, was placed a solution of tert-butyl (2R)-2-([4-amino-3-[4-(2,3-difluorophenoxy) phenyl]-1H-pyrazolo[3,4-d]pyrimidin-1-yl]methyl)-pyrrolidine-1-carboxylate (350 mg, 0.67 mmol, 1.00 equiv) in dichloromethane (10 mL). Trifluoroacetic acid (2 mL) dropwise with stirring and the resulting solution was stirred for 3 h at 25° C. The resulting mixture was concentrated under vacuum to give 200 mg (46%) of 3-[4-(2,3-difluorophenoxy)phenyl]-1-[(2R)-pyrrolidin-2-ylmethyl]-1H-pyrazolo[3,4-d]pyrimidin-4-amine bis(trifluoroacetic acid) salt as a brown solid.

Step 8

Into a 100 mL, round-bottom flask, was placed a solution of 3-[4-(2,3-difluorophenoxy)phenyl]-1-[(2R)-pyrrolidin-2-ylmethyl]-1H-pyrazolo[3,4-d]pyrimidin-4-amine bis(trifluoroacetic acid) salt (200 mg, 0.31 mmol, 1.00 equiv) in dichloromethane (10 mL), CDI (324 mg, 2.00 mmol, 6.50 equiv), and 2-cyanoacetic acid (170 mg, 2.00 mmol, 6.50 equiv). The resulting solution was stirred for 12 h at 25° C. and the resulting mixture was washed with water and brine. The organics were dried over anhydrous magnesium sulfate and concentrated under vacuum. The residue was loaded onto a silica gel column and eluted with dichloromethane/ methanol (20/1) to give 109 mg (72%) of 3-[(2R)-2-([4-amino-3-[4-(2,3-difluorophenoxy)phenyl]-1H-pyrazolo[3, 4-d]pyrimidin-1-yl]methyl)pyrrolidin-1-yl]-3-oxopropanenitrile as a white solid.

Step 9

Into a 50 mL, round-bottom flask, was placed a solution of 3-[(2R)-2-([4-amino-3-[4-(2,3-difluorophenoxy)phenyl]-1H-pyrazolo[3,4-d]pyrimidin-1-yl]methyl)pyrrolidin-1-yl]-3-oxopropanenitrile (109 mg, 0.22 mmol, 1.00 equiv) in methanol (10 mL), cyclopropanecarbaldehyde (1 mL), and piperidine (1 mL). The resulting solution was stirred for 12 h at 25° C. and then concentrated under vacuum. The resulting solution was diluted with ethyl acetate and the resulting mixture was washed with water and brine. The organics were dried over anhydrous sodium sulfate and concentrated under vacuum. The residue was loaded onto a silica gel column and eluted with dichloromethane/methanol (20/1) to give 32 mg (25%) of the title compound as a white solid. LC-MS: (ES, m/z): 542 [M+H]$^+$.

Example 15

Synthesis of (R)-2-(2-((4-amino-3-(4-(3,5-difluorophenoxy)phenyl)-1H-pyrazolo[3,4-d]pyrimidin-1-yl) methyl)pyrrolidine-1-carbonyl)-3-cyclopropylacrylonitrile

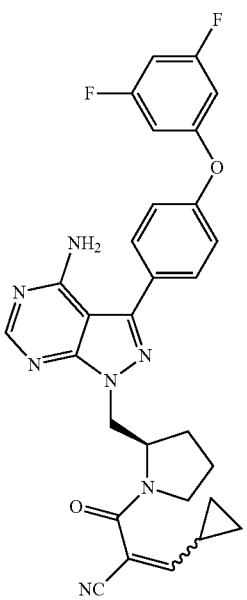 [SMILES: N#CC(=CC1CC1)C(=O)N1CCC[C@@H]1Cn1nc(-c2ccc(Oc3cc(F)cc(F)c3)cc2)c2c(N)ncnc21]

Step 1

Into a 250-mL round-bottom flask, was placed a solution of 4-(tetramethyl-1,3,2-dioxaborolan-2-yl)phenol (5 g, 22.72 mmol, 1.00 equiv) in dichloromethane (100 mL), (3,5-difluorophenyl)boronic acid (4 g, 25.33 mmol, 1.11 equiv), Cu(AcO)2 (5 g), 4 A molecular sieves (15 g), triethylamine (4.6 g). The resulting solution was stirred for overnight at room temperature. The solids were filtered out. The filtrate was dried over anhydrous sodium sulfate and concentrated under vacuum. The residue was applied onto a silica gel column with ethyl acetate/petroleum ether (1:100-1:50). This resulted in 2 g (27%) of 2-[4-(3,5-difluorophenoxy)phenyl]-4,4,5,5-tetramethyl-1,3,2-dioxaborolane as a colorless oil.

Step 2

Into a 100 mL, 3-necked round-bottom flask purged and maintained with an inert atmosphere of nitrogen, was placed tert-butyl (2R)-2-([4-amino-3-iodo-1H-pyrazolo[3,4-d]pyrimidin-1-yl]methyl)pyrrolidine-1-carboxylate (250 mg, 0.56 mmol, 1.00 equiv), 2-[4-(3,5-difluorophenoxy)phenyl]-4,4,5,5-tetramethyl-1,3,2-dioxaborolane (226 mg, 0.68 mmol, 1.20 equiv), tetrakis(triphenylphosphane)palladium (39 mg, 0.03 mmol, 0.06 equiv), dioxane (50 mL), sodium carbonate (149 mg, 1.41 mmol, 2.50 equiv), and water (10 mL). The resulting solution was stirred for 12 h at 80° C. in an oil bath and then concentrated under vacuum. The resulting solution was extracted with dichloromethane and the organic layers combined, dried and concentrated under vacuum. The residue was loaded onto a silica gel column and eluted with dichloromethane/methanol (50/1) to give 0.237 g (81%) of tert-butyl (2R)-2-([4-amino-3-[4-(3,5-difluorophenoxy)phenyl]-1H-pyrazolo[3,4-d]pyrimidin-1-yl]methyl)pyrrolidine-1-carboxylate as a brown solid.

Step 3

Into a 100 mL, round-bottom flask, was placed a solution of tert-butyl (2R)-2-([4-amino-3-[4-(3,5-difluorophenoxy)phenyl]-1H-pyrazolo[3,4-d]pyrimidin-1-yl]methyl)pyrrolidine-1-carboxylate (230 mg, 0.44 mmol, 1.00 equiv) in dichloromethane (50 mL). This was followed by the addition of trifluoroacetic acid (10 mL) dropwise with stirring over 10 min. The resulting solution was stirred for 3 h at 25° C. The resulting mixture was concentrated under vacuum to give 0.185 g (crude) of 3-[4-(3,5-difluorophenoxy)phenyl]-1-[(2R)-pyrrolidin-2-ylmethyl]-1H-pyrazolo[3,4-d]pyrimidin-4-amine as a brown oil.

Step 4

Into a 100 mL, round-bottom flask, was placed 3-[4-(3,5-difluorophenoxy)phenyl]-1-[(2R)-pyrrolidin-2-ylmethyl]-1H-pyrazolo[3,4-d]pyrimidin-4-amine (185 mg, 0.44 mmol, 1.00 equiv), 2-cyanoacetic acid (30.7 mg, 0.36 mmol, 0.80 equiv), HATU (138 mg, 0.36 mmol, 0.80 equiv), triethylamine (91 mg, 0.90 mmol, 2.00 equiv), and N,N-dimethylformamide (50 mL). The resulting solution was stirred for 3 h at 25° C. and then extracted with ethyl acetate and the organic layers combined and concentrated under vacuum. The residue was loaded onto a silica gel column and eluted with dichloromethane/methanol (50/1) to give 101 mg (47%) of 3-[(2R)-2-([4-amino-3-[4-(3,5-difluorophenoxy)phenyl]-1H-pyrazolo[3,4-d]pyrimidin-1-yl]methyl)pyrrolidin-1-yl]-3-oxopropanenitrile as a off-white solid.

Step 5

Into a 10-mL round-bottom flask, was placed cyclopropanecarbaldehyde (28.7 mg, 0.41 mmol, 2.00 equiv), piperidine (17.4 mg, 0.20 mmol, 1.00 equiv), 3-[(2R)-2-([4-amino-3-[4-(3,5-difluorophenoxy)phenyl]-1H-pyrazolo[3,4-d]pyrimidin-1-yl]methyl)pyrrolidin-1-yl]-3-oxopropanenitrile (100 mg, 0.20 mmol, 1.00 equiv), and methanol (5 mL). The resulting solution was stirred for 12 h at 25° C. and then concentrated under vacuum. The residue was loaded onto a silica gel column and eluted with dichloromethane/methanol (50/1) to give 53.12 mg (45%) of the title compound as an off-white solid. LC-MS: (ES, m/z): MS (ESI, pos. ion) m/z: 541 (M+1).

Example 16

Synthesis of (R)-2-(3-(4-amino-3-(4-(2-fluorophenoxy)phenyl)-1H-pyrazolo[3,4-d]pyrimidin-1-yl)piperidine-1-carbonyl)-3-cyclopropylacrylonitrile

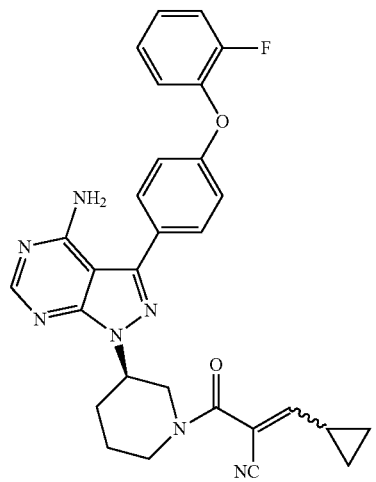 [SMILES: N#CC(=CC1CC1)C(=O)N1CCC[C@@H](n2nc(-c3ccc(Oc4ccccc4F)cc3)c3c(N)ncnc32)C1]

Step 1

Into a 100 mL, 3-necked round-bottom flask purged and maintained with an inert atmosphere of nitrogen, was placed a solution of tert-butyl (3R)-3-[4-amino-3-iodo-1H-pyrazolo[3,4-d]pyrimidin-1-yl]piperidine-1-carboxylate (300 mg, 0.68 mmol, 1.00 equiv) in dioxane/H2O (7/3=V/V) (30 mL), [4-(2-fluorophenoxy)phenyl]boronic acid (500 mg, 2.16 mmol, 6.99 equiv), sodium carbonate (200 mg, 1.89 mmol, 0.26 equiv), and Pd(PPh3)4 (500 mg, 0.43 mmol, 3.19 equiv). The resulting solution was stirred overnight at 100° C. in an oil bath an then concentrated under vacuum. The residue was loaded onto a silica gel column and eluted with dichloromethane/methanol (100:1) to give 0.2 g (59%) of tert-butyl (3R)-3-[4-amino-3-[4-(2-fluorophenoxy)phenyl]-1H-pyrazolo[3,4-d]pyrimidin-1-yl]piperidine-1-carboxylate as a light yellow solid.

Step 2

Into a 100 mL, round-bottom flask purged and maintained under an inert atmosphere of nitrogen, was placed a solution of tert-butyl (3R)-3-[4-amino-3-[4-(2-fluorophenoxy)phenyl]-1H-pyrazolo[3,4-d]pyrimidin-1-yl]piperidine-1-carboxylate (200 mg, 0.40 mmol, 1.00 equiv) in dichloromethane (20 mL), and trifluoroacetic acid (10 g, 87.70 mmol, 221.25 equiv). The resulting solution was stirred overnight at room temperature and then concentrated under vacuum. The pH value of the solution was adjusted to 8-10 with 10% aqueous sodium carbonate. The solution was extracted with dichloromethane and the organic layers were combined and dried over anhydrous sodium sulfate and concentrated under vacuum to give 0.1 g (62%) of 3-[4-(2-fluorophenoxy)phenyl]-1-((3R)-piperidin-3-yl)-1H-pyrazolo[3,4-d]pyrimidin-4-amine as a light yellow solid.

Step 3

Into a 50 mL round-bottom flask, was placed a solution of 3-[4-(2-fluorophenoxy)-phenyl]-1-[(3R)-piperidin-3-yl]-1H-pyrazolo[3,4-d]pyrimidin-4-amine (100 mg, 0.25 mmol, 1.00 equiv) in dichloromethane (10 mL), 1-[(1H-imidazol-1-yl)carbonyl]-1H-imidazole (60 mg, 0.37 mmol, 1.50 equiv), and 2-cyanoacetic acid (110 mg, 1.29 mmol, 5.23 equiv). The resulting solution was stirred for 60 min at room temperature and then concentrated under vacuum. The residue was loaded onto a silica gel column and eluted with dichloromethane/methanol (100:1) to give 0.06 g (51%) of 3-[(3R)-3-[4-amino-3-[4-(2-fluorophenoxy)phenyl]-1H-pyrazolo[3,4-d]pyrimidin-1-yl]piperidin-1-yl]-3-oxopropanenitrile as a light yellow solid.

Step 4

Into a 10 mL round-bottom flask, was placed a solution of 3-[(3R)-3-[4-amino-3-[4-(2-fluorophenoxy)phenyl]-1H-pyrazolo[3,4-d]pyrimidin-1-yl]piperidin-1-yl]-3-oxopropanenitrile (60 mg, 0.13 mmol, 1.00 equiv) in methanol (10 mL), cyclopropanecarbaldehyde (50 mg, 0.71 mmol, 5.61 equiv), and piperidine (70 mg, 0.82 mmol, 6.46 equiv). The resulting solution was stirred for 30 min at room temperature and then concentrated under vacuum. The residue was loaded onto a silica gel column and eluted with dichloromethane/methanol (100:1) to give 0.015 g (23%) of the title compound as an off-white solid. LC-MS0: (ES, m/z): 524 [M+H]+.

Example 17

Synthesis of (R)-2-(3-(4-amino-3-(4-(3-fluorophenoxy)phenyl)-1H-pyrazolo[3,4-d]pyrimidin-1-yl) piperidine-1-carbonyl)-3-cyclopropylacrylonitrile

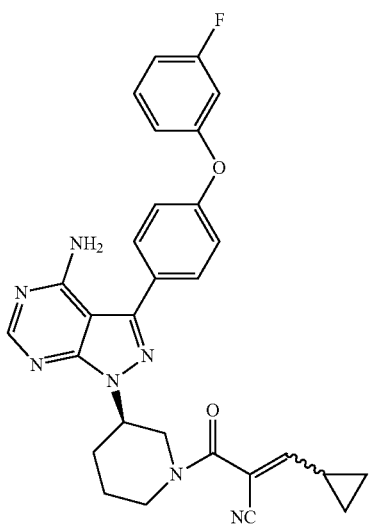 [SMILES: N#CC(=CC1CC1)C(=O)N1CCC[C@@H](n2nc(-c3ccc(Oc4cccc(F)c4)cc3)c3c(N)ncnc32)C1]

Step 1

Into a 250 mL round-bottom flask, was placed a solution of 4-(tetramethyl-1,3,2-dioxaborolan-2-yl)phenol (5 g, 22.72 mmol, 1.00 equiv) in dichloromethane (100 mL), (3-fluorophenyl)boronic acid (3.5 g, 25.01 mmol, 1.10 equiv), Cu(AcO)$_2$ (5 g), 4 A molecular sieves (15 g), and triethylamine (4.6 g). The resulting solution was stirred overnight at room temperature. The solids were filtered out and the filtrate was dried over anhydrous sodium sulfate and concentrated under vacuum. The residue was loaded onto a silica gel column and eluted with ethyl acetate/petroleum ether (1:100-1:50) to give 1.8 g (25%) of 2-[4-(3-fluorophenoxy)phenyl]-4,4,5,5-tetramethyl-1,3,2-dioxaborolane as a colorless oil.

Step 2

Into a 100 mL 3-necked round-bottom flask purged and maintained with an inert atmosphere of nitrogen, was placed tert-butyl (3R)-3-[4-amino-3-iodo-1H-pyrazolo[3,4-d]pyrimidin-1-yl]piperidine-1-carboxylate (300 mg, 0.68 mmol, 1.00 equiv), 2-[4-(3-fluorophenoxy)phenyl]-4,4,5,5-tetramethyl-1,3,2-dioxaborolane (255 mg, 0.81 mmol, 1.20 equiv), sodium carbonate (143 g, 1.35 mol, 1998.01 equiv), ethylene glycol dimethyl ether (50 mL), water (15 mL), and Pd(PPh$_3$)$_4$ (40 mg, 0.03 mmol, 0.05 equiv). The resulting solution was stirred overnight at 80° C. and then concentrated under vacuum. The residue was loaded onto a silica gel column and eluted with dichloromethane/methanol (100/1) to give 260 mg (76%) of tert-butyl (3R)-3-[4-amino-3-[4-(3-fluorophenoxy)phenyl]-1H-pyrazolo[3,4-d]pyrimidin-1-yl]piperidine-1-carboxylate as a yellow solid.

Step 3

Into a 100 mL round-bottom flask, was placed a solution of tert-butyl (3R)-3-[4-amino-3-[4-(3-fluorophenoxy)phenyl]-1H-pyrazolo[3,4-d]pyrimidin-1-yl]piperidine-1-carboxylate (260 mg, 0.52 mmol, 1.00 equiv) in dichloromethane (50 mL). Trifluoroacetic acid (10 mL) was added dropwise with stirring. The resulting solution was stirred for 12 h at room temperature and then concentrated under vacuum. The residue was diluted with 20 mL of water. The pH value of the solution was adjusted to >7 with sodium carbonate. The resulting solution was extracted with dichloromethane and the organic layers combined and dried over anhydrous sodium sulfate and concentrated under vacuum to give 180 mg (86%) of 3-[4-(3-fluorophenoxy)phenyl]-1-[(3R)-piperidin-3-yl]-1H-pyrazolo[3,4-d]pyrimidin-4-amine as a brown solid.

Step 4

Into a 100 mL round-bottom flask, was placed a solution of 3-[4-(3-fluorophenoxy)-phenyl]-1-[(3R)-piperidin-3-yl]-1H-pyrazolo[3,4-d]pyrimidin-4-amine (180 mg, 0.45 mmol, 1.00 equiv) in dichloromethane (50 mL), 2-cyanoacetic acid (56 mg, 0.66 mmol, 1.50 equiv), and 1-[(1H-imidazol-1-yl)carbonyl]-1H-imidazole (108 mg, 0.67 mmol, 1.50 equiv). The resulting solution was stirred for 24 h at room temperature and then diluted with 100 mL dichloromethane. The resulting mixture was washed NH$_4$Cl, dried over anhydrous sodium sulfate and concentrated under vacuum. The residue was loaded onto a silica gel column and eluted with dichloromethane/methanol (100:1) to give 120 mg (57%) of 3-[(3R)-3-[4-amino-3-[4-(3-fluorophenoxy)phenyl]-1H-pyrazolo[3,4-d]pyrimidin-1-yl]piperidin-1-yl]-3-oxopropanenitrile as a white solid.

Step 5

Into a 50 mL round-bottom flask, was placed a solution of 3-[(3R)-3-[4-amino-3-[4-(3-fluorophenoxy)phenyl]-1H-pyrazolo[3,4-d]pyrimidin-1-yl]piperidin-1-yl]-3-oxopropanenitrile (120 mg, 0.25 mmol, 1.00 equiv) in methanol (20 mL), cyclopropanecarbaldehyde (54 mg, 0.77 mmol, 3.00 equiv), piperidine (11 mg, 0.13 mmol, 0.50 equiv), and dichloromethane (5 mL). The resulting solution was stirred for 12 h at room temperature and then concentrated under vacuum. The residue was loaded onto a silica gel column and eluted with dichloromethane/methanol (100:1) to give 36 mg (27%) of the title compounds as a white solid. LC-MS: (ES, m/z): 524 [M+H]+.

Example 18

Synthesis of (R)-2-(3-(4-amino-3-(4-(2,3-difluorophenoxy)phenyl)-1H-pyrazolo[3,4-d]pyrimidin-1-yl)piperidine-1-carbonyl)-3-cyclopropylacrylonitrile

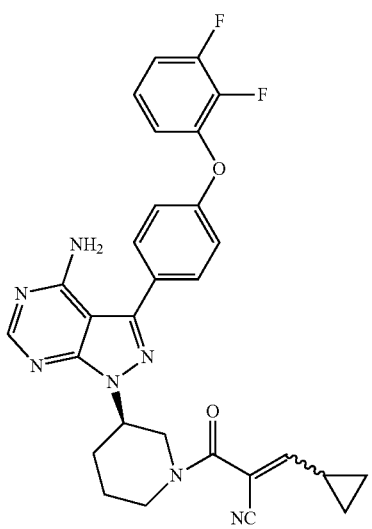 [SMILES: N#CC(=CC1CC1)C(=O)N1CCC[C@@H](n2nc(-c3ccc(Oc4cccc(F)c4F)cc3)c3c(N)ncnc32)C1]

Step 1

Into a 500-mL round-bottom flask, was placed a solution of tert-butyl (3S)-3-hydroxypiperidine-1-carboxylate (10 g, 49.69 mmol, 1.00 equiv) in pyridine (200 mL). 4-Methylbenzene-1-sulfonyl chloride (28.5 g, 149.49 mmol, 3.0 equiv) was added dropwise with stirring at 0° C. in 30 min. The resulting solution was stirred for 5 h at 25° C. and then concentrated under vacuum. The residue was diluted with 200 mL of ethyl acetate. The pH value of the solution was adjusted to 3 with hydrogen chloride (1M) and the resulting mixture was washed with sodium bicarbonate and water. The organics were washed with brine, dried over anhydrous sodium sulfate and concentrated under vacuum to give 15 g (85%) of tert-butyl (3S)-3-[[(4-methylbenzene)sulfonyl]oxy]piperidine-1-carboxylate as a light yellow solid.

Step 2

Into a 1000 mL 3-necked round-bottom flask, was placed a solution of 3-iodo-1H-pyrazolo[3,4-d]pyrimidin-4-amine (6 g, 22.99 mmol, 1.00 equiv) in N,N-dimethylformamide (500 mL), tert-butyl (3S)-3-[[(4-methylbenzene)sulfonyl]oxy]piperidine-1-carboxylate (9.8 g, 27.57 mmol, 1.20 equiv), and cesium carbonate (13.3 g, 40.82 mmol, 1.78 equiv). The resulting solution was stirred for 12 h at 60° C. in an oil bath and then quenched by the addition of 1500 mL of water. The resulting solution was extracted with dichloromethane and the organic layers combined. The organics were washed with brine, dried over anhydrous sodium sulfate and concentrated under vacuum. The residue was loaded onto a silica gel column and elution with ethyl acetate/petroleum ether (60%) gave 2.8 g (27%) of tert-butyl (3R)-3-[4-amino-3-iodo-1H-pyrazolo[3,4-d]pyrimidin-1-yl]piperidine-1-carboxylate (96.5%, e.e.) as a off-white solid.

Step 3

Into a 250 mL 3-necked round-bottom flask purged and maintained under an inert atmosphere of nitrogen, was placed a solution of tert-butyl (3R)-3-[4-amino-3-iodo-1H-pyrazolo[3,4-d]pyrimidin-1-yl]piperidine-1-carboxylate (500 mg, 1.13 mmol, 1.00 equiv) in 1,4-dioxane/H$_2$O (100/30 mL), 2-[4-(2,3-difluorophenoxy)phenyl]-4,4,5,5-tetramethyl-1,3,2-dioxaborolane (420 mg, 1.26 mmol, 1.1 equiv), sodium carbonate (240 mg, 2.26 mmol, 2.0 equiv), and Pd(PPh$_3$)$_4$ (65 mg, 0.06 mmol, 0.05 equiv). The resulting solution was stirred for 12 h at 90° C. in an oil bath. The resulting mixture was concentrated under vacuum and the resiude was diluted with water. The resulting solution was extracted with dichloromethane and the organic layers were combined, washed with brine and filtered. The filtrate was dried over anhydrous sodium sulfate and concentrated under vacuum. The residue was loaded onto a silica gel column and elution with dichloromethane/methanol (10/1) gave 480 mg (82%) of tert-butyl (3R)-3-[4-amino-3-[4-(2,3-difluorophenoxy)phenyl]-1H-pyrazolo[3,4-d]pyrimidin-1-yl]piperidine-1-carboxylate as a white solid.

Step 4

Into a 100 mL round-bottom flask, was placed a solution of tert-butyl (3R)-3-[4-amino-3-[4-(2,3-difluorophenoxy)phenyl]-1H-pyrazolo[3,4-d]pyrimidin-1-yl]piperidine-1-carboxylate (450 mg, 0.86 mmol, 1.00 equiv) in dichloromethane (40 mL) and CF$_3$COOH (10 mL). The resulting solution was stirred for 3 h at 25° C. and then concentrated under vacuum. The resulting solution was diluted with 50 mL of dichloromethane and washed with aqueous sodium bicarbonate and brine. The organics were dried over anhydrous sodium sulfate and concentrated under vacuum to give 400 mg (crude) of 3-[4-(2,3-difluorophenoxy)phenyl]-1-[(3R)-piperidin-3-yl]-1H-pyrazolo[3,4-d]pyrimidin-4-amine as a white solid.

Step 5

Into a 100 mL round-bottom flask, was placed a solution of 3-[4-(2,3-difluorophenoxy)-phenyl]-1-[(3R)-piperidin-3-yl]-1H-pyrazolo[3,4-d]pyrimidin-4-amine (300 mg, 0.71 mmol, 1.00 equiv) in dichloromethane (30 mL), HATU (400 mg, 1.05 mmol, 1.5 equiv), triethylamine (220 mg, 2.17 mmol, 3.0 equiv), and 2-cyanoacetic acid (90 mg, 1.06 mmol, 1.5 equiv). The resulting solution was stirred for 10 h at 25° C. and then washed with water and brine. The organics were dried over anhydrous sodium sulfate and concentrated. The residue was loaded onto a silica gel column and elution with dichloromethane/methanol (10/1) gave 240 mg (69%) of 3-[(3R)-3-[4-amino-3-[4-(2,3-difluorophenoxy)phenyl]-1H-pyrazolo[3,4-d]pyrimidin-1-yl]piperidin-1-yl]-3-oxopropanenitrile as a white solid.

Step 6

Into a 10 mL sealed tube, was placed a solution of 3-[(3R)-3-[4-amino-3-[4-(2,3-difluorophenoxy)phenyl]-1H-pyrazolo[3,4-d]pyrimidin-1-yl]piperidin-1-yl]-3-oxopropanenitrile (150 mg, 0.31 mmol, 1.00 equiv) in methanol (5 mL), cyclopropanecarbaldehyde (64 mg, 0.91 mmol, 3.0 equiv), and piperidine (78 mg). The resulting solution was stirred for 12 h at 25° C. and then concentrated under vacuum. The residue was diluted with 10 mL of dichloromethane and the resulting mixture was washed with saturated aqueous ammonium chloride, water and brine and dried over anhydrous sodium sulfate and concentrated. The residue was loaded onto a silica gel column and elution with dichloromethane/methanol (20/1) gave 28.5 mg (17%) of the title compound as a white solid. LC-MS: (ES, m/z): 542 [M+H]$^+$.

Example 19

Synthesis of (R)-2-(3-(4-amino-3-(4-(2,6-difluorophenoxy)phenyl)-1H-pyrazolo[3,4-d]pyrimidin-1-yl)piperidine-1-carbonyl)-3-cyclopropylacrylonitrile

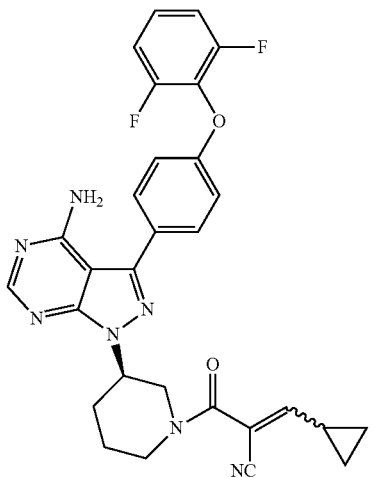 [SMILES: N#CC(=CC1CC1)C(=O)N1CCC[C@@H](n2nc(-c3ccc(Oc4c(F)cccc4F)cc3)c3c(N)ncnc32)C1]

Step 1

Into a 250 mL 3-necked round-bottom flask purged and maintained under an inert atmosphere of nitrogen, was placed a solution of tert-butyl (3R)-3-[4-amino-3-iodo-1H-pyrazolo[3,4-d]pyrimidin-1-yl]piperidine-1-carboxylate (500 mg, 1.13 mmol, 1.00 equiv) in 1,4-dioxane/H2O (100/30 mL), 2-[4-(2,6-difluorophenoxy)phenyl]-4,4,5,5-tetramethyl-1,3,2-dioxaborolane (420 mg, 1.26 mmol, 1.1 equiv), sodium carbonate (240 mg, 2.26 mmol, 2.0 equiv), and Pd(PPh3)4 (65 mg, 0.06 mmol, 0.05 equiv). The resulting solution was stirred for 15 h at 90° C. in an oil bath and then concentrated under vacuum. The residue was diluted with water and extracted with dichloromethane and the organic layers combined. The organics were washed with brine, dried over anhydrous sodium sulfate and concentrated. The residue was loaded onto a silica gel column and eluted with dichloromethane/methanol (10/1) to give 500 mg (85%) of tert-butyl (3R)-3-[4-amino-3-[4-(2,6-difluorophenoxy)-phenyl]-1H-pyrazolo[3,4-d]pyrimidin-1-yl]piperidine-1-carboxylate as a white solid.

Step 2

Into a 100 mL round-bottom flask, was placed a solution of tert-butyl (3R)-3-[4-amino-3-[4-(2,6-difluorophenoxy)phenyl]-1H-pyrazolo[3,4-d]pyrimidin-1-yl]piperidine-1-carboxylate (450 mg, 0.86 mmol, 1.00 equiv) in dichloromethane (40 mL). CF3COOH (10 mL) to added dropwise with stirring at 25° C. over 10 min and the resulting solution was stirred for 3 h at 25° C. and then concentrated under vacuum. The resulting solution was diluted with dichloromethane and washed with aqueous sodium bicarbonate and brine. The organics were dried over anhydrous sodium sulfate and concentrated under vacuum to give 410 mg of 3-[4-(2,6-difluorophenoxy)phenyl]-1-[(3R)-piperidin-3-yl]-1H-pyrazolo[3,4-d]pyrimidin-4-amine as a white solid.

Step 3

Into a 100 mL round-bottom flask, was placed a solution of 3-[4-(2,6-difluoro-phenoxy)phenyl]-1-[(3R)-piperidin-3-yl]-1H-pyrazolo[3,4-d]pyrimidin-4-amine (300 mg, 0.71 mmol, 1.00 equiv) in dichloromethane (30 mL), triethylamine (220 mg, 2.17 mmol, 3.0 equiv), HATU (400 mg, 1.05 mmol, 1.5 equiv), and 2-cyanoacetic acid (90 mg, 1.06 mmol, 1.5 equiv). The resulting solution was stirred for 10 h at 25° C., then washed with water and brine. The organics were dried over anhydrous sodium sulfate and concentrated. The residue was loaded onto a silica gel column and eluted with dichloromethane/methanol (10/1) to give. 230 mg (60%) of 3-[(3R)-3-[4-amino-3-[4-(2,6-difluorophenoxy)phenyl]-1H-pyrazolo[3,4-d]pyrimidin-1-yl]piperidin-1-yl]-3-oxopropanenitrile as a white solid.

Step 4

Into a 10 mL sealed tube, was placed a solution of 3-[(3R)-3-[4-amino-3-[4-(2,6-difluorophenoxy)phenyl]-1H-pyrazolo[3,4-d]pyrimidin-1-yl]piperidin-1-yl]-3-oxo-propanenitrile (150 mg, 0.31 mmol, 1.00 equiv) in methanol (5 mL), piperidine (78 mg, 0.92 mmol, 3.0 equiv), and cyclopropanecarbaldehyde (64 mg, 0.91 mmol, 3.0 equiv). The resulting solution was stirred for 12 h at 25° C. and then concentrated under vacuum. The residue was diluted with 10 mL of dichloromethane, and the solution was washed with saturated aqueous ammonium chloride, water and brine. The organics were dried over anhydrous sodium sulfate and concentrated. The residue was loaded onto a silica gel column and eluted with dichloromethane/methanol (20/1) to give 36 mg (21%) of 2-[[(3R)-3-[4-amino-3-[4-(2,6-difluorophenoxy)phenyl]-1H-pyrazolo[3,4-d]pyrimidin-1-yl]piperidin-1-yl]carbonyl]-3-cyclopropylprop-2-enenitrile as a white solid.

LC-MS: (ES, m/z): 542 [M+H].

Example 20

Synthesis of (R)-2-(3-(4-amino-3-(4-(3,5-difluorophenoxy)phenyl)-1H-pyrazolo[3,4-d]pyrimidin-1-yl)piperidine-1-carbonyl)-3-cyclopropylacrylonitrile

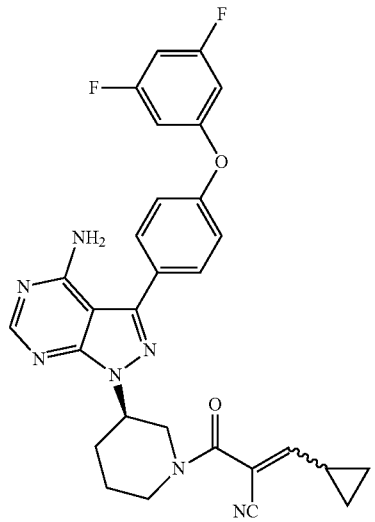 [SMILES: N#CC(=CC1CC1)C(=O)N1CCC[C@@H](n2nc(-c3ccc(Oc4cc(F)cc(F)c4)cc3)c3c(N)ncnc32)C1]

Step 1

Into a 100 mL 3-necked round-bottom flask purged and maintained under an inert atmosphere of nitrogen, was placed tert-butyl (3R)-3-[4-amino-3-iodo-1H-pyrazolo[3,4-d]pyrimidin-1-yl]piperidine-1-carboxylate (400 mg, 0.90 mmol, 1.00 equiv), 2-[4-(3,5-difluorophenoxy)phenyl]-4,4,5,5-tetramethyl-1,3,2-dioxaborolane (360 mg, 1.08 mmol, 1.20 equiv), sodium carbonate (190 mg, 1.79 mmol, 1.99 equiv), ethylene glycol dimethyl ether (50 mL), water (15 mL), and Pd(PPh3)4 (52 mg, 0.04 mmol, 0.05 equiv). The resulting solution was stirred for 12 h at 80° C. and then concentrated under vacuum. The residue was loaded onto a silica gel column and eluted with dichloromethane/methanol (100/1) to give 340 mg (72%) of tert-butyl (3R)-3-[4-amino-3-[4-(3,5-difluorophenoxy)phenyl]-1H-pyrazolo[3,4-d]pyrimidin-1-yl]piperidine-1-carboxylate as a yellow solid.

Step 2

Into a 100 mL round-bottom flask, was placed a solution of tert-butyl (3R)-3-[4-amino-3-[4-(3,5-difluorophenoxy)phenyl]-1H-pyrazolo[3,4-d]pyrimidin-1-yl]piperidine-1-carboxylate (340 mg, 0.65 mmol, 1.00 equiv) in dichloromethane (50 mL), followed by the addition of trifluoroacetic acid (10 mL) dropwise with stirring. The resulting solution was stirred for 12 h at room temperature and then concentrated under vacuum. The resulting solution was diluted with 20 mL of water. The pH value of the solution was adjusted to >7 with sodium carbonate and then extracted with dichloromethane and the organic layers combined and dried over anhydrous sodium sulfate and concentrated under vacuum to give 210 mg (76%) of 3-[4-(3,5-difluorophenoxy)phenyl]-1-[(3R)-piperidin-3-yl]-1H-pyrazolo[3,4-d]pyrimidin-4-amine as a brown solid.

Step 3

Into a 100-mL round-bottom flask, was placed a solution of 3-[4-(3,5-difluorophenoxy)phenyl]-1-[(3R)-piperidin-3-yl]-1H-pyrazolo[3,4-d]pyrimidin-4-amine (210 mg, 0.50 mmol, 1.00 equiv) in dichloromethane (50 mL), 2-cyanoacetic acid (63 mg, 0.74 mmol, 1.50 equiv), and 1-[(1H-imidazol-1-yl)carbonyl]-1H-imidazole (120 mg, 0.74 mmol, 1.50 equiv). The resulting solution was stirred for 24 h at room temperature and then diluted with dichloromethane. The resulting mixture was washed with NH4Cl and dried over anhydrous sodium sulfate and concentrated under vacuum. The residue was loaded onto a silica gel column and eluted with dichloromethane/methanol (100:1) to give 150 mg (62%) of 3-[(3R)-3-[4-amino-3-[4-(3,5-difluorophenoxy)phenyl]-1H-pyrazolo[3,4-d]pyrimidin-1-yl]piperidin-1-yl]-3-oxopropanenitrile as a white solid.

Step 4

Into a 50 mL round-bottom flask, was placed a solution of 3-[(3R)-3-[4-amino-3-[4-(3,5-difluorophenoxy)phenyl]-1H-pyrazolo[3,4-d]pyrimidin-1-yl]piperidin-1-yl]-3-oxopropanenitrile (150 mg, 0.31 mmol, 1.00 equiv) in methanol (20 mL), cyclopropanecarbaldehyde (64 mg, 0.91 mmol, 3.00 equiv), piperidine (13 mg, 0.15 mmol, 0.50 equiv), and dichloromethane (5 mL). The resulting solution was stirred for 12 h at room temperature and then concentrated under vacuum. The residue was loaded onto a silica gel column and eluted with dichloromethane/methanol (100:1) to give 70 mg (42%) of the title compound as a white solid. LC-MS: (ES, m/z): 542 [M+H]+.

Example 21

Synthesis of (R)-2-(3-(4-amino-3-(4-(2,5-difluorophenoxy)phenyl)-1H-pyrazolo[3,4-d]pyrimidin-1-yl)piperidine-1-carbonyl)-3-cyclopropylacrylonitrile

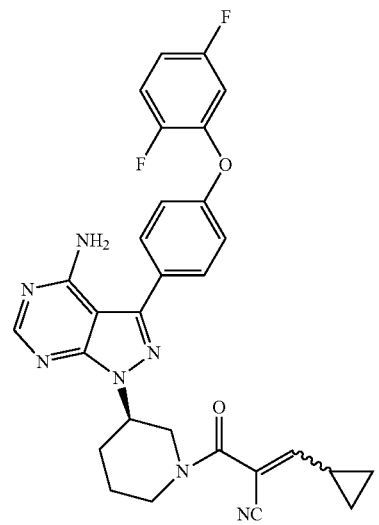 [SMILES: N#CC(=CC1CC1)C(=O)N1CCC[C@@H](n2nc(-c3ccc(Oc4cc(F)ccc4F)cc3)c3c(N)ncnc32)C1]

Step 1

Into a 500 mL 3-necked round-bottom flask, was placed a solution of sodium hydride (3.9 g, 162.50 mmol, 1.7 equiv) in N,N-dimethylformamide (200 mL). This was followed by the addition of a solution of 1-fluoro-4-nitrobenzene (13.6 g, 96.39 mmol, 1.00 equiv) in N,N-dimethylformamide (50 mL) dropwise with stirring at 0° C. over 20 min. The reaction mixture was stirred for 2 hr at 25° C. and then CuCl (9.6 g, 96.97 mmol, 1.0 equiv) was added, followed by addition of a solution of 2,5-difluorophenol (15.5 g, 119.15 mmol, 1.2 equiv) in N,N-dimethylformamide (50 mL) dropwise with stirring at 25° C. over 10 min. The resulting solution was stirred for 12 h at 100° C. in an oil bath and then diluted with water and washed with ether, water and brine. The reaction mixture was dried over anhydrous sodium sulfate and concentrated. The residue was loaded onto a silica gel column and eluted with ethyl acetate/petroleum ether (1/8) to give 19.5 g (81%) of 1,4-difluoro-2-(4-nitrophenoxy)benzene as a brown solid, Step 2

Into a 500 mL 3-necked round-bottom flask purged and maintained under an inert atmosphere of nitrogen, was placed a solution of 1,4-difluoro-2-(4-nitrophenoxy)benzene (19.5 g, 77.63 mmol, 1.00 equiv) in methanol (200 mL), and Raney Nickel (2 g). This was followed by the addition of a solution of hydrazine hydrate (11.66 g) in methanol (50 mL) dropwise with stirring at 25° C. over 15 min. The resulting solution was stirred for 12 h at 25° C. and then filtrated and the filtrate was concentrated under vacuum. The residue was diluted with ethyl acetate, washed with water and brine, dried over anhydrous sodium sulfate and concentrated under vacuum to give 16 g (93%) of 4-(2,5-difluorophenoxy) aniline as black oil.

Step 3

Into a 250 mL 4-necked round-bottom flask, was placed 4-(2,5-difluorophenoxy)-aniline (9 g, 40.69 mmol, 1.00 equiv), hydrogen chloride (37%) (10.2 g, 100 mmol, 2.5 equiv) and water (20 mL). A solution of NaNO2 (3.1 g, 44.93 mmol, 1.10 equiv) in water (10 mL) was added dropwise with stirring at 0° C. over 5 min. After stirring at 0° C. for 30 min., the mixture was added into a solution of NaI (18 g, 120.00 mmol, 3.0 equiv) in water (20 mL) dropwise with stirring at 25° C. The resulting solution was stirred for 12 h at 25° C. and then extracted with ethyl acetate and the organic layers combined. The combined organics were washed with water and brine, dried over anhydrous sodium sulfate and concentrated under vacuum to give 10.5 g (78%) of 1,4-difluoro-2-(4-iodophenoxy)benzene as brown oil.

Step 4

Into a 100 mL 3-necked round-bottom flask purged and maintained under an inert atmosphere of nitrogen, was placed a solution of 1,4-difluoro-2-(4-iodophenoxy)benzene (2 g, 6.02 mmol, 1.00 equiv) in N,N-dimethylformamide (50 mL), 4,4,5,5-tetramethyl-2-(tetramethyl-1,3,2-dioxaborolan-2-yl)-1,3,2-dioxaborolane (1.68 g, 6.62 mmol, 1.10 equiv), potassium acetate (1.76 g, 17.93 mmol, 3.0 equiv), and Pd(OAc)$_2$ (68 mg, 0.30 mmol, 0.05 equiv). The resulting solution was stirred for 12 h at 85° C. in an oil bath and then diluted with water. The resulting solution was extracted with ethyl acetate and the organic layers combined. The combined organics were washed with water and brine and dried over anhydrous sodium sulfate and concentrated. The residue was loaded onto a silica gel column and eluted with ethyl acetate/petroleum ether (1/8) to give 1.5 g (75%) of 2-[4-(2,5-difluorophenoxy)phenyl]-4,4,5,5-tetramethyl-1,3,2-dioxaborolane as a light yellow solid.

Step 5

Into a 250-mL 3-necked round-bottom flask purged and maintained under an inert atmosphere of nitrogen, was placed a solution of tert-butyl (3R)-3-[4-amino-3-iodo-1H-pyrazolo[3,4-d]pyrimidin-1-yl]piperidine-1-carboxylate (500 mg, 1.13 mmol, 1.00 equiv) in 1,4-dioxane/H$_2$O (100/30 mL), 2-[4-(2,5-difluorophenoxy)phenyl]-4,4,5,5-tetramethyl-1,3,2-dioxaborolane (420 mg, 1.26 mmol, 1.1 equiv), sodium carbonate (240 mg, 2.26 mmol, 2.0 equiv), and Pd(PPh$_3$)$_4$ (65 mg, 0.06 mmol, 0.05 equiv). The resulting solution was stirred for 12 h at 90° C. in an oil bath and then concentrated under vacuum. The residue was diluted with water and the resulting solution was extracted with dichloromethane and the organic layers were combined. The combined organics were washed with brine, dried over anhydrous sodium sulfate and concentrated. The residue was loaded onto a silica gel and eluted with dichloromethane/methanol (10/1) to give 510 mg (87%) of tert-butyl (3R)-3-[4-amino-3-[4-(2,5-difluorophenoxy)phenyl]-1H-pyrazolo[3,4-d]pyrimidin-1-yl]piperidine-1-carboxylate as a white solid.

Step 6

Into a 100 mL round-bottom flask, was placed a solution of tert-butyl (3R)-3-[4-amino-3-[4-(2,5-difluorophenoxy)phenyl]-1H-pyrazolo[3,4-d]pyrimidin-1-yl]piperidine-1-carboxylate (450 mg, 0.86 mmol, 1.00 equiv) in dichloromethane (40 mL). This was followed by the addition of CF$_3$COOH (10 mL) dropwise with stirring at 25° C. over 5 min. The resulting solution was stirred for 3 h at 25° C. and then concentrated under vacuum. The residue was diluted with dichloromethane and the resulting mixture was washed with aqueous sodium bicarbonate and brine and dried over anhydrous sodium sulfate and concentrated under vacuum to give 400 mg (99%) of 3-[4-(2,5-difluoro-phenoxy)phenyl]-1-[(3R)-piperidin-3-yl]-1H-pyrazolo[3,4-d]pyrimidin-4-amine as a white solid.

Step 7

Into a 100 mL round-bottom flask, was placed a solution of 3-[4-(2,5-difluoro-phenoxy)phenyl]-1-[(3R)-piperidin-3-yl]-1H-pyrazolo[3,4-d]pyrimidin-4-amine (300 mg, 0.71 mmol, 1.00 equiv) in dichloromethane (30 mL), HATU (400 mg, 1.05 mmol, 1.5 equiv), triethylamine (220 mg, 2.17 mmol, 3.0 equiv), and 2-cyanoacetic acid (90 mg, 1.06 mmol, 1.5 equiv). The resulting solution was stirred for 10 h at 25° C. and then washed with water and brine and dried over anhydrous sodium sulfate and concentrated. The residue was loaded onto a silica gel column and eluted with dichloromethane/methanol (10/1) to give 200 mg (58%) of 3-[(3R)-3-[4-amino-3-[4-(2,5-difluorophenoxy)phenyl]-1H-pyrazolo[3,4-d]pyrimidin-1-yl]piperidin-1-yl]-3-oxopropanenitrile as a white solid.

Step 8

Into a 10 mL sealed tube, was placed a solution of 3-[(3R)-3-[4-amino-3-[4-(2,5-difluorophenoxy)phenyl]-1H-pyrazolo[3,4-d]pyrimidin-1-yl]piperidin-1-yl]-3-oxopropanenitrile (150 mg, 0.31 mmol, 1.00 equiv) in methanol (5 mL), piperidine (78 mg, 0.92 mmol, 3.0 equiv), and cyclopropanecarbaldehyde (64 mg, 0.91 mmol, 3.0 equiv). The resulting solution was stirred for 12 h at 25° C. and then concentrated under vacuum. The resulting solution was diluted with dichloromethane and washed with saturated aqueous ammonium chloride, water and brine. The organics were dried over anhydrous sodium sulfate and concentrated. The residue was loaded onto a silica gel column and eluted with dichloromethane/methanol (20/1) to give 38 mg (23%) of 2-[[(3R)-3-[4-amino-3-[4-(2,5-difluorophenoxy)phenyl]-1H-pyrazolo[3,4-d]pyrimidin-1-yl]piperidin-1-yl]carbonyl]-3-cyclopropylprop-2-enenitrile as a white solid. LC-MS (ES, m/z): 542 [M+H].

Example 22

Synthesis of (R)-2-(3-(4-amino-3-(2-fluoro-4-(phenoxy)phenyl)-1H-pyrazolo[3,4-d]pyrimidin-1-yl)piperidine-1-carbonyl)-3-cyclopropylacrylonitrile

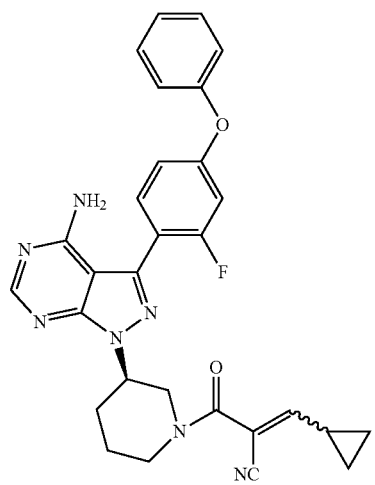 [SMILES: N#CC(=CC1CC1)C(=O)N1CCC[C@@H](n2nc(-c3ccc(Oc4ccccc4)cc3F)c3c(N)ncnc32)C1]

Step 1

Into a 100 mL 3-necked round-bottom flask purged and maintained under an inert atmosphere of nitrogen, was placed tert-butyl (3R)-3-[4-amino-3-iodo-1H-pyrazolo[3,4-d]pyrimidin-1-yl]piperidine-1-carboxylate (400 mg, 0.90 mmol, 1.00 equiv), (2-fluoro-4-phenoxyphenyl)boronic acid (250 mg, 1.08 mmol, 1.20 equiv), sodium carbonate (190 mg, 1.79 mmol, 1.99 equiv), ethylene glycol dimethyl ether (50 mL), water (15 mL), and Pd(PPh$_3$)$_4$ (52 mg, 0.04 mmol, 0.05 equiv). The resulting solution was stirred for 12 h at 80° C. and then concentrated under vacuum. The residue was loaded onto a silica gel column and eluted with dichloromethane/methanol (100/1) to give 320 mg (70%) of tert-butyl (3R)-3-[4-amino-3-(2-fluoro-4-phenoxyphenyl)-1H-pyrazolo[3,4-d]pyrimidin-1-yl]piperidine-1-carboxylate as a yellow solid.

Step 2

Into a 100 mL round-bottom flask, was placed a solution of tert-butyl (3R)-3-[4-amino-3-(2-fluoro-4-phenoxyphenyl)-1H-pyrazolo[3,4-d]pyrimidin-1-yl]piperidine-1-carboxylate (320 mg, 0.63 mmol, 1.00 equiv) in dichloromethane (50 mL). This was followed by the addition of trifluoroacetic acid (10 mL) dropwise with stirring. The resulting solution was stirred overnight at room temperature and then concentrated under vacuum. The residue was diluted with water and the pH value of the solution was adjusted to >7 with sodium carbonate. The resulting solution was extracted with dichloromethane and the organic layers combined and dried over anhydrous sodium sulfate and concentrated under vacuum to give 190 mg (74%) of 3-(2-fluoro-4-phenoxyphenyl)-1-[(3R)-piperidin-3-yl]-1H-pyrazolo[3,4-d]pyrimidin-4-amine as a brown solid.

Step 3

Into a 100 mL round-bottom flask, was placed a solution of 3-(2-fluoro-4-phenoxyphenyl)-1-[(3R)-piperidin-3-yl]-1H-pyrazolo[3,4-d]pyrimidin-4-amine (190 mg, 0.47 mmol, 1.00 equiv) in dichloromethane (50 mL), 2-cyanoacetic acid (60 mg, 0.71 mmol, 1.50 equiv), and 1-[(1H-imidazol-1-yl)carbonyl]-1H-imidazole (114 mg, 0.70 mmol, 1.50 equiv). The resulting solution was stirred for 24 h at room temperature and then diluted with dichloromethane. The resulting mixture was washed with NH$_4$Cl and dried over anhydrous sodium sulfate and concentrated under vacuum. The residue was loaded onto a silica gel column and eluted with dichloromethane/methanol (100:1) to give 100 mg (45%) of 3-[(3R)-3-[4-amino-3-(2-fluoro-4-phenoxyphenyl)-1H-pyrazolo[3,4-d]pyrimidin-1-yl]piperidin-1-yl]-3-oxopropanenitrile as a white solid.

Step 4

Into a 50 mL round-bottom flask, was placed a solution of 3-[(3R)-3-[4-amino-3-(2-fluoro-4-phenoxyphenyl)-1H-pyrazolo[3,4-d]pyrimidin-1-yl]piperidin-1-yl]-3-oxopropanenitrile (100 mg, 0.21 mmol, 1.00 equiv) in methanol (20 mL), cyclopropanecarbaldehyde (45 mg, 0.64 mmol, 3.00 equiv), piperidine (9 mg, 0.11 mmol, 0.50 equiv), and dichloromethane (5 mL). The resulting solution was stirred for 12 h at room temperature and then concentrated under vacuum. The residue was loaded onto a silica gel column and eluted with dichloromethane/methanol (100:1) to give 24 mg (24%) of the title compound as a white solid, LC-MS (ES, m/z): 524 [M+H]$^+$.

Proceeding as described above, but substituting cyclopropanecarbaldehyde with acetaldehyde, (R)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile was synthesized.

Example 23

Synthesis of (R)-2-(2-((4-amino-3-(4-(2-fluorophenoxy)phenyl)-1H-pyrazolo[3,4-d]pyrimidin-1-yl)methyl)pyrrolidine-1-carbonyl)-3-cyclopropylacrylonitrile

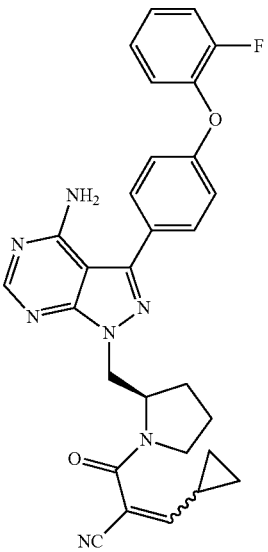 [SMILES: N#CC(=CC1CC1)C(=O)N1CCC[C@@H]1Cn1nc(-c2ccc(Oc3ccccc3F)cc2)c2c(N)ncnc21]

Step 1

Into a 100 mL 3-necked round-bottom flask, was placed a solution of 2-fluorophenol (2.6 g, 23.19 mmol, 1.00 equiv) in N,N-dimethylformamide (30 mL) and CuCl (2.2 g, 2.41 equiv). This was followed by the addition of sodium hydride (1.34 g, 55.83 mmol, 0.86 equiv) in portions and then 1-fluoro-4-nitrobenzene (2.8 g, 19.84 mmol, 0.67 equiv). The resulting solution was stirred for 5 h at 100° C. in an oil bath and the resulting solution was diluted with water/ice. The aqueous mixture was extracted with ethyl acetate and the organic layers combined and dried over anhydrous sodium sulfate, and concentrated under vacuum. The residue was loaded onto a silica gel column and elution with ethyl acetate/petroleum ether (1:100) gave 1.7 g (31%) of 1-(2-fluorophenoxy)-4-nitrobenzene as a light yellow solid.

Step 2

Into a 250 mL 3-necked round-bottom flask, was placed a solution of 1-fluoro-2-(4-nitrophenoxy)benzene (5 g, 21.44 mmol, 1.00 equiv) in methanol/H$_2$O (2/1=V/V) (100 mL), and NH$_4$Cl (1 g, 18.70 mmol, 0.87 equiv). This was followed by the addition of Fe (7 g, 5.83 equiv), in portions at 80° C. in 20 min. The resulting solution was stirred for 1 h at reflux in an oil bath. The reaction mixture was cooled in a water bath. The solids were filtered out and the filtrate was concentrated under vacuum. The resulting solution was extracted with ethyl acetate and the organic layers combined and dried over anhydrous sodium sulfate and concentrated under vacuum to give 3.2 g (73%) of 4-(2-fluorophenoxy)aniline as a light yellow solid.

Step 3

Into a 250 mL 3-necked round-bottom flask, was placed 4-(2-fluorophenoxy)aniline (2 g, 9.84 mmol, 1.00 equiv) and 37% hydrogen chloride (20 mL). NaNO$_2$ (800 mg, 11.59 mmol, 1.18 equiv) was added in portions at 0° C. The mixture was stirred at 0° C. for 30 min and then urea (1 g, 16.65 mmol, 1.69 equiv) was added. The mixture was stirred at 0° C. for 20 min and poured into the solution of KI (10 g) in water (20 mL) at room temperature. The resulting solution was stirred at room temperature for 1 h and extracted with ethyl acetate and the organic layers combined and dried over anhydrous sodium sulfate and concentrated under vacuum. The residue was loaded onto a silica gel column and eluted with ethyl acetate/petroleum ether (1:100; 1:50) to give 1 g (32%) of 1-fluoro-2-(4-iodophenoxy)-benzene as a light yellow solid.

Step 4

Into a 100 mL 3-necked round-bottom flask purged and maintained under an inert atmosphere of nitrogen, was placed a solution of 1-(2-fluorophenoxy)-4-iodobenzene (3.3 g, 10.51 mmol, 1.00 equiv) in tetrahydrofuran (50 mL). n-BuLi (4.4 mL) was added dropwise with stirring at −78° C. The resulting solution was stirred for 10 mins at −78° C. and then tris(propan-2-yl)borate (2.1 g, 11.17 mmol, 1.06 equiv) was added dropwise with stirring at −78° C. over 10 min. The resulting solution was stirred while the temperature warmed from −78° C. to room temperature. The reaction was then quenched by the addition of saturated aqueous $NH_4Cl$ and concentrated under vacuum. The resulting solution was diluted with 10% aquious potassium hydroxide and then washed with ether. The pH of the aqueous was adjusted to 2-4 with hydrogen chloride (37%). The resulting solution was extracted with ethyl acetate and the organic layers combined and dried over anhydrous sodium sulfate and concentrated under vacuum to give 2.2 g (90%) of [4-(2-fluorophenoxy)phenyl]boronic acid as a white solid Step 5

Into a 100 mL 3-necked round-bottom flask purged and maintained under an inert atmosphere of nitrogen, was placed a solution of tert-butyl (2R)-2-([4-amino-3-iodo-1H-pyrazolo[3,4-d]pyrimidin-1-yl]methyl)pyrrolidine-1-carboxylate (300 mg, 0.68 mmol, 1.00 equiv) in dioxane/$H_2O$ (7/3=V/V) (30 mL), [4-(2-fluorophenoxy)phenyl]boronic acid (500 mg, 2.16 mmol, 3.19 equiv), sodium carbonate (500 mg, 4.72 mmol, 6.99 equiv), and $Pd(PPh_3)_4$ (200 mg, 0.17 mmol, 0.26 equiv). The resulting solution was stirred overnight at 100° C. in an oil bath and then concentrated under vacuum. The residue was loaded onto a silica gel column with dichloromethane/methanol (100:1) to give 0.2 g (59%) of tert-butyl (2S)-2-([4-amino-3-[4-(2-fluorophenoxy)phenyl]-1H-pyrazolo[3,4-d]pyrimidin-1-yl]methyl)-pyrrolidine-1-carboxylate as a light yellow solid.

Step 6

Into a 100 mL round-bottom flask purged and maintained under an inert atmosphere of nitrogen, was placed a solution of tert-butyl (2R)-2-([4-amino-3-[4-(2-fluorophenoxy)phenyl]-1H-pyrazolo[3,4-d]pyrimidin-1-yl]methyl)pyrrolidine-1-carboxylate (200 mg, 0.40 mmol, 1.00 equiv) in dichloromethane (20 mL), and trifluoroacetic acid (10 g, 87.70 mmol, 221.25 equiv). The resulting solution was stirred overnight at room temperature and then concentrated under vacuum. The resulting solution was diluted with 10% aqueous sodium carbonate and the solution was extracted with dichloromethane and the organic layers combined and dried over anhydrous sodium sulfate and concentrated under vacuum to give 0.1 g (62%) of 3-[4-(2-fluorophenoxy)phenyl]-1-((2R)-pyrrolidin-2-ylmethyl)-1H-pyrazolo[3,4-d]pyrimidin-4-amine as a light yellow solid.

Step 7

Into a 50 mL round-bottom flask, was placed a solution of 3-[4-(2-fluorophenoxy)phenyl]-1-((2R)-pyrrolidin-2-ylmethyl)-1H-pyrazolo[3,4-d]pyrimidin-4-amine (100 mg, 0.25 mmol, 1.00 equiv) in dichloromethane (10 mL), 1-[(1H-imidazol-1-yl)carbonyl]-1H-imidazole (80 mg, 0.49 mmol, 1.25 equiv), and 2-cyanoacetic acid (50 mg, 0.59 mmol, 3.80 equiv). The resulting solution was stirred for 1 h at room temperature and then concentrated under vacuum. The residue was loaded onto a silica gel column with dichloromethane/methanol (100:1; 50:1) to give 0.05 g (43%) of 3-[(2R)-2-([4-amino-3-[4-(2-fluorophenoxy)phenyl]-1H-pyrazolo[3,4-d]pyrimidin-1-yl]methyl)pyrrolidin-1-yl]-3-oxopropanenitrile as a light yellow solid.

Step 8

Into a 50 mL round-bottom flask, was placed a solution of 3-[(2R)-2-([4-amino-3-[4-(2-fluorophenoxy)phenyl]-1H-pyrazolo[3,4-d]pyrimidin-1-yl]methyl)pyrrolidin-1-yl]-3-oxopropanenitrile (50 mg, 0.11 mmol, 1.00 equiv) in methanol (10 mL), piperidine (50 mg, 0.59 mmol, 6.73 equiv), and cyclopropanecarbaldehyde (50 mg, 0.71 mmol, 5.54 equiv). The resulting solution was stirred for 1 h at room temperature and then concentrated under vacuum. The residue was loaded onto a silica gel column and eluted with dichloromethane/methanol (100:1, 50:1) to give 0.0179 g (32%) of the title compounds as an off-white solid.

LC-MS (ES, m/z): 524 [M+H]$^+$.

Example 24

Synthesis of (S)-4-amino-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile bis(2,2,2-trifluoroacetate

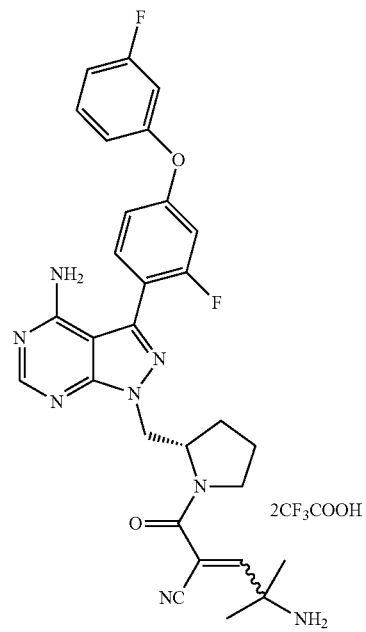 [SMILES: CC(C)(N)C=C(C#N)C(=O)N1CCC[C@H]1Cn1nc(-c2ccc(Oc3cccc(F)c3)cc2F)c2c(N)ncnc21]

Step 1

To a solution of 3-((S)-2-((4-amino-3-(2-fluoro-4-(3-fluorophenoxy)phenyl)-1H-pyrazolo[3,4-d]pyrimidin-1-yl)methyl)pyrrolidin-1-yl)-3-oxopropanenitrile (245 mg, 0.5 mmol, 1 equiv) and tert-butyl 2-methyl-1-oxopropan-2-ylcarbamate (935 mg, 5 mmol, 10 equiv) in dioxane (30 mL) was added 0.5 mL piperidine, 1 drop AcOH and 2 g of 4 A molecular sieves. The resulting mixture was stirred for 6 h at 110° C. The solids was filtered out, the filtrate was diluted with 200 mL of ethyl acetate, washed with brine, dried over $Na_2SO_4$, concentrated and purified with silica gel column (ethyl acetate/MeOH 10/1) to give 60 mg of tert-butyl 5-((S)-2-((4-amino-3-(2-fluoro-4-(3-fluorophenoxy)phenyl)-1H-pyrazolo[3,4-d]pyrimidin-1-yl)methyl)pyrrolidin-1-yl)-4-cyano-2-methyl-5-oxopent-3-en-2-ylcarbamate as white solid.

Step 2

To a solution of tert-butyl 5-((S)-2-((4-amino-3-(2-fluoro-4-(3-fluorophenoxy)phenyl)-1H-pyrazolo[3,4-d]pyrimidin-1-yl)methyl)pyrrolidin-1-yl)-4-cyano-2-methyl-5-oxopent-3-en-2-ylcarbamate (60 mg, 0.091 mmol) in DCM (20 mL) was added CF$_3$COOH (5 mL). The mixture was stirred for 2 h at room temperature and then concentrated and purified on Prep-HPLC. Conditions: (1#-Pre-HPLC-001(SHIMADZU)): Column, SunFire Prep C18, 19*150 mm 5 um; mobile phase, water with 0.05% TFA and CH$_3$CN (40% CH$_3$CN up to 100% in 20 min); Detector, 254 nm to give 12 mg of the title compound as light yellow solid.

LC-MS: m/z 559 (M+H$^+$).

Example 25

Synthesis of 2-((S)-2-((4-amino-3-(2-fluoro-4-phenoxyphenyl)-1H-pyrazolo[3,4-d]pyrimidin-1-yl)methyl)pyrrolidine-1-carbonyl)-4-methyl-4-(methylamino)pent-2-enenitrile bis(2,2,2-trifluoroacetate

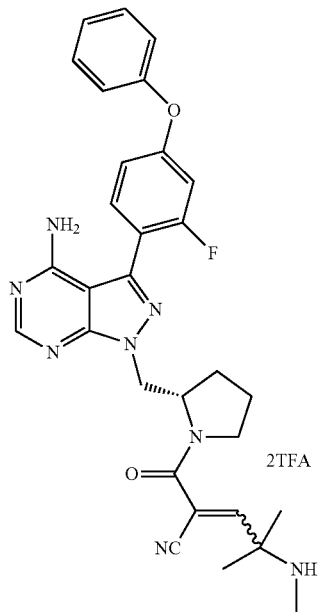 [SMILES: CNC(C)(C)C=C(C#N)C(=O)N1CCC[C@H]1Cn1nc(-c2ccc(Oc3ccccc3)cc2F)c2c(N)ncnc21]

Step 1

To a solution of 3-((S)-2-((4-amino-3-(2-fluoro-4-phenoxyphenyl)-1H-pyrazolo[3,4-d]pyrimidin-1-yl)methyl)pyrrolidin-1-yl)-3-oxopropanenitrile (236 mg, 0.5 mmol, 1 equiv) and tert-butyl methyl(2-methyl-1-oxopropan-2-yl)carbamate (2.01 g, 10 mmol, 20 equiv) in dioxane (30 mL) was added 0.5 mL piperidine, 1 drop AcOH and 2 g of 4 A molecular sieves. The resulting mixture was stirred for 6 h at 110° C. The solids was filtered out, the filtrate was diluted with 50 mL of EA, washed with brine, dried over Na$_2$SO$_4$, concentrated. The residue was purified on silica gel column (EA to EA/MeOH 10/1) to give 60 mg of tert-butyl 5-((S)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl(methyl)carbamate as white solid.

Step 2

To a solution of tert-butyl 5-((S)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl(methyl)carbamate (60 mg, 0.092 mmol) in DCM (5 mL) was added 1.5 mL of CF$_3$COOH. The mixture was stirred for 2 h at room temperature, concentrated and the residue was purified on Prep-HPLC. Conditions: (1#-Pre-HPLC-001(SHIMADZU)): Column, SunFire Prep C18, 19*150 mm 5 um; mobile phase, water with 0.05% TFA and CH$_3$CN (40% CH$_3$CN up to 100% in 20 min); Detector, 254 nm to give 12 mg of the title compound salt as a white solid.

LC-MS: m/z 555 (M+H$^+$).

Example 26

Synthesis of (S)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-3-cyclopropylacrylonitrile trifluoroacetic

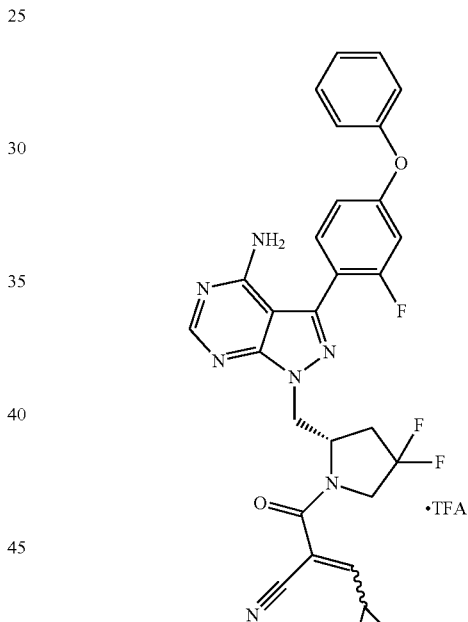

Step 1

Into a solution of 1-tert-butyl 2-methyl (2S)-4,4-difluoropyrrolidine-1,2-dicarboxylate (900 mg, 3.39 mmol, 1.00 equiv) in tetrahydrofuran (15 mL) was added LiBH$_4$ (200 mg, 9.1 mmol, 2.7 equiv) in batches at 0° C. The resulting solution was stirred overnight at room temperature, then was diluted with EA and washed with water and brine, dried over anhydrous sodium sulfate and concentrated to give 0.8 g of tert-butyl (2S)-4,4-difluoro-2-(hydroxymethyl) pyrrolidine-1-carboxylate as reddish oil.

Step 2

Under nitrogen, to a solution of 3-iodo-1H-pyrazolo[3,4-d]pyrimidin-4-amine (2.61 g, 10.00 mmol, 1.00 equiv), tert-butyl (2S)-4,4-difluoro-2-(hydroxymethyl)pyrrolidine-1-carboxylate (2.37 g, 9.99 mmol, 1.00 equiv) and TPP (4 g, 15.2 mmol, 1.50 equiv) in THF was DIAD (3.00 g, 15.0 mmol, 1.50 equiv) at 0° C. in 30 min. The resulting solution was stirred overnight at room temperature. The mixture was then concentrated under vacuum and the residue was applied onto a silica gel column with dichloromethane/ethyl acetate (3/1) to give 1 g of tert-butyl (2S)-2-([4-amino-3-iodo-1H-pyrazolo[3,4-d]-pyrimidin-1-yl]methyl)-4,4-difluoropyrrolidine-1-carboxylate as reddish oil.

Step 3

Under nitrogen atmosphere, a suspension of tert-butyl (2S)-2-([4-amino-3-iodo-1H-pyrazolo[3,4-d]pyrimidin-1-yl]methyl)-4,4-difluoropyrrolidine-1-carboxylate (800 mg, 1.67 mmol, 1.00 equiv), (2-fluoro-5-phenoxyphenyl)boronic acid (480 mg, 2.07 mmol, 1.20 equiv), Pd(dppf)Cl$_2$ (140 mg, 0.17 mmol, 0.10 equiv), sodium carbonate (0.53 g, 5.00 mmol, 3.00 equiv) in 1,4-dioxane/water (40/10 mL) was stirred at 80° C. overnight. The resulting mixture was concentrated under vacuum. The residue was loaded on a silica gel column and eluted with ethyl acetate/petroleum ether (1:2 to 3:1) to give 0.6 g (67%) of tert-butyl (2S)-2-[[4-amino-3-(2-fluoro-4-phenoxyphenyl)-1H-pyrazolo[3,4-d]pyrimidin-1-yl]methyl]-4,4-difluoropyrrolidine-1-carboxylate as a reddish solid.

Step 4

To a solution of tert-butyl (2S)-2-[[4-amino-3-(2-fluoro-4-phenoxyphenyl)-1H-pyrazolo[3,4-d]pyrimidin-1-yl]methyl]-4,4-difluoropyrrolidine-1-carboxylate (600 mg, 1.11 mmol, 1.00 equiv) in dichloromethane (10 mL) was added trifluoroacetic acid (2 mL) dropwise. The resulting solution was stirred at room temperature for 2 h. The mixture was concentrated under vacuum to give 0.85 g (crude) of 1-[[(2S)-4,4-difluoropyrrolidin-2-yl]methyl]-3-(2-fluoro-4-phenoxyphenyl)-1H-pyrazolo[3,4-d]pyrimidin-4-amine trifluoroacetic acid salt as a brown semi-solid.

Step 5

To a solution of 1-[[(2S)-4,4-difluoropyrrolidin-2-yl]methyl]-3-(2-fluoro-4-phenoxyphenyl)-1H-pyrazolo[3,4-d]pyrimidin-4-amine (850 mg, crude), 2-cyanoacetic acid (120 mg, 1.31 mmol, 1.29 equiv) and TEA (650 mg, 6.45 mmol, 5.00 equiv) in dichloromethane (30 mL), was added HATU (500 mg, 1.32 mmol, 1.29 equiv). The resulting solution was stirred at room temperature overnight. The mixture was diluted with DCM, washed with HCl (2N), sat. NaHCO$_3$, brine, dried over sodium sulfate and concentrated. The residue was submitted to chromatography (SiO$_2$, DCM:MeOH=30:1) to give 0.4 g (77%) of 3-[(2S)-2-[[4-amino-3-(2-fluoro-4-phenoxyphenyl)-1H-pyrazolo[3,4-d]pyrimidin-1-yl]methyl]-4,4-difluoropyrrolidin-1-yl]-3-oxopropanenitrile as a pale yellow solid.

Step 6

A solution of 3-[(2S)-2-[[4-amino-3-(2-fluoro-4-phenoxyphenyl)-1H-pyrazolo[3,4-d]pyrimidin-1-yl]methyl]-4,4-difluoropyrrolidin-1-yl]-3-oxopropanenitrile (120 mg, 0.24 mmol, 1.00 equiv), cyclopropanecarbaldehyde (80 mg, 1.14 mmol, 5.00 equiv), piperidine (41 mg, 0.48 mmol, 2.00 equiv) in ethanol (10 mL) was stirred at 70° C. for 2 h. The resulting mixture was concentrated under vacuum. The residue was purified on Prep-HPLC. Conditions: (1#-Pre-HPLC-001(SHIMADZU)): Column, SunFire Prep C18, 19*150 mm 5 um; mobile phase, water with 0.05% TFA and CH$_3$CN (40% CH$_3$CN up to 100% in 20 min); Detector, 254 nm, to give 24 mg (18%) of the title compound as a white solid.

LC-MS m/z: 560 (M+1).

Example 27

Synthesis of (R)-2-(3-(4-amino-5-(4-phenoxyphenyl)-7H-pyrrolo[2,3-d]pyrimidin-7-yl)piperidine-1-carbonyl)-3-cyclopropylacrylonitrile

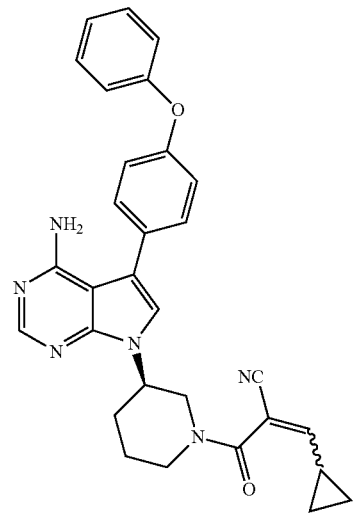 [SMILES: N#CC(=CC1CC1)C(=O)N1CCC[C@@H](n2cc(-c3ccc(Oc4ccccc4)cc3)c3c(N)ncnc32)C1]

Step 1

To the solution of 4-chloro-7H-pyrrolo[2,3-d]pyrimidine (10 g, 65.12 mmol, 1.0 eq) and (S)-tert-butyl 3-hydroxypiperidine-1-carboxylate (13.0 g, 65.12 mmol, 1.0 eq) and PPh$_3$ (34.20 g, 130.24 mmol, 2.0 eq) in THF (400 mL), DEAD (22.68 g, 130.24 mmol, 2.0 eq) was added at 0° C. The resulted mixture was stirred and warmed to RT for 12 h. The reaction mixture was purified by column (10% EtOAc in petroleum ether) to afford (R)-tert-butyl 3-(4-chloro-7H-pyrrolo[2,3-d]pyrimidin-7-yl)piperidine-1-carboxylate (2.1 g, 10% in yield) as colorless oil.

Step 2

A mixture of (R)-tert-butyl 3-(4-chloro-7H-pyrrolo[2,3-d]pyrimidin-7-yl)piperidine-1-carboxylate (1.7 g, 5.05 mmol) and NIS (1.25 g, 5.55 mmol) in DMF (20 mL) was stirred for 12 h at room temperature. Water was added to the mixture, which was extracted with EA, the combined organic layers were dried and purified by column to give (R)-tert-butyl 3-(4-chloro-5-iodo-7H-pyrrolo[2,3-d]pyrimidin-7-yl)piperidine-1-carboxylate (2.0 g, 86% in yield).

Step 3

A solution of (R)-tert-butyl 3-(4-chloro-5-iodo-7H-pyrrolo[2,3-d]pyrimidin-7-yl) piperidine-1-carboxylate (2.0 g, 4.32 mmol) in IPA saturated with NH$_3$ (20 mL) was stirred at 100° C. for 12 h in a 100 mL of autoclave. The organic layer was concentrated and purified on silica gel chromatography (eluted with PE:EtOAc=1:1) to afford (R)-tert-butyl 3-(4-amino-5-iodo-7H-pyrrolo[2,3-d]pyrimidin-7-yl) piperidine-1-carboxylate (1.5 g, 78% in yield).

Step 4

A mixture of (R)-tert-butyl 3-(4-amino-5-iodo-7H-pyrrolo[2,3-d]pyrimidin-7-yl)piperidine-1-carboxylate (250 mg, 0.56 mmol), 4-phenoxyphenylboronic acid (133 mg, 0.62 mmol), Pd(PPh$_3$)$_4$ (100 mg) and Na$_2$CO$_3$ (150 mg, 1.41 mmol) in dioxane/H$_2$O (40/10 ml) was stirred at 100° C. for 4 h. The reaction mixture was concentrated and purified by Pre-TLC to obtain (R)-tert-butyl 3-(4-amino-5-(4-phenoxyphenyl)-7H-pyrrolo[2,3-d]pyrimidin-7-yl)piperidine-1-carboxylate (150 mg, 55% in yield).

Step 5

To a mixture of (R)-tert-butyl 3-(4-amino-5-(4-phenoxyphenyl)-7H-pyrrolo[2,3-d]pyrimidin-7-yl)piperidine-1-carboxylate (150 mg, 0.31 mmol) in 10 ml DCM was added TFA (10 ml). The reaction mixture was stirred at RT for 2 h. Solvent was removed and sat. NaHCO$_3$ (10 mL) was added. The resulting mixture was extracted with DCM. The organic layer was dried and concentrated to afford (R)-5-(4-phenoxyphenyl)-7-(piperidin-3-yl)-7H-pyrrolo[2,3-d]pyrimidin-4-amine (100 mg, 83% in yield), which was subjected to the next step without any further purification.

Step 6

To a mixture of (R)-5-(4-phenoxyphenyl)-7-(piperidin-3-yl)-7H-pyrrolo[2,3-d]pyrimidin-4-amine (100 mg, 0.26 mmol, 1.0 eq), 2-cyano-3-cyclopropylacrylic acid (45 mg, 0.32 mmol, 1.2 eq) and DIPEA (102 mg, 0.78 mmol, 3 eq) in 10 mL DCM was added HATU (150 mg, 0.40 mmol, 1.5 eq) and the reaction mixture was stirred for 4 h at RT under N$_2$. The reaction mixture was purified by Pre-TLC to give the title compound (60 mg, 54% in yield). LCMS: m/z (505.0) (M+H)$^+$ $^1$HNMR (400 MHz, CDCl$_3$): δ 0.826-0.837 (m, 2H), 1.147~1.183 (m, 6H), 1.744~2.210 (m, 5H), 4.661~4.699 (m, 1H), 5.212~5.226 (m, 2H), 6.499~6.524 (m, 1H), 6.921~7.367 (m, 10H) and 8.223 (S, 1H).

Proceeding as described above but substituting 4-phenoxyphenylboronic acid with 2-(2-fluoro-4-phenoxyphenyl)-4,4,5,5-tetramethyl-1,3,2-dioxaborolane and 2-(4-(3,5-difluorophenoxy)phenyl)-4,4,5,5-tetramethyl-1,3,2-dioxaborolane, (R)-2-(3-(4-amino-5-(2-fluoro-4-phenoxyphenyl)-7H-pyrrolo[2,3-d]pyrimidin-7-yl) piperidine-1-carbonyl)-3-cyclopropylacrylonitrile LCMS m/z 523.1 (M+H)$^+$ and (R)-2-(3-(4-amino-5-(4-(3,5-difluorophenoxy)phenyl)-7H-pyrrolo[2,3-d]pyrimidin-7-yl)piperidine-1-carbonyl)-3-cyclopropylacrylonitrile LCMS m/z 541.1 (M+H)$^+$ were prepared respectively.

Example 28

Synthesis of (S)-2-{2-[4-amino-5-(4-phenoxy-phenyl)-pyrrolo[2,3-d]pyrimidin-7-ylmethyl]-pyrrolidine-1-carbonyl}-3-cyclopropyl-acrylonitrile

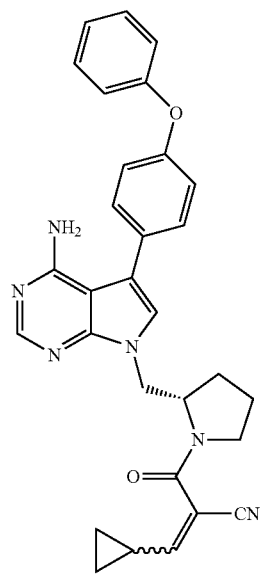 [SMILES: N#CC(=CC1CC1)C(=O)N1CCC[C@H]1Cn1cc(-c2ccc(Oc3ccccc3)cc2)c2c(N)ncnc21]

Step 1

To a solution of 4-chloro-7H-pyrrolo[2,3-d]pyrimidine (8.0 g, 52.32 mmol, 1.0 eq) in DMF (40 mL), NIS (15.7 g, 57.55 mmol, 1.1 eq) was added at 0° C. The reaction mixture was stirred overnight at room temperature. Water (40 mL) was added to the reaction mixture, extracted with EtOAc. The organic layer was dried over Na$_2$SO$_4$ and concentrated under vacuum to give 4-chloro-5-iodo-7H-pyrrolo[2,3-d]pyrimidine (14.6 g, 100% in yield).

Step 2

To a solution of 4-chloro-5-iodo-7H-pyrrolo[2,3-d]pyrimidine (4.0 g, 14.34 mmol, 1.0 eq), (S)-tert-butyl 2-(hydroxymethyl)pyrrolidine-1-carboxylate (4.04 g, 20.08 mmol, 1.4 eq), and PPh$_3$ (7.5 g, 28.68 mmol, 2.0 eq) in dry THF (30 mL), DIAD (5.80 g, 28.68 mmol, 2.0 eq) was added dropwise at 0° C. The mixture was stirred at RT for 5 h. The reaction mixture was concentrated and purified by silica gel chromatography (eluted with PE: EtOAc=1:1) to afford (S)-2-(4-chloro-5-iodo-pyrrolo[2,3-d]pyrimidin-7-ylmethyl)-pyrrolidine-1-carboxylic acid tert-butyl ester (5.1 g, 77% in yield).

Step 3

A solution of (S)-2-(4-chloro-5-iodo-pyrrolo[2,3-d]pyrimidin-7-ylmethyl)-pyrrolidine-1-carboxylic acid tert-butyl ester (3.5 g, 6.93 mmol) in MeOH (saturated with NH$_3$) was stirred 100° C. and overnight in a 100 mL of sealed tube. The organic layer was concentrated under reduced pressure to provide a white solid which was purified by silica gel chromatography eluted with PE: EtOAc=1:1 to afford (S)-2-(4-amino-5-iodo-pyrrolo[2,3-d]pyrimidin-7-ylmethyl)-pyrrolidine-1-carboxylic acid tert-butyl ester (2.7 g, 87.98% in yield).

Step 4

A solution of (S)-2-(4-amino-5-iodo-pyrrolo[2,3-d]pyrimidin-7-ylmethyl)-pyrrolidine-1-carboxylic acid tert-butyl ester (500.00 mg, 1.13 mmol, 1.0 eq), 4-phenoxyphenylboronic acid (240.00 mg, 1.13 mmol, 1.0 eq), Pd(PPh$_3$)$_4$ (100.00 mg), and Na$_2$CO$_3$ (300.00 mg, 2.83 mmol, 2.5 eq) in Dioxane/H$_2$O (40/10 ml) was stirred at 90° C. for 4 h. The reaction mixture was concentrated and purified by Pre-TLC to afford (S)-2-[4-amino-5-(4-phenoxy-phenyl)-pyrrolo[2,3-d]pyrimidin-7-ylmethyl]-pyrrolidine-1-carboxylic acid tert-butyl ester (500 mg, 91% in yield).

Step 5

To a solution of (S)-2-[4-amino-5-(4-phenoxy-phenyl)-pyrrolo[2,3-d]pyrimidin-7-ylmethyl]-pyrrolidine-1-carboxylic acid tert-butyl ester (500 mg, 1.03 mmol) in 10 ml of DCM, TFA (10 ml) was added. The reaction mixture was stirred at RT for 2 h. The mixture was concentrated to give (S)-5-(4-phenoxyphenyl)-7-pyrrolidin-2-ylmethyl-7H-pyrrolo[2,3-d]pyrimidin-4-ylamine (400 mg), which was subjected to the next step without any further purification.

Step 6

To a mixture of (S)-5-(4-phenoxy-phenyl)-7-pyrrolidin-2-ylmethyl-7H-pyrrolo[2,3-d]pyrimidin-4-ylamine (100 mg, 0.26 mmol, 1.0 eq), 2-cyano-3-cyclopropyl-acrylic acid (45 mg, 0.32 mmol, 1.2 eq) and DIEA (102 mg, 0.78 mmol, 3.0 eq) in 10 ml DCM was added HATU (150 mg, 0.40 mmol, 1.5 eq). The reaction mixture was stirred for 4 h at RT under N$_2$. The mixture was purified by Pre-TLC to give the title compound (71 mg). LCMS: m/z 486.2 (M+H)$^+$ Proceeding as described above but substituting 4-phenoxyphenylboronic acid with 3,5-difluoro-phenoxyphenyl-boronic acid and 2-fluoro-4-phenoxyphenyl-bronic acid, (S)-2-(2-{4-amino-5-[4-(3,5-difluoro-phenoxy)-phenyl]-pyrrolo[2,3-d]pyrimidin-7-ylmethyl}-pyrrolidine-1-carbonyl)-3-cyclopropyl-acrylonitrile LCMS m/z m/z 541.1

(M+H)+ and (S)-2-{2-[4-amino-5-(2-fluoro-4-phenoxy-phenyl)-pyrrolo[2,3-d]pyrimidin-7-ylmethyl]-pyrrolidine-1-carbonyl}-3-cyclopropyl-acrylonitrile LCMS m/z 523.2 (M+H)+ were prepared respectively.

Example 29

Synthesis of (S)-2-(2-((4-amino-6-methyl-5-(4-phenoxyphenyl)-7H-pyrrolo[2,3-d]pyrimidin-7-yl)methyl)pyrrolidine-1-carbonyl)-3-cyclopropylacrylonitrile

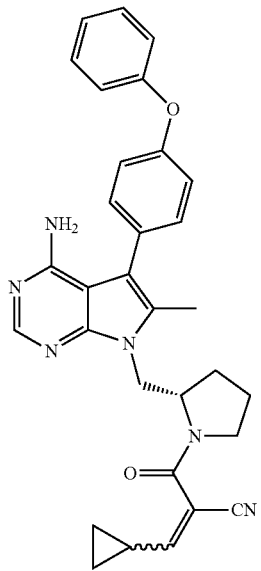 [SMILES: Cc1c(-c2ccc(Oc3ccccc3)cc2)c2c(N)ncnc2n1C[C@@H]1CCCN1C(=O)C(C#N)=CC1CC1]

Step 1

To a solution of 4-chloro-7H-pyrrolo[2,3-d]pyrimidine (10 g, 65.12 mmol, 1.0 eq) in THF (300 mL), NaH (5.30 g, 130.24 mmol, 2 eq) was added at 0° C. After 3 h, benzenesulfonyl chloride (22.53 g, 130.24 mmol, 2 eq) was added. The temperature was warmed to RT and continued for 1 h. The reaction mixture was poured into sat. NH4Cl and extracted with EtOAc. The organic layers were dried, concentrated and purified by column chromatography (eluting with 10% EtOAc in PE) to afford 4-chloro-7-(phenylsulfonyl)-7H-pyrrolo[2,3-d]pyrimidine as brown solid (4.5 g, 24% in yield)

Step 2

To the solution of 4-chloro-7-(phenylsulfonyl)-7H-pyrrolo[2,3-d]pyrimidine (3 g, 12.6 mmol, 1.0 eq) and TMEDA (3.0 mL, 18.9 mmol, 1.5 eq) in THF (120 mL), n-BuLi (7.5 mL, 18.9 mmol, 1.5 eq) was added at −78° C. After 3 min, CH3I (3.7 mL, 59.2 mmol, 4.7 eq) was added. After 3 h, the reaction mixture was warmed to RT over 1 h. The reaction was quenched by addition of sat NH4Cl (10 mL) at −78° C. EtOAc (200 mL) and water (100 mL) was added. The organic layer was separated, dried and concentrated to afford 4-chloro-6-methyl-7-(phenylsulfonyl)-7H-pyrrolo[2,3-d]pyrimidine as a brown solid (6.7 g, 90% in yield).

Step 3

To the solution of 4-chloro-6-methyl-7-(phenylsulfonyl)-7H-pyrrolo[2,3-d]pyrimidine (10 g, 32.5. mmol, 1.0 eq) in THF (400 mL), t-BuOK (18.23 g, 163.0 mmol, 5 eq) was added and stirred at RT for 12 h. Sat. NaHCO3 (50 mL) was added and extracted with EtOAc. The organic layers were separated, dried and concentrated to afford 4-chloro-6-methyl-7H-pyrrolo[2,3-d]pyrimidine as a brown solid (2.7 g, 50% in yield).

Step 4

To the solution of 4-chloro-6-methyl-7H-pyrrolo[2,3-d]pyrimidine (1.0 g, 5.97 mmol, 1.0 eq) and (S)-tert-butyl 2-(hydroxymethyl)pyrrolidine-1-carboxylate (1.32 g, 6.57 mmol, 1.1 eq) and PPh3 (3.03 g, 11.94 mmol, 2.0 eq) in THF (50 mL), DIEA (2.08 g, 11.94 mmol, 2.0 eq) was added at 0° C. The resulted mixture was stirred and warmed to RT for 12 h. Solvent was removed and purified by column chromatography (eluting with 10% EtOAc in PE) to afford (S)-tert-butyl 2-((4-chloro-6-methyl-7H-pyrrolo[2,3-d]pyrimidin-7-yl)methyl) pyrrolidine-1-carboxylate as a white solid (2.08 g, 100% in yield).

Step 5

To the solution of (S)-tert-butyl 2-((4-chloro-6-methyl-7H-pyrrolo[2,3-d]pyrimidin-7-yl)methyl)pyrrolidine-1-carboxylate (1.0 g, 2.86 mmol, 1.0 eq) in DMF (20 mL), NIS (0.675 g, 3.00 mmol, 1.05 eq) was added at 0° C. The resulted mixture was stirred and warmed to RT for 12 h. Solvent was removed and purified by column chromatography to afford (S)-tert-butyl 2-((4-chloro-5-iodo-6-methyl-7H-pyrrolo[2,3-d]pyrimidin-7-yl)methyl)pyrrolidine-1-carboxylate as white solid (1.0 g, 77% in yield) which was converted to the title compound as described in Example 30 above. LCMS m/z 519.1 (M+H)+.

Proceeding as described above but substituting 4-phenoxyphenylboronic acid with 2-(4-(3,5-difluorophenoxy)phenyl)-4,4,5,5-tetramethyl-1,3,2-dioxaborolane and 2-(2-fluoro-4-phenoxyphenyl)-4,4,5,5-tetramethyl-1,3,2-dioxaborolane, (S)-2-(2-((4-amino-5-(4-(3,5-difluorophenoxy)phenyl)-6-methyl-7H-pyrrolo[2,3-d]pyrimidin-7-yl)methyl)pyrrolidine-1-carbonyl)-3-cyclopropylacrylonitrile LCMS m/z m/z 555.2 (M+H)+ and (S)-2-((4-amino-5-(2-fluoro-4-phenoxyphenyl)-6-methyl-7H-pyrrolo[2,3-c]pyrimidin-7-yl)methyl)pyrrolidine-1-carbonyl)-3-cyclopropylacrylonitrile LCMS m/z 536.6 (M+H)+ were prepared respectively.

Example 30

Synthesis of (S)-2-(2-((4-amino-6-methyl-5-(4-phenoxyphenyl)-7H-pyrrolo[2,3-c]pyrimidin-7-yl)methyl)pyrrolidine-1-carbonyl)-4-(dimethylamino)-4-methylpent-2-enenitrile

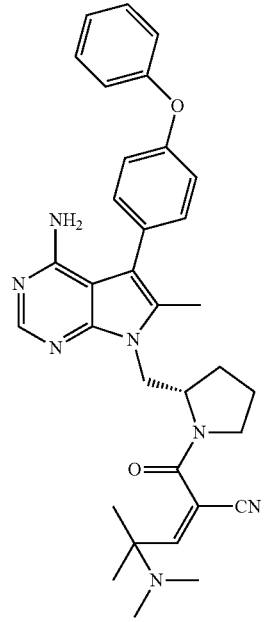 [SMILES: Cc1c(-c2ccc(Oc3ccccc3)cc2)c2c(N)ncnc2n1C[C@@H]1CCCN1C(=O)/C(C#N)=C\C(C)(C)N(C)C]

To a solution of (S)-3-(2-((4-amino-6-methyl-5-(4-phenoxyphenyl)-7H-pyrrolo[2,3-d]pyrimidin-7-yl)methyl)pyrrolidin-1-yl)-3-oxopropanenitrile (0.1 g, 0.21 mmol, 1.0 eq) in EtOH (2 mL) was added 2-(dimethylamino)-2-methylpropanal (0.06 g, 0.53 mmol, 2.5 eq) and piperidine acetate (5 mg). The resulted solution was stirred at 70° C. for 12 h, concentrated and purified by pre-HPLC to afford the title compound as a white solid (5 mg, 4% in yield). LCMS m/z 564.1 (M+H)⁺.

Example 31

Synthesis of (R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile tris(2,2,2-trifluoroacetate) salt

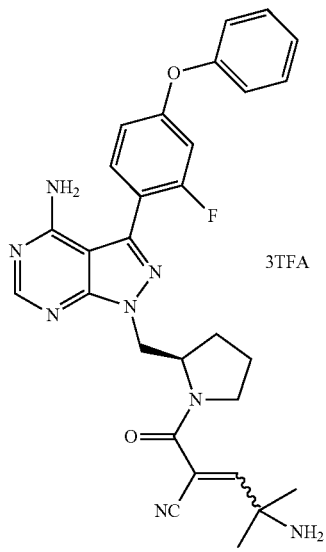 [SMILES: CC(C)(N)C=C(C#N)C(=O)N1CCC[C@@H]1Cn1nc(-c2ccc(Oc3ccccc3)cc2F)c2c(N)ncnc21]

Step 1
A solution of 3-((R)-2-((4-amino-3-(2-fluoro-4-phenoxyphenyl)-1H-pyrazolo[3,4-d]pyrimidin-1-yl)methyl)pyrrolidin-1-yl)-3-oxopropanenitrile (141 mg, 0.30 mmol, 1.0 equiv), tert-butyl 2-methyl-1-oxopropan-2-ylcarbamate (1.12 g, 6.00 mmol, 20.0 equiv), piperidine (255 mg, 3.0 mmol, 10.0 equiv) in 1,4-dioxane (15 mL) was refluxed for 2 h. The resulting mixture was concentrated under vacuum. The residue was submitted to flash chromatography eluting with ethyl acetate to give (R)-tert-butyl (5-(2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl)carbamate 90 mg as a pale yellow solid.

Step 2
To a solution of (R,E)-tert-butyl (5-(2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl)carbamate (90 mg, 0.14 mmol, 1 equiv) in 16 mL DCM was added 4 mL trifluoroacetic acid dropwise. The resulting solution was stirred for 3 h at room temperature. The solution was concentrated under reduced pressure. The residue was purified on Prep-HPLC. Conditions: (1#-Pre-HPLC-001(SHIMADZU)): Column, SunFire Prep C18, 19*150 mm 5 um; mobile phase, water with 0.05% TFA and CH3CN (40% CH₃CN up to 100% in 20 min); Detector, 254 nm to give the title compound as a pale light yellow solid.
MS (ESI, pos. ion) m/z: 541 (M+1).

Example 32

Synthesis of (R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile

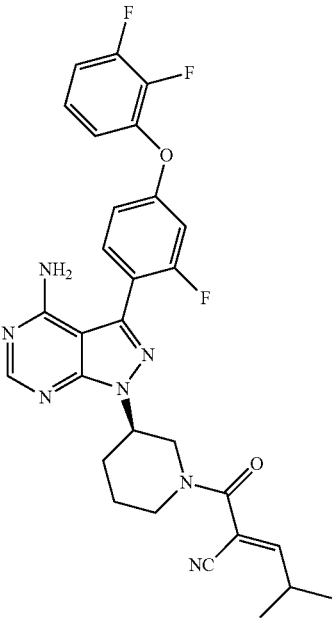 [SMILES: CC(C)/C=C(\C#N)C(=O)N1CCC[C@@H](n2nc(-c3ccc(Oc4cccc(F)c4F)cc3F)c3c(N)ncnc32)C1]

Step 1
To a solution of 1H-pyrazolo[3,4-d]pyrimidin-4-ylamine (3.0 g, 22.20 mmol, 1.0 eq) in DMF (30 mL), NIS (6.7 g, 24.42 mmol, 1.1 eq) was added at room temperature. The reaction mixture was stirred overnight at 60° C. The reaction mixture was cooled to room temperature and 10% aq. NaHCO₃ (150 mL) was added to the reaction mixture. The solid was filtered and re-crystallization from DMF solvent to give 3-iodo-1H-pyrazolo[3,4-d]pyrimidin-4-amine (4.0 g, 69% in yield).

Step 2
To a solution of 3-iodo-1H-pyrazolo[3,4-d]pyrimidin-4-ylamine (4.0 g, 15.32 mmol, 1.0 eq), (S)-3-hydroxypiperidine-1-carboxylic acid tert-butyl ester (4.313 g, 21.44 mmol, 1.4 eq), and PPh₃ (8.031 g, 30.64 mmol, 2.0 eq) in dry THF (200 mL), DIAD (4.658 g, 22.98 mmol, 1.5 eq) was added at room temperature. The reaction mixture was stirred at 70° C. for 72 h. The reaction mixture was concentrated and purified by silica gel chromatography (eluted with PE: EtOAc=1:1) to afford (R)-tert-butyl 3-(4-amino-3-iodo-1H-pyrazolo[3,4-d]pyrimidin-1-yl)piperidine-1-carboxylate (2.8 g, 41.2% in yield).

Step 3
A solution of (R)-tert-butyl 3-(4-amino-3-iodo-1H-pyrazolo[3,4-d]pyrimidin-1-yl)piperidine-1-carboxylate (2.8 g, 6.16 mmol, 1.0 eq), 2-(4-(2,3-difluorophenoxy)-2-fluorophenyl)-4,4,5,5-tetramethyl-1,3,2-dioxaborolane (1.7 g, 6.16 mmol, 1.0 eq), Pd(PPh₃)₄ (0.28 g, 0.08 mmol, 0.07 eq) and Na₂CO₃ (1.7 g, 15.4 mmol, 2.5 eq) in dioxane/H₂O (40/10 mL) was stirred at 90° C. overnight. The reaction mixture was concentrated and purified by Pre-TLC to afford (R)-tert-butyl 3-(4-amino-3-(4-(2,3-difluorophenoxy)-2-fluorophenyl)-1H-pyrazolo[3,4-d]pyrimidin-1-yl)piperidine-1-carboxylate (1.7 g, 51.1% yield).

Step 4

To a solution of (R)-tert-butyl 3-(4-amino-3-(4-(2,3-difluorophenoxy)-2-fluorophenyl)-1H-pyrazolo[3,4-d]pyrimidin-1-yl)piperidine-1-carboxylate (1.7 g, 3.15 mmol) in 20 ml of DCM, TFA (20 ml) was added. The reaction mixture was stirred at RT for 4 h. The mixture was washed with sat. NaHCO$_3$ (10 mL) and concentrated to give (R)-3-(4-(2,3-difluorophenoxy)-2-fluorophenyl)-1-(piperidin-3-yl)-1H-pyrazolo[3,4-d]pyrimidin-4-amine (1.1 g, 80% yield).

Step 5

To a mixture of (R)-3-(4-(2,3-difluorophenoxy)-2-fluorophenyl)-1-(piperidin-3-yl)-1H-pyrazolo[3,4-d]pyrimidin-4-amine (100 mg, 0.23 mmol, 1.0 eq), 2-cyano-4-methyl-pent-2-enoic acid (38 mg, 0.27 mmol, 1.2 eq) and DIEA (88 mg, 0.68 mmol, 3.0 eq) in 10 ml DCM was added HATU (130 mg, 0.34 mmol, 1.5 eq). The reaction mixture was stirred for 4 h at RT under N$_2$. The mixture was purified by Pre-HPLC to give the title compound (25 mg40% yield). LCMS: m/z$^+$ (562.2) (M+H)+.

Example 33

Synthesis of 2-((R)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-ethoxy-4-methylpent-2-enenitrile 2,2,2-trifluoroacetate

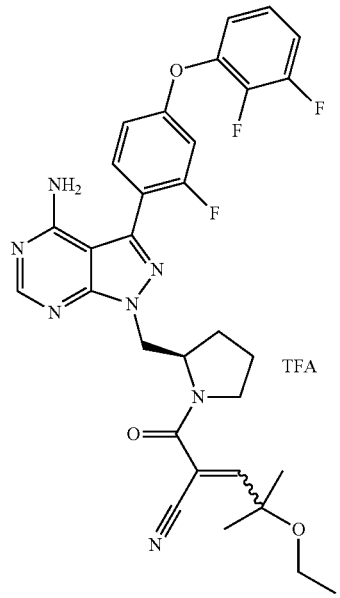 [SMILES: CCOC(C)(C)C=C(C#N)C(=O)N1CCC[C@@H]1Cn1nc(-c2ccc(Oc3cccc(F)c3F)cc2F)c2c(N)ncnc21]

A solution of 3-((R)-2-((4-amino-3-(4-(2,3-difluorophenoxy)-2-fluorophenyl)-1H-pyrazolo[3,4-d]pyrimidin-1-yl)methyl) pyrrolidin-1-yl)-3-oxopropanenitrile (202.8 mg, 0.40 mmol, 1.0 equiv), 2-ethoxy-2-methylpropanal (232 mg, 2.00 mmol, 5.0 equiv), piperidine (68 mg, 0.80 mmol, 2.0 equiv) in EtOH (20 mL) was stirred at room temperature overnight. The volatile phase was removed off under reduced pressure. The residue was purified on Prep-HPLC. Conditions: (1#-Pre-HPLC-001(SHIMADZU)): Column, SunFire Prep C18, 19*150 mm 5 um; mobile phase, water in 0.05% TFA and CH$_3$CN (40% CH$_3$CN up to 100% in 20 min); Detector, 254 nm. This resulted in 30 mg (10.43%) of the title compound as a white solid. MS (ESI, pos. ion) m/z: 606 (M-TFA+1)

Example 34

Synthesis of (S)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile

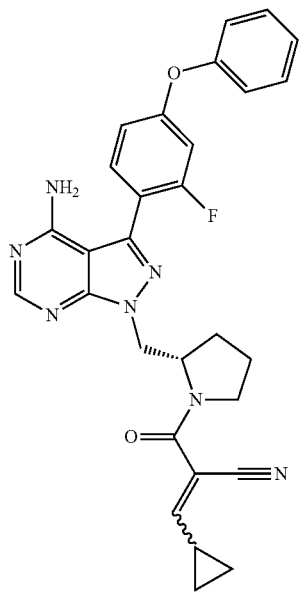 [SMILES: N#CC(=CC1CC1)C(=O)N1CCC[C@H]1Cn1nc(-c2ccc(Oc3ccccc3)cc2F)c2c(N)ncnc21]

To a solution of 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (2173. mg, 4.61 mmol) in ethanol (36 mL) was added cyclopropanecarbaldehyde (0.53 mL, 6.91 mmol) and piperidine (0.23 mL, 2.3 mmol). The reaction was heated to 90° C. for 75 minutes, then cooled and concentrated. The residue was dissolved in ethyl acetate (200 mL) and washed with water and then brine. The organic layer was dried (MgSO4), filtered and concentrated. The residue was purified by Isolera (100 g column, 1%-7% MeOH/DCM) to provided 1.32 g (55% yield) of the title compound. LCMS m/z 524 (M+H)$^+$.

Example 35

Synthesis of N-(2-(4-amino-3-(4-phenoxyphenyl)-1H-pyrazolo[3,4-d]pyrimidin-1-yl)ethyl)-2-cyano-3-cyclopropylacrylamide

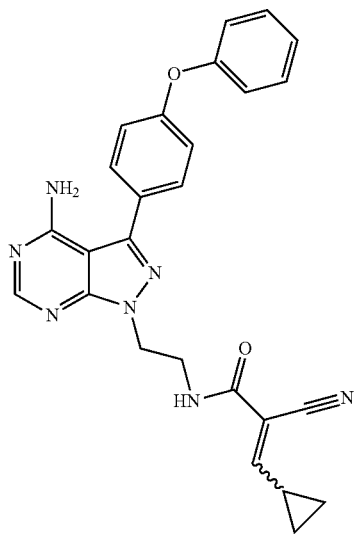 [SMILES: N#CC(=CC1CC1)C(=O)NCCn1nc(-c2ccc(Oc3ccccc3)cc2)c2c(N)ncnc21]

Step 1

To a solution of 3-(4-phenoxyphenyl)-1H-pyrazolo[3,4-d]pyrimidin-4-amine (300 mg, 1.0 mmole), triphenylphosphine (1.04 g, 3.96 mmole) and tert-butyl(2-hydroxyethyl)carbamate (238 mg, 1.5 mmoles) in THF (25 mL) was added DIAD (0.4 mL, 2 mmoles). The reaction was stirred for 5 hrs at room temperature and then water (30 mL) was added and extracted with ethyl acetate. The organic layers were combined, washed with aq. NaHCO$_3$ and brine, then dried (Na$_2$SO$_4$), filtered and concentrated. The resulting tert-butyl (2-(4-amino-3-(4-phenoxyphenyl)-1H-pyrazolo[3,4-d]pyrimidin-1-yl)ethyl)carbamate was used without further purification.

Step 2

The tert-butyl (2-(4-amino-3-(4-phenoxyphenyl)-1H-pyrazolo[3,4-d]pyrimidin-1-yl)ethyl)carbamate was dissolved in TFA (5 mL). After 30 minutes of stirring at room temperature, the reaction was diluted with water and washed with ethyl acetate. The aqueous layer was basified to pH=11-12 with NaOH and then washed with ethyl acetate. The organic layer was dried (Na$_2$SO$_4$), filtered and concentrated to collect 320 mg of 1-(2-aminoethyl)-3-(4-phenoxyphenyl)-1H-pyrazolo[3,4-d]pyrimidin-4-amine.

Step 3

To a solution of 1-(2-aminoethyl)-3-(4-phenoxyphenyl)-1H-pyrazolo[3,4-d]pyrimidin-4-amine (287 mg, 0.829 mmole), 2-cyanoacetic acid (85 mg, 1.0 mmole) and TEA (0.14 ml, 1.0 mmole) in DMF (10 mL) was added HATU (347 mg, 0.912 mmole). After stirring 3 hr at room temperature, water was added and extracted with ethyl acetate. The organic layer was washed with aq. NaHCO$_3$ and brine, then dried (Na$_2$SO$_4$), filtered and concentrated. The resulting residue was subjected to column chromatography (3% MeOH/DCM) to provide 90 mg (22% yield from step 1) of N-(2-(4-amino-3-(4-phenoxyphenyl)-1H-pyrazolo[3,4-d]pyrimidin-1-yl)ethyl)-2-cyanoacetamide.

Step 4

A solution of N-(2-(4-amino-3-(4-phenoxyphenyl)-1H-pyrazolo[3,4-d]pyrimidin-1-yl)ethyl)-2-cyanoacetamide (90 mg, 0.22 mole), cyclopropylcarboxaldehyde (18 mg, 0.26 mmole) and piperidine (22 mg, 0.26 mmole) in MeOH (5 mL) was stirred for 3 hr at room temperature. Then water was added and extracted with ethyl acetate. The organic layers were combined and washed with aq. NaHCO$_3$ and brine, then dried (Na$_2$SO$_4$), filtered and concentrated. The residue was purified by column chromatography (3% MeOH/DCM) to provide 39 mg (38% yield) of the title compound as a white solid. LCMS m/z 466 (M+H)$^+$.

Example 36

Synthesis of N-(2-(4-amino-3-(4-phenoxyphenyl)-1H-pyrazolo[3,4-d]pyrimidin-1-yl)ethyl)-2-cyano-3-cyclopropyl-N-methylacrylamide

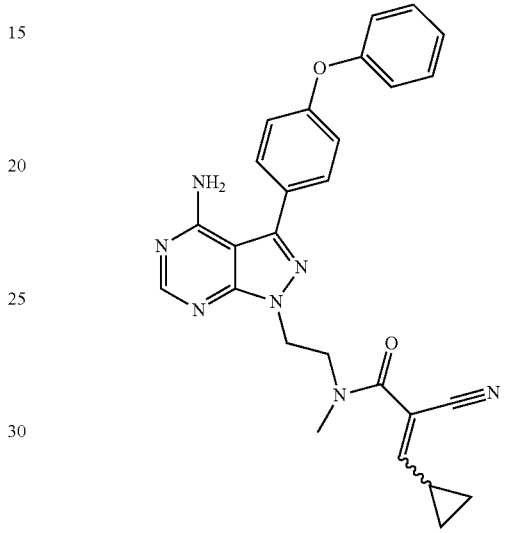

The title compound was prepared as described in Example 35 except tert-butyl(2-hydroxyethyl)(methyl)carbamate was used in step 1. LCMS m/z 480 (M+H)$^+$.

Example 37

Synthesis of (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-cyclopropylacrylonitrile

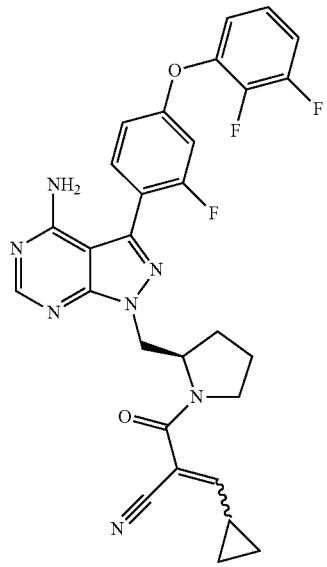 [SMILES: N#CC(=CC1CC1)C(=O)N1CCC[C@@H]1Cn1nc(-c2ccc(Oc3cccc(F)c3F)cc2F)c2c(N)ncnc21]

Step 1

A solution of 3-(4-(2,3-difluorophenoxy)-2-fluorophenyl)-1-((R)-pyrrolidin-2-ylmethyl)-1H-pyrazolo[3,4-d]pyrimidin-4-amine (50 mg, 0.12 mmol, 1.00 equiv), 2-cyanoacetic acid (14 mg, 0.18 mmol, 1.50 equiv), HATU (52 mg, 0.18 mmol, 1.5 equiv) and TEA (42 mg, 0.40 mmol, 5.00 equiv) in N,N-dimethylformamide (10 mL) was stirred overnight at 25° C. It was quenched with water (50 mL), which was extracted with EA. The organic layers were combined, washed with brine, dried over sodium sulfate, filtrated and concentrated. The residue was submitted to flash chromatography (SiO$_2$, PE: EtOAc=2:1 to 1:1) to give 48 mg (83%) of 3-((R)-2-((4-amino-3-(4-(2,3-difluorophenoxy)-2-fluorophenyl)-1H-pyrazolo[3,4-d]pyrimidin-1-yl)methyl)pyrrolidin-1-yl)-3-oxopropanenitrile as a yellow solid.

Step 2

A solution of 3-((R)-2-((4-amino-3-(4-(2,3-difluorophenoxy)-2-fluorophenyl)-1H-pyrazolo[3,4-d]pyrimidin-1-yl)methyl)pyrrolidin-1-yl)-3-oxopropanenitrile (240 mg, 0.47 mmol, 1.00 equiv), cyclopropanecarbaldehyde (98.7 mg, 1.41 mmol, 3.00 equiv) and piperidine (42 mg, 0.47 mmol, 1.00 equiv) in ethanol (15 mL) was stirred for 3 h at 65° C. The resulting mixture was concentrated under vacuum. The residue was purified on Prep-HPLC. Conditions: (1#-Pre-HPLC-001(SHIMADZU)): Column, SunFire Prep C18, 19*150 mm 5 um; mobile phase, water with 0.05% TFA and CH$_3$CN (40% CH$_3$CN up to 100% in 20 min); Detector, 254 nm. This resulted in 100 mg (36%) of the title compound as a white solid. MS (ESI, pos. ion) m/z: 560 (M+1).

Proceeding as described above, but substituting 3-((R)-2-((4-amino-3-(4-(2,3-difluorophenoxy)-2-fluorophenyl)-1H-pyrazolo[3,4-d]pyrimidin-1-yl)methyl)pyrrolidin-1-yl)-3-oxopropanenitrile with (R)-3-(3-(4-amino-3-(2,3-difluoro-4-phenoxyphenyl)-1H-pyrazolo[3,4-d]pyrimidin-1-yl)piperidin-1-yl)-3-oxopropanenitrile and cyclopropanecarbaldehyde with 2-methyl-2-morpholinopropanal, (R)-2-(3-(4-amino-3-(2,3-difluoro-4-phenoxyphenyl)-1H-pyrazolo[3,4-d]pyrimidin-1-yl)piperidine-1-carbonyl)-4-methyl-4-morpholinopent-2-enenitrile was prepared.

Example 38

Synthesis of (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-cyclopropylacrylonitrile

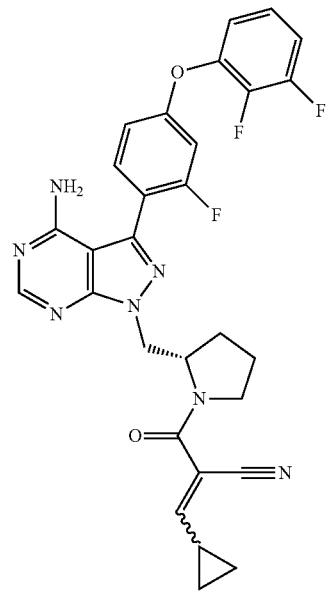 [SMILES: N#CC(=CC1CC1)C(=O)N1CCC[C@H]1Cn1nc(-c2ccc(Oc3cccc(F)c3F)cc2F)c2c(N)ncnc21]

Step 1

To a suspension of (S)-tert-butyl 2-((4-amino-3-iodo-1H-pyrazolo[3,4-d]pyrimidin-1-yl)methyl) pyrrolidine-1-carboxylate (2.7 g, 6.00 mmol, 1.00 equiv), 4-(2,3-difluorophenoxy)-2-fluorophenylboronic acid (1.6 g, 6.00 mmol, 1.00 equiv), potassium carbonate (3.3 g, 24.00 mmol, 4.00 equiv) in 1,4-dioxane (40 mL) and water (10 mL) was added Pd(PPh$_3$)$_4$ (488 mg, 0.60 mmol, 0.10 equiv) under nitrogen atmosphere. The resulting solution was stirred overnight at 90° C. The resulting mixture was concentrated under vacuum. The residue was applied onto a silica gel column with ethyl acetate/petroleum ether (1:5 to 2:1). This resulted in 1.97 g (61%) of (2S)-tert-butyl 2-((4-amino-3-(4-(2,3-difluorophenoxy)-2-fluorophenyl)-1H-pyrazolo[3,4-d]pyrimidin-1-yl)methyl) pyrrolidine-1-carboxylate as a reddish solid. MS (ESI, pos. ion) m/z: 541 (M+1)

Step 2

To a solution of (2S)-tert-butyl 2-((4-amino-3-(4-(2,3-difluorophenoxy)-2-fluorophenyl)-1H-pyrazolo[3,4-d]pyrimidin-1-yl)methyl) pyrrolidine-1-carboxylate (1.97 g, 3.65 mmol, 1.00 equiv) in DCM (30 mL) was added trifluoroacetic acid (7.5 mL). The resulting solution was stirred for 4 h at room temperature. This solution was concentrated under reduced pressure. This resulted in 2.4 g (Crude) of 3-(4-(2,3-difluorophenoxy)-2-fluorophenyl)-1((S)-pyrrolidin-2-ylmethyl)-1H-pyrazolo[3,4-d]pyrimidin-4-amine trifluoroacetic acid salt as a reddish oil. MS (ESI, pos. ion) m/z: 441 (M+1)

Step 3

A solution of 3-(4-(2,3-difluorophenoxy)-2-fluorophenyl)-1-((S)-pyrrolidin-2-ylmethyl)-1H-pyrazolo[3,4-d]pyrimidin-4-amine (2.4 g Crude, 3.65 mmol, 1.00 equiv), 2-cyanoacetic acid (0.47 g, 5.48 mmol, 1.50 equiv), HATU (2.08 g, 5.48 mmol, 1.50 equiv), TEA (2.54 ml, 18.25 mmol, 5.00 equiv) in DCM (40 mL) was stirred overnight at room temperature. The resulting mixture was diluted with water, and extracted with DCM. The DCM layers were combined and washed with brine, dried over Na$_2$SO$_4$ and concentrated. The residue was submitted to flash chromatography (SiO$_2$, PE: EtOAc=2:1 to 1:1) to give 1.28 g (69%) of 3-((S)-2-((4-amino-3-(4-(2,3-difluorophenoxy)-2-fluorophenyl)-1H-pyrazolo[3,4-d]pyrimidin-1-yl)methyl) pyrrolidin-1-yl)-3-oxopropanenitrile as a yellow solid.

Step 4

A solution of 3-((S)-2-((4-amino-3-(4-(2,3-difluorophenoxy)-2-fluorophenyl)-1H-pyrazolo[3,4-d]pyrimidin-1-yl)methyl) pyrrolidin-1-yl)-3-oxopropanenitrile (304.2 mg, 0.60 mmol, 1.00 equiv), cyclopropanecarbaldehyde (210 mg, 3 mmol, 5 equiv), piperidine (102 mg, 1.20 mmol, 2 equiv) in EtOH (20 mL) was stirred at rt. The resulting mixture was concentrated under vacuum. Then concentrated and purified on Prep-HPLC. Conditions: (1#-Pre-HPLC-001(SHIMADZU)): Column, SunFire Prep C18, 19*150 mm 5 um; mobile phase, water with 0.05% TFA and CH3CN (40% CH$_3$CN up to 100% in 20 min); Detector, 254 nm. This resulted in 90 mg (22.3%) of the title compound as a white solid.MS (ESI, pos. ion) m/z: 560 (M-TFA+1).

Example 39

Synthesis of N-(3-(4-amino-3-(4-phenoxyphenyl)-1H-pyrazolo[3,4-d]pyrimidin-1-yl)-2,2-dimethylpropyl)-2-cyano-3-cyclopropylacrylamide

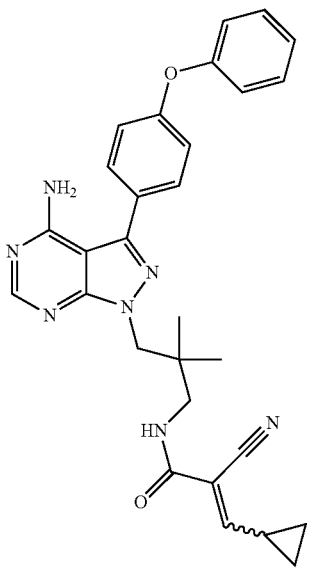 [SMILES: CC(C)(CNC(=O)C(C#N)=CC1CC1)Cn1nc(-c2ccc(Oc3ccccc3)cc2)c2c(N)ncnc21]

Step 1

A solution of 2,2-dimethylpropane-1,3-diol (20.8 g, 199.72 mmol, 1.00 equiv) and HBr (1 mL) was stirred for 1 h at 110° C. in an oil bath, then a solution of HBr (17.82 g, 220 mmol, 1.10 equiv) in AcOH (100 mL) was loaded dropwise, the resulting mixture was stirred for another 11 hr at 110° C. The resulting mixture was concentrated under vacuum. To this residue were added ethylene glycol dimethyl ether (270 mL), water (90 mL) and LiOH (9.6 g, 2.00 equiv). The resulting solution was stirred for 3 h at 25° C., which was extracted with ether. The organic layers were combined, washed with hydrogen chloride (1 N), washed with brine, dried over anhydrous sodium sulfate and concentrated under vacuum to give 15 g (45%) of 3-bromo-2,2-dimethylpropan-1-ol as a colorless oil.

Step 2

To a solution of 2,3-dihydro-1H-isoindole-1,3-dione (3.1 g, 21.07 mmol, 1.00 equiv), 3-bromo-2,2-dimethylpropan-1-ol (3.4 g, 23.2 mmol, 1.10 equiv), triphenylphosphane (10.9 g, 41.56 mmol, 2.00 equiv) in THF (100 mL) was loaded diisopropyl azodicarboxylate (8.3 g, 41.09 mmol, 2.00 equiv) dropwise at 0° C. under nitrogen atmosphere. The resulting solution was stirred for 12 h at 25° C. The resulting mixture was concentrated under vacuum. The residue was applied onto a silica gel column eluting with ethyl acetate/petroleum ether (1/50). This resulted in 3.2 g (51%) of 2-(3-bromo-2,2-dimethylpropyl)-2,3-dihydro-1H-isoindole-1,3-dione as a colorless oil.

Step 3

A suspension of 3-(4-phenoxyphenyl)-1H-pyrazolo[3,4-d]pyrimidin-4-amine (400 mg, 1.3 mmol, 1.00 equiv), 2-(3-bromo-2,2-dimethylpropyl)-2,3-dihydro-1H-isoindole-1,3-dione (570 mg, 1.95 mmol, 1.50 equiv) and cesium carbonate (847 mg, 2.60 mmol, 2.00 equiv) in NMP (50 mL) was stirred at 100° C. for 12 h under nitrogen atmosphere. It was quenched with water (150 mL). The resulting solution was extracted with ethyl acetate (5×30 mL). The organic layers were combined, dried over sodium sulfate and concentrated under vacuum. The residue was applied onto a silica gel column eluting with dichloromethane/methanol (10/1). This resulted in 280 mg (41%) of 2-(2-[[4-amino-3-(4-phenoxyphenyl)-1H-pyrazolo[3,4-d]pyrimidin-1-yl]methyl]-2-methylpropyl)-2,3-dihydro-1H-isoindole-1,3-dione as a yellow oil.

Step 4

A solution of 2-[3-[4-amino-3-(4-phenoxyphenyl)-1H-pyrazolo[3,4-d]pyrimidin-1-yl]-2,2-dimethylpropyl]-2,3-dihydro-1H-isoindole-1,3-dione (200 mg, 0.39 mmol, 1.00 equiv) and hydrazine (130 mg, 3.25 mmol, 8.00 equiv) in ethanol (30 mL) was stirred for 3 h at 70° C. in an oil bath. The resulting mixture was concentrated under vacuum. Water (50 mL) was added to the residue. The resulting solution was extracted with dichloromethane (3×50 mL). The organic layers were combined, dried over sodium sulfate and concentrated under vacuum. The residue was applied onto a silica gel column with dichloromethane/methanol (30/1). This resulted in 0.06 g (40%) of 1-(3-amino-2,2-dimethylpropyl)-3-(4-phenoxyphenyl)-1H-pyrazolo[3,4-d]pyrimidin-4-amine as a yellow oil.

Step 5

A solution of 1-(3-amino-2,2-dimethylpropyl)-3-(4-phenoxyphenyl)-1H-pyrazolo[3,4-d]pyrimidin-4-amine (110 mg, 0.28 mmol, 1.00 equiv), 2-cyanoacetic acid (36 mg, 0.42 mmol, 1.50 equiv), HATU (0.108 g, 1.00 equiv) and triethylamine (57 mg, 0.56 mmol, 2.00 equiv) in N,N-dimethylformamide (10 mL) was stirred for 5 h at 25° C. It was quenched with water (100 mL). The resulting solution was extracted with ethyl acetate (3×50 mL). The organic layers were combined, washed with brine. dried and concentrated under vacuum. The residue was applied onto a silica gel column eluting with dichloromethane/methanol (50/1). This resulted in 100 mg (78%) of N-[3-[4-amino-3-(4-phenoxyphenyl)-1H-pyrazolo[3,4-d]pyrimidin-1-yl]-2,2-dimethylpropyl]-2-cyanoacetamide as a yellow oil.

Step 6

A solution of N-(3-(4-amino-3-(4-phenoxyphenyl)-1H-pyrazolo[3,4-d]pyrimidin-1-yl)-2,2-dimethylpropyl)-2-cyanoacetamide (0.12 g, 0.26 mmol, 1.0 eq.), cyclopropanecarbaldehyde (56 mg, 0.78 mmol, 3.0 eq.) and a drop of piperidine in ethanol (15 mL) was refluxed overnight. The volatile phase was removed under reduced pressure. The residue was applied on silica gel eluting with petroleum: ethyl acetate (1:1). This provided 50 mg (38%) of the title compound as a white solid. MS (ESI, pos. ion) m/z: 508 (M+1).

Example 40

Synthesis of 2-((S)-2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile

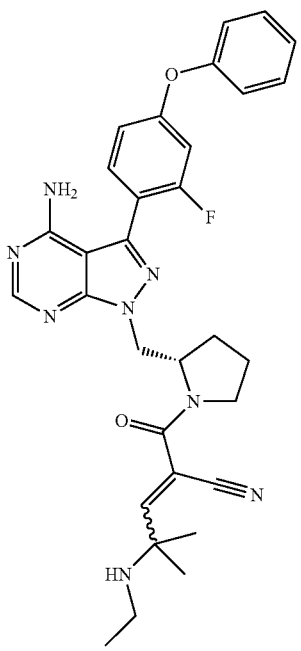 [SMILES: CCNC(C)(C)C=C(C#N)C(=O)N1CCC[C@H]1Cn1nc(-c2ccc(Oc3ccccc3)cc2F)c2c(N)ncnc21]

Step 1

To a solution of 2-amino-2-methylpropanoic acid (10.3 g, 0.1 mol, 1.0 equiv) in 1 N NaOH (100 mL) and THF (30 mL) was added (Boc)$_2$O (26 g, 0.12 mol, 1.2 equiv) portionwise at room temperature. This mixture was stirred overnight at room temperature. The mixture was concentrated and then extracted with ethyl acetate (100 mL×2). The aqueous phase was adjusted to PH=3~4, then extracted with ethyl acetate (200 mL×2). The organic phases were combined, washed with brine, dried over Na$_2$SO$_4$, concentrated to give 9 g (44%) of the desired product 2-(tert-butoxycarbonylamino)-2-methylpropanoic acid as a white solid.

Step 2

To a solution of 2-(tert-butoxycarbonylamino)-2-methylpropanoic acid (8.12 g, 0.04 mol, 1 equiv) in DMF (100 mL) was added NaH (4.8 g, 0.12 mol, 3.0 equiv) portionwise at 0° C. The mixture was stirred for 5 min at this temperature then ethyl iodide (18.7 g, 0.12 mol, 3.0 equiv) was added dropwise at 0° C. The resulting mixture was stirred at room temperature overnight then it was quenched with H$_2$O, extracted with ethyl acetate. The organic phases were combined, washed with brine, dried and concentrated. The residue was purified on silica gel column (PE/EA=5/1) to give 6 g (57%) of the desired product ethyl 2-(tert-butoxycarbonyl(ethyl)amino)-2-methylpropanoate as a colorless oil.

Step 3

To a suspension of LiAlH$_4$ (760 mg, 20 mmol, 1.0 equiv) in THF (50 mL) was added ethyl 2-(tert-butoxycarbonyl (ethyl)amino)-2-methylpropanoate (5.18 g, 20 mmol, 1 equiv) at 0° C. under N$_2$. The mixture was stirred for 4 h at 0° C. It was quenched with ice/water at 0° C., then extracted with ethyl acetate (50 mL×3). The organic layers were combined, washed with brine, dried over Na$_2$SO$_4$ and concentrated. The residue was purified by a silica gel column (pet. ether/ethyl acetate=4/1) to give 2 g (45%) of tert-butyl ethyl(1-hydroxy-2-methylpropan-2-yl)carbamate as a colorless oil.

Step 4

To a solution of tert-butyl ethyl(1-hydroxy-2-methylpropan-2-yl)carbamate (2.18 g, 10 mmol, 1.0 equiv) in DCM (150 mL) was added Dess-martin periodinane (4.24 g, 10 mmol, 1.0 equiv) portionwise at 0° C. The resulting mixture was stirred for 4 h at room temperature. Saturated solutions of aqueous sodium hydrogencarbonate and sodium thiosulfate were added. The resulting mixture was stirred for 0.5 h. The organic phase was separated, washed with saturated sodium hydrogencarbonate, brine, dried over sodium sulfate and concentrated to give 1.5 g (71%) of tert-butyl methyl (2-ethyl-1-oxopropan-2-yl)carbamate as a colorless oil.

Step 5

To a solution of 3-((S)-2-((4-amino-3-(2-fluoro-4-phenoxyphenyl)-1H-pyrazolo[3,4-d]pyrimidin-1-yl)methyl)pyrrolidin-1-yl)-3-oxopropanenitrile (236 mg, 0.5 mmol, 1 equiv) and tert-butyl ethyl(2-methyl-1-oxopropan-2-yl)carbamate (2.15 g, 10 mmol, 20 equiv) in dioxane (30 mL) was added 0.5 mL piperidine, 1 drop AcOH and 2 g of 4 A molecular sieves. The resulting mixture was stirred for 2 h at 110° C. The solids was filtered out, the filtrate was diluted with 200 mL of ethyl acetate, washed with brine, dried over Na$_2$SO$_4$, concentrated and purified by silica gel column (ethyl acetate/MeOH 10/1) to give 60 mg (19%) of tert-butyl 5-((S)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl(ethyl)carbamate as a white solid.

Step 6

To a solution of tert-butyl 5-((S)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl(ethyl)carbamate (60 mg, 0.089 mmol) in DCM (8 mL) was added 2 mL of CF$_3$COOH. The mixture was stirred for 2 h at room temperature, then concentrated and purified by Prep-HPLC. Conditions: (1#-Pre-HPLC-001(SHIMADZU)): Column, SunFire Prep C18, 19*150 mm 5 um; mobile phase, water with 0.05% TFA and CH$_3$CN (40% CH$_3$CN up to 100% in 20 min); Detector, 254 nm. This resulted in 12 mg (16%) of the title compound as a white solid and his TFA salt. LC-MS: m/z 569 (M+H$^+$).

Example 41

Synthesis of 2-((R)-2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile

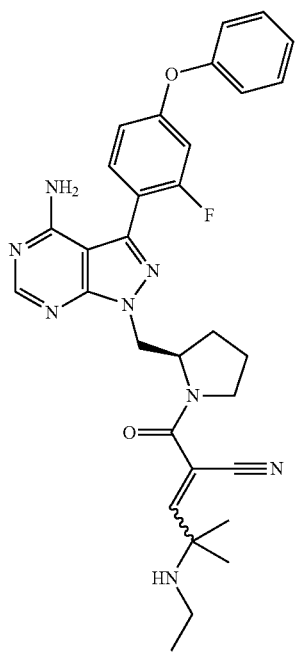 [SMILES: CCNC(C)(C)C=C(C#N)C(=O)N1CCC[C@@H]1Cn1nc(-c2ccc(Oc3ccccc3)cc2F)c2c(N)ncnc21]

Step 1

To a solution of 3-((R)-2-((4-amino-3-(2-fluoro-4-phenoxyphenyl)-1H-pyrazolo[3,4-d]pyrimidin-1-yl)methyl)pyrrolidin-1-yl)-3-oxopropanenitrile (236 mg, 0.5 mmol, 1 equiv) and tert-butyl ethyl(2-methyl-1-oxopropan-2-yl)carbamate (2.15 g, 10 mmol, 20 equiv) in dioxane (30 mL) was added 0.5 mL piperidine, 1 drop AcOH and 2 g of 4 A molecular sieves. The resulting mixture was stirred for 2 h at 110° C. The solids was filtered out, the filtrate was diluted with 200 mL of ethyl acetate, washed with brine, dried over Na$_2$SO$_4$, concentrated and purified on silica gel column (ethyl acetate/MeOH 10/1) to give 60 mg (19%) of tert-butyl 5-((R)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl)(ethyl)carbamate as a white solid.

Step 2

To a solution of tert-butyl 5-((R)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl)(ethyl)carbamate (60 mg, 0.089 mmol) in DCM (10 mL) was added 2.5 mL of CF$_3$COOH. The mixture was stirred for 2 h at room temperature. The volatile phase was removed under reduced pressure and the residue was purified on Prep-HPLC. Conditions: (1#-Pre-HPLC-001(SHIMADZU)): Column, SunFire Prep C18, 19*150 mm 5 um; mobile phase, water with 0.05% TFA and CH3CN (40% CH$_3$CN up to 100% in 20 min); Detector, 254 nm. This resulted 12 mg (16%) of the title compound as a white solid and his TFA salt. LC-MS: m/z 569 (M+H$^+$).

Example 42

Synthesis of 2-((S)-2-((4-amino-3-(2-fluoro-4-phenoxyphenyl)-1H-pyrazolo[3,4-d]pyrimidin-1-yl)methyl)pyrrolidine-1-carbonyl)-4-(cyclopropylamino)-4-methylpent-2-enenitrile

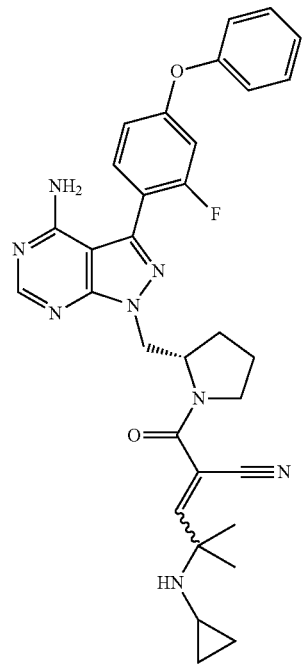 [SMILES: CC(C)(C=C(C#N)C(=O)N1CCC[C@H]1Cn1nc(-c2ccc(Oc3ccccc3)cc2F)c2c(N)ncnc21)NC1CC1]

Step 1

To a 250 mL of sealed tube was added ethyl 2-bromo-2-methylpropanoate (19.4 g, 0.1 mol, 1.0 equiv), cyclopropanamine (11.4 g, 0.2 mol, 2.0 equiv), K$_2$CO$_3$ (27.6 g, 0.2 mol, 2.0 equiv), KI (1.66 g, 0.01 mol, 0.1 equiv) and 200 mL of MeCN. The mixture was stirred at 100° C. for 12 h then cooled to room temperature and the solids were filtered. The filtrate was concentrated and purified on silica gel column eluting with pet. ether/ethyl acetate=4/1 to give 8.0 g (46%) of ethyl 2-(cyclopropylamino)-2-methylpropanoate.

Step 2

To a solution of LiAlH$_4$ (760 mg, 20 mmol, 1.0 equiv) in THF (50 mL) was added ethyl 2-(cyclopropylamino)-2-methylpropanoate (3.42 g, 20 mmol, 1.0 equiv) in THF (10 mL) at 0° C. under N$_2$. The resulting suspension was stirred at 0° C. for 2 h. The reaction was quenched with Na$_2$SO$_4$.10H$_2$O (3.0 g) at 0° C. The solid was filtered off and the filtrate was concentrated under reduced pressure. This resulted in 2-(cyclopropylamino)-2-methylpropan-1-ol 1.3 g (50%) as a white solid.

Step 3

To a solution of oxalyl chloride (11.43 g, 90 mmol, 1.5 equiv) in DCM (300 mL) was added DMSO (11.7 g, 150 mmol, 2.5 equiv) at −78° C. under N$_2$ atmosphere. The resulting mixture was stirred for 0.5 h then a solution of 2-(cyclopropylamino)-2-methylpropan-1-ol (7.74 g, 60 mmol, 1.0 equiv) in DCM (20 mL) was added dropwise at −78° C. and then stirred for another 1 h. Then TEA (36.4 g, 0.36 mol, 6.0 equiv) was added and stirring was continued for 20 min at room temperature. The reaction was then diluted with DCM (200 mL) and washed with aq. NaHCO$_3$ and brine, dried over Na₂SO₄, concentrated to give the crude product, which was purified with distillation under reduced pressure. This resulted in 1.0 g (13%) of 2-(cyclopropylamino)-2-methylpropanal was obtained as a colorless oil.

Step 4

A solution of 3-((S)-2-((4-amino-3-(2-fluoro-4-phenoxyphenyl)-1H-pyrazolo[3,4-d]pyrimidin-1-yl)methyl)pyrrolidin-1-yl)-3-oxopropanenitrile (118 mg, 0.25 mmol, 1.0 equiv), 2-(cyclopropylamino)-2-methylpropanal (0.16 g, 1.25 mmol, 5.0 equiv) and one drop of piperidine in MeCN (10 mL) was stirred overnight at 40° C. The solvent was removed and the residue was purified on Prep-HPLC. Conditions: (1#-Pre-HPLC-001(SHIMADZU)): Column, SunFire Prep C18, 19*150 mm 5 um; mobile phase, water with 0.05% TFA and CH₃CN (40% CH₃CN up to 100% in 20 min); Detector, 254 nm. This resulted in 40 mg (27%) of the title compound as a white solid and bis TFA salt. LC-MS: m/z 581 (M+H⁺).

Example 43

Synthesis of 2-((S)-2-((4-amino-3-(2-fluoro-4-phenoxyphenyl)-1H-pyrazolo[3,4-d]pyrimidin-1-yl)methyl)pyrrolidine-1-carbonyl)-4-(2-methoxyethylamino)-4-methylpent-2-enenitrile

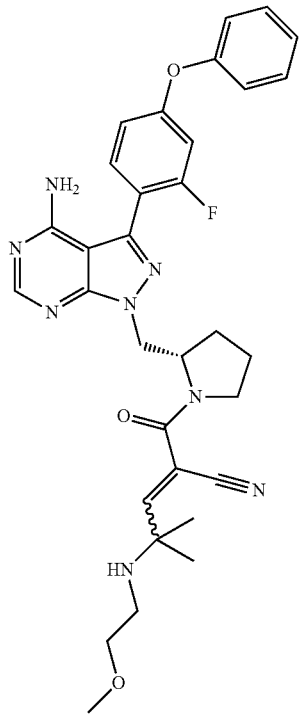 [SMILES: COCCNC(C)(C)C=C(C#N)C(=O)N1CCC[C@H]1Cn1nc(-c2ccc(Oc3ccccc3)cc2F)c2c(N)ncnc21]

To a suspension of 4-amino-2-((S)-2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile (210 mg, 0.39 mmol, 1.0 equiv), KI (130 mg, 0.78 mmol, 2.0 equiv) and potassium carbonate (166 mg, 1.17 mmol, 3.0 equiv) in CH₃CN (15 mL) was added 1-bromo-2-methoxyethane (160 mg, 1.17 mmol, 3.0 equiv). The resulting suspension was stirred at 50° C. overnight. The solvent was removed under reduced pressure and then water (20 mL) was added to the residue. The resulting mixture was extracted with ethyl acetate (30 mL*3). The organic layers were combined, washed with brine, dried over sodium sulfate and concentrated. The residue was purified on Prep-HPLC. Conditions: (1#-Pre-HPLC-001(SHIMADZU)): Column, SunFire Prep C18, 19*150 mm 5 um; mobile phase, WATER WITH 0.5% NH4OH and CH3CN (40% CH3CN up to 100% in 20 min); Detector, 254 nm. This resulted in 8.7 mg (3.7%) of the title compound as an off-white solid. MS (ESI, pos. ion) m/z: 599 (M+1).

Example 44

Synthesis of 2-{2-[4-amino-5-(2-fluoro-4-phenoxyphenyl)-pyrrolo[2,3-d]pyrimidin-7-ylmethyl]-pyrrolidine-1-carbonyl}-3-cyclopropyl-acrylonitrile

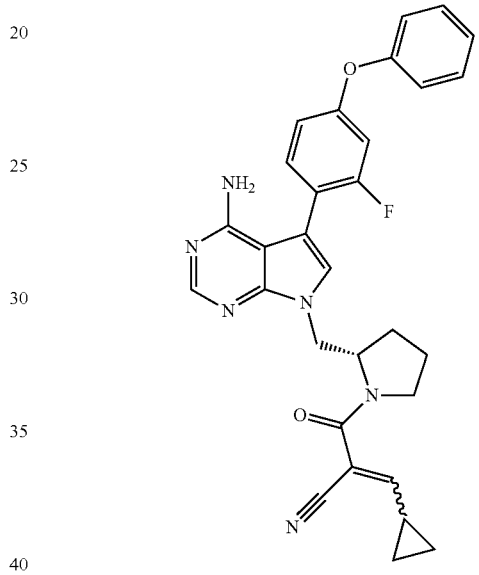

Step 1

The mixture of 2-(4-amino-5-iodo-pyrrolo[2,3-d]pyrimidin-7-ylmethyl)-pyrrolidine-1-carboxylic acid tert-butyl ester (500.00 mg, 1.13 mmol, 1.0 eq), 3-fluoro-4-phenoxy-phenyl-boronic acid (240.00 mg, 1.13 mmol, 1.0 eq), Pd(PPh₃)₄ (100.00 mg) and Na₂CO₃ (300.00 mg, 2.83 mmol, 2.5 eq) in dioxane/H₂O (40/10 ml) was stirred at 90° C. for 4 h. The reaction mixture was concentrated and purified by Pre-TLC to afford 400 mg (70%) of 2-[4-amino-5-(2-fluoro-4-phenoxy-phenyl)-pyrrolo[2,3-d]pyrimidin-7-ylmethyl]-pyrrolidine-1-carboxylic acid tert-butyl ester.

Step 2

To a solution of 2-[4-amino-5-(2-fluoro-4-phenoxy-phenyl)-pyrrolo[2,3-d]pyrimidin-7-ylmethyl]-pyrrolidine-1-carboxylic acid tert-butyl ester (400 mg, 0.79 mmol) in 10 ml of DCM, was added TFA (10 ml). The reaction mixture was stirred at RT for 2 h. The mixture was then concentrated to give 5-(2-fluoro-4-phenoxy-phenyl)-7-pyrrolidin-2-ylmethyl-7H-pyrrolo[2,3-d]pyrimidin-4-ylamine (320 mg), which was used in the next step without any further purification.

Step 3

To a mixture of 5-(2-fluoro-4-phenoxy-phenyl)-7-pyrrolidin-2-ylmethyl-7H-pyrrolo[2,3-d]pyrimidin-4-ylamine (100 mg, 0.25 mmol, 1.0 eq), 2-cyano-3-cyclopropyl-acrylic acid (42 mg, 0.3 mmol, 1.2 eq) and DIEA (97 mg, 0.75 mmol, 3.0 eq) in 10 ml of DCM was added HATU (145 mg, 0.38 mmol, 1.5 eq). The mixture was stirred for 4 h at RT under N$_2$. LCMS showed the reaction was completed. The reaction mixture was concentrated and purified by Pre-TLC to provide 71 mg (54%) of the title compound. LCMS: m/z 523.2 (M+H)$^+$.

Example 45

Synthesis of (R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-aminocyclopropyl)acrylonitrile

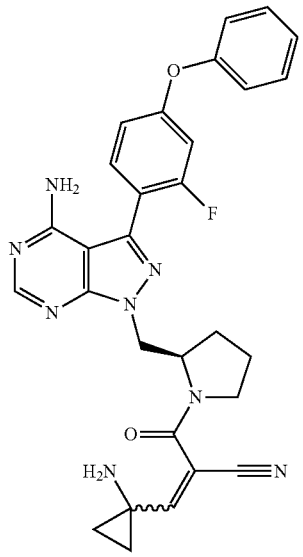 [SMILES: N#CC(=CC1(N)CC1)C(=O)N1CCC[C@@H]1Cn1nc(-c2ccc(Oc3ccccc3)cc2F)c2c(N)ncnc21]

Step 1

To a solution of tert-butyl (1-(hydroxymethyl)cyclopropyl)carbamate (Bioorg. Med. Chem. Lett., 2008, 18(6), 2188) (135 mg, 0.72 mmoles) in DCM (8 mL) was added Dess-Martin periodinane (277 mg, 0.65 mmole). After stirring 1 hr, the reaction was filtered through celite and concentrated to a yellow oil which was further purified by Isolera (7%-70% ethyl acetate/hexanes) to provide 84 mg (87%) of tert-butyl(1-formylcyclopropyl)-carbamate as a white solid.

Step 2

To a solution of 3-[(2R)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (100. mg, 0.2100 mmol) dissolved in methanol (4 mL) and DCM (4 mL) was added piperidine (0.1 mL, 0.8500 mmol) and tert-butyl N-(1-formylcyclopropyl)carbamate (58.9 mg, 0.3200 mmol). The reaction was heated to reflux for 6 hrs and then cooled and concentrated. The residue was and dissolved in ethyl acetate (50 mL) and washed with water (50 mL) and then brine. The organic layer was dried (MgSO$_4$), filtered and concentrated. The residue was purified by Isolera (1%-8% MeOH/DCM) to provide 39 mg (13% yield) of tert-butyl N-[1-[3-[(2R)-2-[[4-amino-3-(2-fluoro-4-phenoxy-phenyl)pyrazolo[3,4-d]pyrimidin-1-yl]methyl]pyrrolidin-1-yl]-2-cyano-3-oxo-prop-1-enyl]cyclopropyl]carbamate.

Step 3

To a solution of tert-butyl N-[1-[3-[(2R)-2-[[4-amino-3-(2-fluoro-4-phenoxy-phenyl)pyrazolo[3,4-d]pyrimidin-1-yl]methyl]pyrrolidin-1-yl]-2-cyano-3-oxo-prop-1-enyl]cyclopropyl]carbamate (27 mg, 0.04 mmol) in DCM (3 mL) was added TFA (1 mL). The solution was stirred for 5 hrs. and then concentrated. The residue was purified by prep-TLC (5% MeOH/DCM) to provide 2.68 mg (12%) of the title compound. MS (pos. ion) m/z: 539 (M+1).

Example 46

Synthesis of 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-morpholino-pent-2-enenitrile

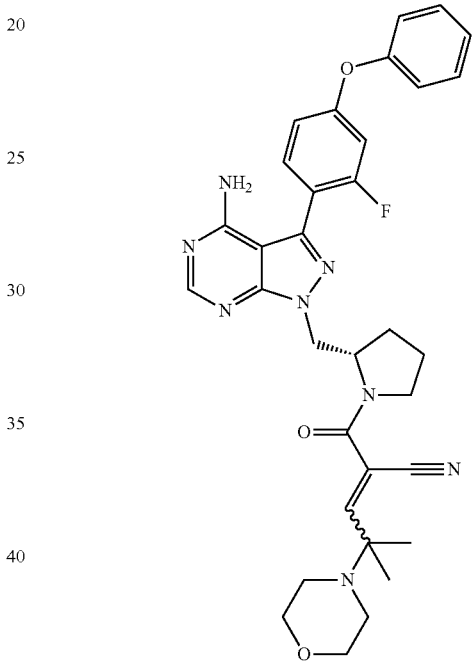

To a sealed tube was added 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (900 mg, 1.91 mmol), ethanol (12 mL), piperidine (0.23 mL, 2.29 mmol) and 2-methyl-2-morpholino-propanal (0.49 mL, 2.86 mmol). The tube was sealed and heated to 105° C. for 24 hrs. The mixture was then cooled, concentrated and then dissolved in ethyl acetate (100 mL) and washed with 5% citric acid (100 ml) and then brine. The organic layer was dried (MgSO$_4$), filtered and concentrated. The crude material was purified by Isolera (column size 100 g. Solvent system 4%-8% MeOH/EtOAc) to obtain 245 mg (21% yield) of the title compound. MS (pos. ion) m/z: 611 (M+1).

Proceeding as described above by substituting 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile with (R)-3-(3-(4-amino-3-(2-fluoro-4-phenoxyphenyl)-1H-pyrazolo[3,4-d]pyrimidin-1-yl)piperidin-1-yl)-3-oxopropanenitrile, (R)-2-(3-(4-amino-3-(2-fluoro-4-phenoxyphenyl)-1H-pyrazolo[3,4-d]pyrimidin-1-yl)piperidine-1-carbonyl)-4-methyl-4-morpholinopent-2-enenitrile was prepared.

Example 47

Synthesis of 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-morpholino-pent-2-enenitrile

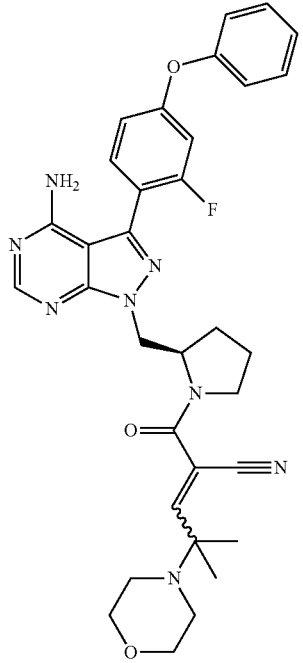 [SMILES: CC(C)(C=C(C#N)C(=O)N1CCC[C@@H]1Cn1nc(-c2ccc(Oc3ccccc3)cc2F)c2c(N)ncnc21)N1CCOCC1]

To a sealed tube was added 3-[(2R)-2-[[4-amino-3-(2-fluoro-4-phenoxy-phenyl)-pyrazolo[3,4-d]pyrimidin-1-yl]methyl]pyrrolidin-1-yl]-3-oxo-propanenitrile (762.6 mg, 1.62 mmol), 2-methyl-2-morpholino-propanal (508.54 mg, 3.23 mmol), piperidine (0.08 mL, 0.81 mmol) and ethanol (6 mL). The tube was sealed and heated at 100° C. After 22 hrs, the reaction was cooled and evaporated. The residue was purified by Isolera (column size 100 g, 3%-7% MeOH/EtOAc) to obtain 550 mg (56% yield) of the title compound. MS (pos. ion) m/z: 611 (M+1).

Example 48

Synthesis of 2-[(2R)-2-[[4-amino-3-(2-fluoro-4-phenoxy-phenyl)pyrazolo[3,4-d]pyrimidin-1-yl]methyl]pyrrolidine-1-carbonyl]-4-methyl-4-(1-piperidyl)pent-2-enenitrile

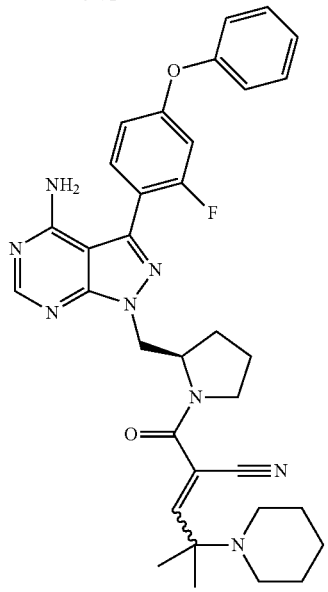 [SMILES: CC(C)(C=C(C#N)C(=O)N1CCC[C@@H]1Cn1nc(-c2ccc(Oc3ccccc3)cc2F)c2c(N)ncnc21)N1CCCCC1]

A solution of 3-[(2R)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (150. mg, 0.32 mmol), piperidine (0.03 mL, 0.32 mmol) and 2-methyl-2-(1-piperidyl)propanal (74.08 mg, 0.48 mmol) in ethanol (8 mL) was heated in a sealed tube at 90° C. for 16 hrs. The solution was cooled and concentrated. The residue was dissolved in ethyl acetate and washed with 5% citric acid and brine and then dried (MgSO₄), filtered and concentrated. The crude material was purified by Isolera (10 grams column at 0% to 6% MeOH/ethyl acetate) to obtain 15 mg (8%) of the title compound. MS (pos. ion) m/z: 609 (M+1).

Example 49

Synthesis of 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-(1-piperidyl)pent-2-enenitrile

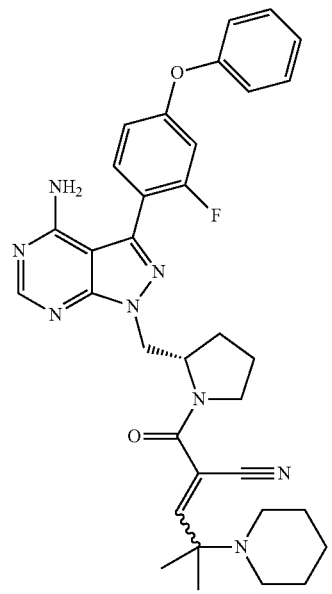 [SMILES: CC(C)(C=C(C#N)C(=O)N1CCC[C@H]1Cn1nc(-c2ccc(Oc3ccccc3)cc2F)c2c(N)ncnc21)N1CCCCC1]

To a microwave vial was added 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (139.3 mg, 0.30 mmol), piperidine (0.04 mL, 0.35 mmol), 2-methyl-2-(1-piperidyl)propanal (68.8 mg, 0.4400 mmol) and toluene (3 mL). The vial was heated under microwave conditions at 160° C. for 3 hrs. The reaction was cooled and concentrated, then dissolved in ethyl acetate (30 mL) and washed with 2M HCl. The aqueous layer was basified to pH~7.5 with sat. NaHCO₃ and washed with ethyl acetate. The organic layer was dried (MgSO₄), filtered and concentrated and the crude material was purified by Isolera (1%-10% MeOH/ethyl acetate) to obtain 32 mg (18%) of the title compound. MS (pos. ion) m/z: 609 (M+1).

Example 50

Synthesis of N-[(1R)-2-[4-amino-3-(2-fluoro-4-phenoxy-phenyl)pyrazolo[3,4-d]pyrimidin-1-yl]-1-methyl-ethyl]-2-cyano-4-ethoxy-4-methyl-pent-2-enamide

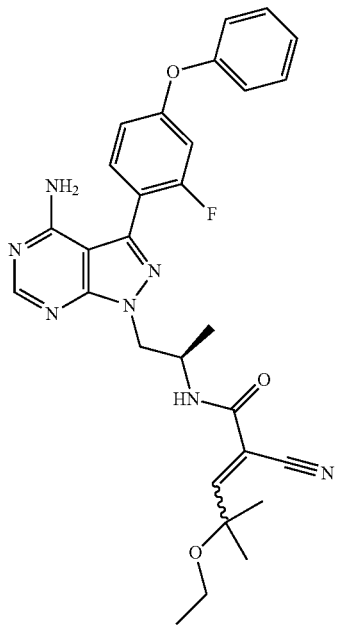 [SMILES: CCOC(C)(C)C=C(C#N)C(=O)N[C@H](C)Cn1nc(-c2ccc(Oc3ccccc3)cc2F)c2c(N)ncnc21]

Step 1

To a solution of tert-butyl N-[(1R)-2-hydroxy-1-methyl-ethyl]carbamate (1.9 g, 10.8 mmol), 3-iodo-1H-pyrazolo[3,4-d]pyrimidin-4-amine (2.0 g, 7.7 mmol), and PPh₃ (6.1 g, 23.2 mmol) in THF (80 mL) cooled with an ice bath was added DIAD (3.0 mL, 15.5 mmol; in 28 mL of THF) dropwise over a 1 hour period. The reaction was then stirred for 24 h at room temperature. The mixture was diluted into ethyl acetate (50 mL) and washed with water and brine. The organic layer was dried (MgSO₄), filtered and concentrated. The resulting material was suspended in 20% ethyl acetate in dioxane (1000 mL) and sonicate for 1 hr. The solid was collected by filtration to obtain 2.1 g (66%) of tert-butyl N-[(1R)-2-(4-amino-3-iodo-pyrazolo[3,4-d]pyrimidin-1-yl)-1-methyl-ethyl]carbamate as a white solid.

Step 2

To a microwave tube was added tert-butyl N-[(1R)-2-(4-amino-3-iodo-pyrazolo[3,4-d]pyrimidin-1-yl)-1-methyl-ethyl]carbamate (1.7 g, 4.1 mmol), (2-fluoro-4-phenoxy-phenyl)boronic acid (1.4 g, 6.1 mmol), K₂CO₃ (1.27 g, 9.2 mmol), and tetrakis(triphenylphosphine)palladium(0) (213 mg, 0.18 mmol) and 1,4-dioxane (12 mL) and water (3 mL). The mixture was capped and heated under microwave conditions for 140° C. for 10 minutes. The reaction was cooled and diluted with ethyl acetate (50 mL) and washed with water (50 mL) and brine. The organic layer was dried (MgSO₄), filtered and evaporated to obtain 2.56 g of crude tert-butyl N-[(1R)-2-[4-amino-3-(2-fluoro-4-phenoxy-phenyl)pyrazolo[3,4-d]pyrimidin-1-yl]-1-methyl-ethyl]carbamate. This was used in the next step without further purification.

Step 3

To a solution of tert-butyl N-[(1R)-2-[4-amino-3-(2-fluoro-4-phenoxy-phenyl)pyrazolo[3,4-d]pyrimidin-1-yl]-1-methyl-ethyl]carbamate (2.56 g, 5.35 mmol) in DCM (20 mL) was added 4N HCl in dioxane (15 ml). After stirring 18 h at room temperature, the reaction was diluted with DCM (100 mL) and extracted with water (200 mL). The aqueous layer was washed again with DCM (50 mL). The aqueous layer was placed in a 2 L beaker along with ethyl acetate (50 mL) and stirred while adding NaOH (beads) to adjust the pH to ~11. More ethyl acetate (100 mL) was added and then the layers were separated and the aqueous layer was washed with ethyl acetate. The combined organic layers were washed with brine and then dried (MgSO₄), filtered and concentrated to obtain 1.8 g (90%) of 1-[(2R)-2-aminopropyl]-3-(2-fluoro-4-phenoxy-phenyl)pyrazolo[3,4-d]pyrimidin-4-amine as a solid.

Step 4

To a solution of 1-[(2R)-2-aminopropyl]-3-(2-fluoro-4-phenoxy-phenyl)pyrazolo[3,4-d]pyrimidin-4-amine (1826. mg, 4.83 mmol), 2-cyanoacetic acid (821 mg, 9.7 mmol) and TEA (2.0 mL, 14.5 mmol) in DMF (25 mL) was added HATU (2.75 g, 7.24 mmol). The reaction mixture was stirred at room temperature for 20 hr. The mixture was then evaporated to an oil and dissolved in ethyl acetate (100 mL) and washed with 5% citric acid (50 mL) and brine. The organic layer was dried (MgSO₄), filtered and evaporated. The crude material was purified by Isolera (10 g col, 2%-6% MeOH/DCM) to obtain 2.1 g (98%) of N-[(1R)-2-[4-amino-3-(2-fluoro-4-phenoxy-phenyl)pyrazolo[3,4-d]pyrimidin-1-yl]-1-methyl-ethyl]-2-cyano-acetamide.

Step 5

To a sealed tube was added N-[(1R)-2-[4-amino-3-(2-fluoro-4-phenoxy-phenyl)pyrazolo[3,4-d]pyrimidin-1-yl]-1-methyl-ethyl]-2-cyano-acetamide (105 mg, 0.24 mmol), piperidine (0.01 mL, 0.12 mmol), 2-ethoxy-2-methyl-propanal (0.07 mL, 0.47 mmol) and ethanol (4 mL). The tube was capped, and heated to 85° C. for 60 hrs. The reaction was cooled and evaporated. The resulting crude oil was dissolved in DCM (30 mL) and washed with water (30 mL) and brine, then dried (MgSO₄), filtered and concentrated. The resulting material was purified by Isolera (10 g column, 3%-7% MeOH/DCM) to obtain 10 mg (8%) of the title compound. MS (pos. ion) m/z: 544 (M+1).

Example 51

Synthesis of 4-amino-N-[(1R)-2-[4-amino-3-(2-fluoro-4-phenoxy-phenyl)pyrazolo[3,4-d]pyrimidin-1-yl]-1-methyl-ethyl]-2-cyano-4-methyl-pent-2-enamide HCl

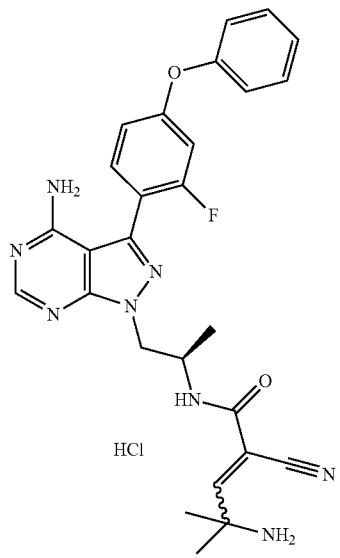 [SMILES: C[C@H](Cn1nc(-c2ccc(Oc3ccccc3)cc2F)c2c(N)ncnc21)NC(=O)C(C#N)=CC(C)(C)N ; Cl]

Step 1

To a sealed tube was added N-[(1R)-2-[4-amino-3-(2-fluoro-4-phenoxy-phenyl)pyrazolo[3,4-d]pyrimidin-1-yl]-1-methyl-ethyl]-2-cyano-acetamide (160 mg, 0.36 mmol), tert-butyl N-(1,1-dimethyl-2-oxo-ethyl)carbamate (0.13 mL, 0.54 mmol) piperidine (0.02 mL, 0.18 mmol) and ethanol (4 mL). The tube was capped and heated to 110° C. for 2 hrs. The reaction was cooled and concentrated then dissolved in ethyl acetate (30 mL) and washed with water (30 mL) and brine. The organic layer was dried (MgSO$_4$), filtered and concentrated. The crude material was purified by isolera (25 g column, 2%-7% MeOH/DCM) to obtain 77 mg, (35%) of tert-butyl N-[4-[[(1R)-2-[4-amino-3-(2-fluoro-4-phenoxy-phenyl)pyrazolo[3,4-d]pyrimidin-1-yl]-1-methyl-ethyl]amino]-3-cyano-1,1-dimethyl-4-oxo-but-2-enyl]carbamate as a solid. MS (pos. ion) m/z: 615 (M+1).

Step 2

To a solution of tert-butyl N-[4-[[(1R)-2-[4-amino-3-(2-fluoro-4-phenoxy-phenyl)pyrazolo[3,4-d]pyrimidin-1-yl]-1-methyl-ethyl]amino]-3-cyano-1,1-dimethyl-4-oxo-but-2-enyl]carbamate (71 mg, 0.12 mmol) in methanol (1 mL) was added 4N HCl in Dioxane (2 mL). The solution was stirred for 4 days and then it was added dropwise to stirring ethyl ether (70 mL). The suspension was stirred for 30 minutes and then filtered and rinse with ethyl ether (10 mL) to obtain 57 mg (95%) of the title compound as an HCl salt.

Example 52

Synthesis of 2-[(2R)-2-[[4-amino-3-(2-fluoro-4-phenoxy-phenyl)pyrazolo[3,4-d]pyrimidin-1-yl]methyl]pyrrolidine-1-carbonyl]-3-[(2S)-pyrrolidin-2-yl]prop-2-enenitrile HCl

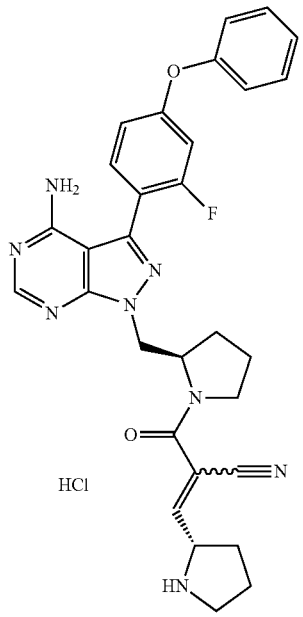 [SMILES: N#CC(=C[C@@H]1CCCN1)C(=O)N1CCC[C@@H]1Cn1nc(-c2ccc(Oc3ccccc3)cc2F)c2c(N)ncnc21 ; Cl]

Step 1

To a sealed tube was added 3-[(2R)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (507 mg, 1.07 mmol), tert-butyl (2S)-2-formylpyrrolidine-1-carboxylate (0.2, mL, 1.1 mmol), piperidine (0.05 mL, 0.54 mmol) and ethanol (3 mL). The tube was capped and heated to 100° C. for 16 hrs. The reaction was not complete so an additional amount of tert-butyl (2S)-2-formylpyrrolidine-1-carboxylate (732 mg, 3 eq) was added and heating was continued for 4 hrs at 110° C. The reaction was cooled and concentrated then dissolved in DCM (50 mL) and washed with water (50 mL) and brine. The organic layer was dried (MgSO$_4$), filtered and concentrated. The resulting material was purified by Isolera (250 g column; 2%-3% MeOH/DCM) to provide 403 mg (57%) of tert-butyl (2S)-2-[3-[(2R)-2-[[4-amino-3-(2-fluoro-4-phenoxy-phenyl)pyrazolo[3,4-d]pyrimidin-1-yl]methyl]pyrrolidin-1-yl]-2-cyano-3-oxo-prop-1-enyl]pyrrolidine-1-carboxylate as a solid.

Step 2

To a solution of tert-butyl (2S)-2-[3-[(2R)-2-[[4-amino-3-(2-fluoro-4-phenoxy-phenyl)pyrazolo[3,4-d]pyrimidin-1-yl]methyl]pyrrolidin-1-yl]-2-cyano-3-oxo-prop-1-enyl]pyrrolidine-1-carboxylate (84 mg, 0.13 mmol) in 1,4-dioxane (2 mL) and added 4N HCl in dioxane (0.16 mL). The solution was stirred for 16 hr at room temperature then concentrated. The residue was dissolved in methanol (~1 mL) and added dropwise to ethyl ether (20 mL) while stirring. The resulting solid was collected by filtration to provide 42 mg (59%) of the title compound as an HCl salt. MS (pos. ion) m/z: 553 (M+1).

Example 53

Synthesis of N—((S)-1-(4-amino-3-(2-fluoro-4-phenoxyphenyl)-1H-pyrazolo[3,4-d]pyrimidin-1-yl)propan-2-yl)-2-cyano-4-methylpent-2-enamide

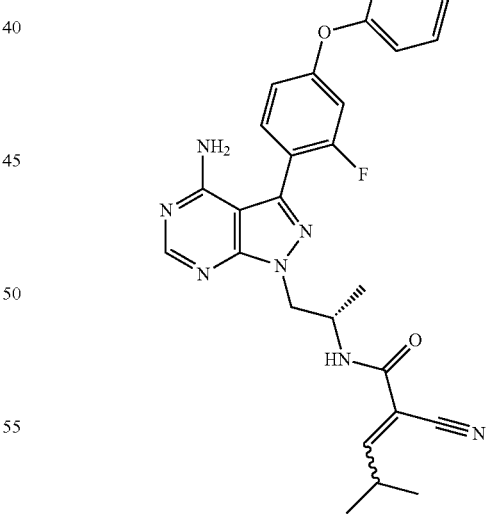

Step 1

Into a 500-mL 3-necked round-bottom flask purged and maintained with an inert atmosphere of nitrogen, to a mixture of 3-iodo-1H-pyrazolo[3,4-d]pyrimidin-4-amine (7.83 g, 30.00 mmol, 1.00 equiv), TPP (11.8 g, 44.99 mmol, 1.50 equiv), tetrahydrofuran (200 mL), tert-butyl N-[(2S)-1-hydroxypropan-2-yl]carbamate (6.3 g, 35.95 mmol, 1.00 equiv) was added DIAD (9.1 g, 45.00 mmol, 1.50 equiv) was added dropwise at 0° C. Most of the solvent was removed under reduced pressure and the solid was collected by filtration, which was washed with pet. ether. This resulted in 5.6 g (45%) of tert-butyl-N-[(2S)-1-[4-amino-3-iodo-1H-pyrazolo[3,4-d]pyrimidin-1-yl]propan-2-yl]carbamate as a yellow powder solid.

Step 2

A mixture of tert-butyl N-[(2S)-1-[4-amino-3-iodo-1H-pyrazolo[3,4-d]pyrimidin-1-yl]propan-2-yl]carbamate (3.5 g, 8.37 mmol, 1.00 equiv), Pd(dppf)Cl$_2$ (310 mg, 0.42 mmol, 0.05 equiv), potassium carbonate (3.5 g, 25.32 mmol, 3.00 equiv), (2-fluoro-4-phenoxyphenyl)boronic acid (2.05 g, 8.84 mmol, 1.10 equiv) in dioxane/H2O (4/1) (50 mL) was stirred for 4 h at 100° C. The resulting mixture was concentrated under vacuum. The residue was applied onto a silica gel column with ethyl acetate/petroleum ether (1/1). This resulted in 3.7 g (92%) of tert-butyl N-[(2S)-1-[4-amino-3-(2-fluoro-4-phenoxyphenyl)-1H-pyrazolo[3,4-d]pyrimidin-1-yl]propan-2-yl]carbamate as a yellow solid.

Step 3

A mixture of tert-butyl N-[(2S)-1-[4-amino-3-(2-fluoro-4-phenoxyphenyl)-1H-pyrazolo[3,4-d]pyrimidin-1-yl]propan-2-yl]carbamate (3.7 g, 7.73 mmol, 1.00 equiv) and trifluoroacetic acid (10 mL) in dichloromethane (40 mL) was stirred at room temperature overnight. The resulting mixture was concentrated under vacuum. This resulted in 4.5 g (crude) of 1-[(2S)-2-aminopropyl]-3-(2-fluoro-4-phenoxyphenyl)-1H-pyrazolo[3,4-d]pyrimidin-4-amine; trifluoroacetic acid as a brown solid.

Step 4

To a mixture of N-[(2R)-1-[4-amino-3-(2-fluoro-4-phenoxyphenyl)-1H-pyrazolo[3,4-d]pyrimidin-1-yl]propan-2-yl]-2,2,2-trifluoroacetamide (4.5 g, 9.49 mmol, 1.00 equiv), triethylamine (4.6 g, 45.4 mmol, 6.00 equiv), 2-cyanoacetic acid (980 mg, 11.52 mmol, 1.50 equiv) in DMF (40 mL) was added HATU (4.4 g, 11.57 mmol, 1.50 equiv). The resulting solution was stirred overnight at room temperature and then diluted with 50 mL of water. The solid was filtrated off and washed with pet. ether. This resulted in 2.5 g (59%, two step) of N-[(2S)-1-[4-amino-3-(2-fluoro-4-phenoxyphenyl)-1H-pyrazolo[3,4-d]pyrimidin-1-yl]propan-2-yl]-2-cyanoacetamide as a yellow solid.

Step 5

A suspension of N-[(2S)-1-[4-amino-3-(2-fluoro-4-phenoxyphenyl)-1H-pyrazolo[3,4-d]pyrimidin-1-yl]propan-2-yl]-2-cyanoacetamide (250 mg, 0.56 mmol, 1.00 equiv), 2-methylpropanal (81 mg, 1.12 mmol, 2.00 equiv) and piperidine (47 mg, 0.55 mmol, 1.00 equiv) in methanol (15 mL) was stirred at room temperature overnight. The resulting mixture was concentrated under vacuum. The residue was applied onto a silica gel column with ethyl acetate/petroleum ether (1/1). The purified product was re-purified on Prep-HPLC eluting with TFA (0.05%)/H$_2$O and CH$_3$CN. The organic phase was removed off under reduced pressure. The aqueous phase was adjusted to 10 with potassium carbonate, which was extracted with DCM. The organic layers were combined, washed with brine, dried over sodium sulfated, filtrated and concentrated. This resulted in 46.4 mg (17%) of the title compound as a white solid. LC-MS m/z: 500 (M+1).

Example 54

2-[(2S)-2-[[4-amino-3-(2-fluoro-4-phenoxy-phenyl)pyrazolo[3,4-d]pyrimidin-1-yl]methyl]-pyrrolidine-1-carbonyl]-3-(3-methyloxetan-3-yl)prop-2-enenitrile

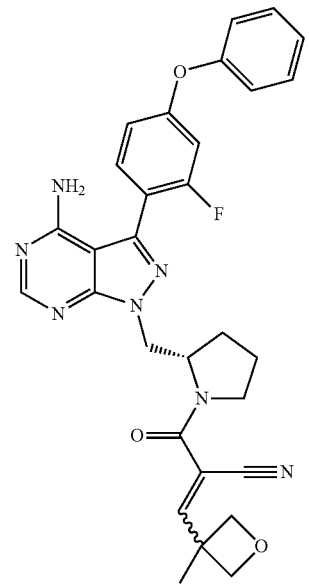 [SMILES: CC1(C=C(C#N)C(=O)N2CCC[C@H]2Cn2nc(-c3ccc(Oc4ccccc4)cc3F)c3c(N)ncnc32)COC1]

To a slurry of 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (74. mg, 0.16 mmol) in ethanol (3 mL) was added 3-methyloxetane-3-carbaldehyde (78.54 mg, 0.78 mmol) and then piperidine (0.02 mL, 0.16 mmol) and the mixture heated to 80° C. with stirring. After 3 h, the mixture was cooled and partitioned between ethyl acetate and water. The organic phase was washed with brine, dried over sodium sulfate, and the filtered. Solvents were removed to afford an oil which was purified by column chromatography (gradient from neat methylene chloride to 95-5 methylene chloride:MeOH). The pure fractions were concentrated, then taken up in acetonitrile/water, frozen and lyophilized to afford 2-[(2S)-2-[[4-amino-3-(2-fluoro-4-phenoxy-phenyl)pyrazolo[3,4-d]pyrimidin-1-yl]methyl]pyrrolidine-1-carbonyl]-3-(3-methyloxetan-3-yl)prop-2-enenitrile as a colorless solid weighing 14 mg.

BIOLOGICAL EXAMPLES

Example 1

Btk Enzymatic Activity Assay

A Caliper-based kinase assay (Caliper Life Sciences, Hopkinton, Mass.) was used to measure inhibition of Btk kinase activity of a compound of Formula (I). Serial dilutions of test compounds were incubated with human recombinant Btk (2 nM), ATP (40 μM) and a phosphoacceptor peptide substrate FAM-GEEPLYWSFPAKKK-NH$_2$ (1 μM) at room temperature for 3 h. The reaction was then terminated with EDTA, final concentration 20 mM and the phosphorylated reaction product was quantified on a Caliper Desktop Profiler (Caliper LabChip 3000). Percent inhibition was calculated for each compound dilution and the concentration that produced 50% inhibition was calculated. This value is presented as the $IC_{50}$. The $IC_{50}$ for a representative no. of compounds of the disclosure are provided below.

| Cpd # (see Embodiment L) | $IC_{50}$ (μm) | Cpd # | $IC_{50}$ (μm) |
|---|---|---|---|
| 1 | 0.0031 | 7 | 0.0013 |
| 2 | 0.0037 | 8 | 0.13 |
| 3 | 0.175 | 9 | 0.98 |
| 4 | 0.061 | 10 | 0.0054 |
| 5 | 0.001 | 11 | 0.014 |
| 6 | 0.365 | 15A | 0.0017 |
| 17A | 0.0021 | 24A | 0.0062 |
| 18A | 0.0023 | 25A | 0.0096 |
| 22A | 0.0018 | 27A | 0.004 |
| 28 | 0.017 | 30A | 0.0017 |
| 31A | 0.002 | 36A | 0.0043 |
| 32A | 0.0017 | 37A | 0.0042 |
| 34 | 0.0048 | 39A | 0.0071 |
| 35A | 0.0044 | 22B | 0.0026 |
| 25B | 0.14 | 44A | 0.005 |
| 27B | 0.0006 | 44B | 0.003 |
| 39B | 0.0038 | 54A | 0.002 |
| 41A | 0.0032 | 56A | 0.0033 |
| 43A | 0.0018 | 57B | 0.01 |
| 63B | 0.033 | 69A | 0.005 |
| 65B | 0.056 | 70A | 0.011 |
| 67 | 0.027 | 72A | 0.0016 |
| 42A | 0.0028 | 72B | 0.028 |
| 73B | 0.011 | 79B | 0.003 |
| 77B | 0.007 | 59B | 0.026 |
| 71A | 0.007 | 80B | 0.004 |
| 74B | 0.008 | 81A | 0.0044 |
| 75B | 0.10 | 81B | 0.0059 |
| 76B | 0.007 | 82A | 0.0022 |
| 78B | 0.0075 | 82B | 0.113 |
| 87B | 0.012 | 83A | 0.0014 |
| 84A | 0.0036 | 83B | 0.016 |
| 84B | 0.0004 | 85A | 0.0004 |
| 85B | 0.0172 | 89A | 3.1 |
| 87B | 0.012 | 89B | 6.6 |
| 88B | 0.029 | 90A | 0.052 |
| 95A | 0.0265 | 95B | 0.0032 |
| 102A | 0.002 | 102B | 0.006 |
| 104A | 0.001 | 104B | 0.020 |
| 105A | 0.0013 | 105B | 0.0255 |
| 106A | 0.006 | 124A | 0.002 |
| 106B | 0.0015 | 126A | 0.003 |
| 133A | 0.007 | 139A | 0.0007 |
| 156A | 0.0073 | 171B | 0.007 |
| 173B | 0.034 | 175A | 0.003 |
| 175B | 0.001 | 182B | 0.002 |
| 183B | 0.003 | 184B | 0.005 |
| 185B | 0.011 | 186 | 0.0037 |
| 188 | 0.0007 | 195 | 0.006 |
| 180A | 0.037 | 180B | 0.004 |
| 162A | 0.0009 | 197B | 0.0325 |
| 29 A | 0.0027 | 125 A | 0.002 |

Example 2

Mouse Dry Eye Model . . . In Vivo Assay

The ability of the compounds of the present disclosure to treat dry eye can be tested using the scopolamine mouse dry eye model. Briefly, female mice (C57/B6), aged 6-8 weeks, are treated with subcutaneous scopolamine hydrobromide 3×d and exposed to an air draft (blower) for 3 weeks. Treatment is initiated at time of dessicating stress induction. Clinical observations are made daily, and body weights determined weekly. Efficacy is assessed by slit lamp examination with flourescein dye and phenol red thread tests three times per week, and tear break up test at the end of study. At the end of the study, eyes are collected after enucleation, and one eye fixed in Davidson's for histopathology, and one eye frozen for cytokine and PD determinations. Control mice are kept in a non-stressed environment maintained at 50% to 75% relative humidity without exposure to forced air or scopolamine.

Example 3

Recovery of BTK Activity Upon Dialysis

Standard experimental methods to establish reversibility are known in the art. Protein dialysis is one such method. A solution containing BTK that is inhibited by a reversible or irreversible covalent BTK inhibitor (e.g. a compound of Formula I) may be subjected to extensive dialysis to establish if the inhibitor is reversible or irreversible covalent inhibitor. Partial or complete recovery of protein kinase activity over time during dialysis is indicative of reversibility.

Method:

A reversible or irreversible covalent BTK inhibitor (1 μM) is added to a solution of protein kinase (50 nM, pre-activated if necessary) in a buffer containing 20 mM Hepes [pH 8.0], 10 mM $MgCl_2$, 2.5 mM tris(2-carboxyethyl)phosphine (TCEP), 0.25 mg/mL BSA, and 100 μM ATP. After 60 min at rt, the reaction is transferred to a dialysis cassette (0.1-0.5 mL Slide-A-Lyzer, MWCO 10 kDa, Pierce) and dialyzed against 2 L of buffer (20 mM Hepes [pH 8.0], 10 mM $MgCl_2$, 1 mM DTT) at 4° C. The dialysis buffer is exchanged after 2 h, and then is exchanged every 24 h until the end of the experiment. Aliquots are removed from the dialysis cassettes every 24 h, flash frozen in liquid nitrogen, and subsequently analyzed for BTK activity in triplicate. BTK activity for each sample is normalized to the DMSO control for that time point and expressed as the mean±SD.

Results: BTK activity recovers from inhibition by reversible covalent inhibitors upon dialysis. Upon extensive dialysis at 4° C. or at room temperature, BTK activity partially or completely recovers in a time-dependent manner from inhibition by an excess (20 equiv, 1.0 μM) of reversible covalent BTK inhibitor.

Example 4

Mass Spectral Analysis

BTK that is inhibited by a reversible or irreversible covalent inhibitor may be subjected to mass spectral analysis to assess the formation of permanent, irreversible covalent adducts. Suitable analytical methods to examine intact full protein or peptide fragments generated upon tryptic cleavage of BTK are generally known in the art. Such methods identify permanent, irreversible covalent protein adducts by observing a mass peak that corresponds to the mass of a control sample plus the mass of an irreversible adduct. One such methods are described below.

Mass Spectral Analysis of Intact Full Kinase

Method:

BTK (5 μM) is incubated with a reversible or irreversible covalent inhibitor (25 μM, 5 equiv) for 1 h at room temperature in buffer (20 mM Hepes [pH 8.0], 100 mM NaCl, 10 mM $MgCl_2$). A control sample is also prepared which does not have the reversible or irreversible covalent inhibitor, respectively. The reaction is stopped by adding an equal volume of 0.4% formic acid, and the samples are analyzed by liquid chromatography (Microtrap C18 Protein column

[Michrom Bioresources], 5% MeCN, 0.2% formic acid, 0.25 ml/min; eluted with 95% MeCN, 0.2% formic acid) and in-line ESI mass spectrometry (LCT Premier, Waters). Molecular masses of BTK and any adducts may be determined with MassLynx deconvolution software.

Results: High-resolution intact mass spectrometry analysis of BTK that is inhibited by a reversible covalent inhibitor will reveal a spectrum similar to the BTK in the absence of inhibitor (e.g. control sample). There will be no formation of a new peak in the mass spectrum corresponding to the molecular mass BTK plus the molecular mass of the compound. On the basis of this experiment no permanent, irreversible protein adduct will be apparent to one skilled in the art. If the compound is an irreversible covalent BTK inhibitor, a new peak in the mass spectrum corresponding to the molecular mass BTK plus the molecular mass of the compound will be observed.

Example 5

Determination of Drug-Kinase Residence Time for BTK

The following is a protocol to distinguish whether a compound displays a slow or non-existent dissociation rate from BTK, such as typically would occur if an irreversible covalent bond is formed between the compound and the target. The read-out for slow dissociation is the ability of the compound of interest to block binding of a high affinity fluorescent tracer molecule to the kinase active site, as detected using time-resolved fluorescence resonance energy transfer (TR-FRET). The experiment was conducted in a buffer consisting of 50 mM Hepes pH 7.5, 10 mM MgCl$_2$, 0.01% Triton X-100, and 1 mM EGTA.

The first step of the procedure was incubation of 500 nM BTK (Invitrogen Cat. #PV3587) with 1.5 μM of a compound of Formula (I) where R$^b$ is other than hydrogen, for 30 minutes in a volume of 10 μL. The mixture was then diluted 5-fold by addition of 40 μL of buffer. A 10 μL volume of the diluted kinase/compound solution was then added to a well of a small volume 384 well plate (such as Greiner Cat. #784076). In order to probe for reversibility of the kinase-compound binding interaction, a competition solution containing both a high affinity fluorescent tracer and an antibody coupled to Europium was prepared. For BTK, the competition solution contained 1.5 μM Tracer 178 (Invitrogen Cat. #PV5593), which is a proprietary high affinity ligand for BTK coupled to the fluorophore AlexaFluor 647. The competition solution also contained 80 nM of an Anti-polyhistidine antibody coupled to Europium (Invitrogen Cat. #PV5596) which is designed to bind the polyhistidine purification tag in BTK.

After addition of 10 μL of the competition solution to the Greiner plate, the mixture was incubated for one hour or greater to allow time for dissociation of non-covalent inhibitors and binding of the high affinity tracer. It was expected that covalent and slow dissociating inhibitors will block binding of the tracer while rapidly dissociating non-covalent inhibitors will not. Binding of the tracer to BTK was detected using TR-FRET between the Europium moiety of the Anti-histidine antibody and the AlexaFluor 647 group of Tracer 178. Binding was evaluated using a Perkin Elmer Envision instrument (Model 2101) equipped with filters and mirrors compatible with LANCE-type TR-FRET experiments. Data were plotted at percentage of signal obtained in the absence of competitor compound. The background signal was obtained by omission of BTK from the reaction.

Example 6

Reversibility of Binding

The following approach was developed to differentiate compounds that form irreversible bonds with their targets, such as acrylamide compounds, from compound that bind reversibly such as reversible covalent inhibitors. Reactions were prepared with the protein target at a higher concentration than the compounds of interest. Both irreversible and reversible compounds bound the target and became depleted from solution. The reactions were then treated with perturbations including both denaturation with 5 M guanidine hydrochloride and digestion with trypsin, disrupting proper folding of the target. It was found that the perturbation returned reversible compounds to solution due to dissociation from the target while irreversible compounds remained bound to the target. The concentration of compound in solution was assessed both preceding and following perturbation using high performance liquid chromatography (HPLC) coupled to tandem mass spectrometry. Using this technique, it was demonstrated that an acrylamide-containing compound 1 (shown in table below) was depleted from solution in both the native and perturbed state, while reversible compounds 1 and 27 were depleted in the folded state but returned to solution following perturbation of the target (See table below).

| Compound | Compound in solution in the native state? | Compound in solution in the denatured or digested state? |
|---|---|---|
| 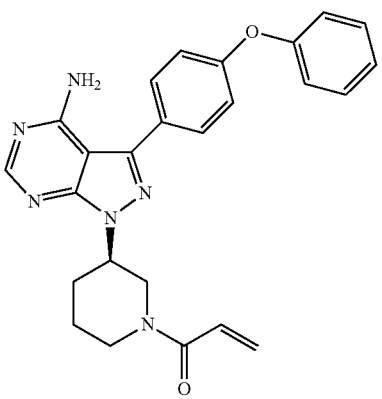<br>Irreversible inhibitor | no | no |

| Compound | Compound in solution in the native state? | Compound in solution in the denatured or digested state? |
| --- | --- | --- |
| 1 | no | yes |
| 27A | no | yes |

The foregoing disclosure has been described in some detail by way of illustration and example, for purposes of clarity and understanding. It will be obvious to one of skilled in the art that changes and modifications may be practiced within the scope of the appended claims. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

What is claimed:

1. A method of treating dry eye disease in a patient in need of such treatment comprising topically administering to the eye of said patient a therapeutically effective amount of a BTK inhibitor, wherein the BTK inhibitor is a compound of Formula (I):

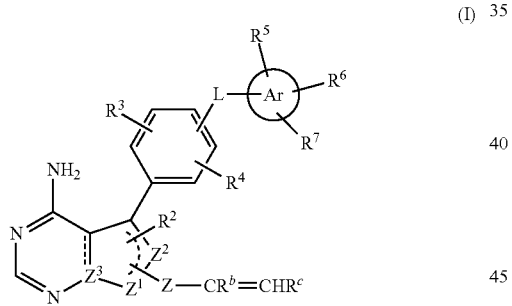

wherein:
dashed lines are an optional bond;
$Z^1$, $Z^2$, and $Z^3$ are —N— or —CH—, provided that one of $Z^1$, $Z^2$, and $Z^3$ is —N—, or two of $Z^1$, $Z^2$, and $Z^3$ are simultaneously, —N—;
L is O, NR, or NR'CONR where (each R and R' is independently hydrogen or alkyl);
Ar is aryl, heteroaryl, cycloalkyl or heterocyclyl;
$R^2$ is hydrogen, alkyl, hydroxy, alkoxy, cyano, halo or haloalkyl;
$R^3$ and $R^4$ are independently hydrogen, alkyl, cyclopropyl, hydroxy, alkoxy, cyano, halo, haloalkyl or haloalkoxy;
$R^5$, $R^6$ and $R^7$ are independently hydrogen, alkyl, hydroxy, alkoxy, halo, haloalkyl, haloalkoxy, carboxy, alkoxycarbonyl, cyano, —CONH$_2$, amino, alkylamino, or dialkylamino;

Z is -alkyleneCO—, -alkyleneOCO—, -alkyleneSO$_2$—,

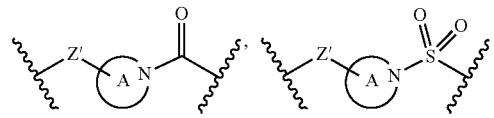

(where Z' is bond or alkylene, and ring A is heterocycloamino optionally substituted with one or two substituents independently selected from alkyl, hydroxy, or fluoro), -(alkylene)-NR$^a$CO— or -(alkylene)-NR$^a$SO$_2$— (where each R$^a$ is hydrogen, alkyl or cycloalkyl);
$R^b$ is hydrogen, cyano, nitro, halo, haloalkyl, haloalkoxy, alkylthio, or alkylsulfonyl;
$R^c$ is hydrogen, alkyl, haloalkoxy, substituted alkyl, cycloalkyl, cycloalkyleneNR$^d$R$^e$ (where R$^d$ and R$^e$ are independently hydrogen, alkyl, or cycloalkyl), or a 3 to 6 membered saturated monocyclic heterocyclyl containing one or two heteroatoms selected from N, O, and S and optionally substituted with one or two substituents independently selected from hydroxy, alkyl and fluoro; and/or
a pharmaceutically acceptable salt thereof.

2. The method of claim 1 wherein the dry eye disease is not associated with Sjogren's syndrome.

3. The method of claim 1 wherein R$^b$ is cyano.

4. A method of treating dry eye disease in a patient in need of such treatment comprising topically administering to the eye of said patient a therapeutically effective amount of a BTK inhibitor, wherein the BTK inhibitor is:
(R)-2-(2-((4-amino-3-(4-(3-fluorophenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(4-(3-fluorophenoxy)phenyl)-1H-pyrazolo[3,4-d]pyrimidin-1-yl)methyl)pyrrolidine-1-carbonyl)-3-cyclopropylacrylonitrile;
(R)-2-(2-((4-amino-3-(4-(3,5-difluorophenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(4-(3,5-difluorophenoxy)phenyl)-1H-pyrazolo[3,4-d]pyrimidin-1-yl)methyl) pyrrolidine-1-carbonyl)-3-cyclopropylacrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile;
(R)-2-(2-((4-amino-3-(4-(2,3-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(4-(2,3-difluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(4-(2,6-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(4-(2,6-difluorophenoxy)phenyl)-1H-pyrazolo[3,4-d]pyrimidin-1-yl)methyl)pyrrolidine-1-carbonyl)-3-cyclopropylacrylonitrile;

(R)-2-(3-(4-amino-3-(4-(2-fluorophenoxy)phenyl)-1H-pyrazolo[3,4-d]pyrimidin-1-yl)piperidine-1-carbonyl)-3-cyclopropylacrylamide;

(S)-2-(3-(4-amino-3-(4-(2-fluorophenoxy)phenyl)-1H-pyrazolo[3,4-d]pyrimidin-1-yl)piperidine-1-carbonyl)-3-cyclopropylacrylamide;

(R)-2-(3-(4-amino-3-(4-(2,3-difluorophenoxy)phenyl)-1H-pyrazolo[3,4-d]pyrimidin-1-yl)piperidine-1-carbonyl)-3-cyclopropylacrylamide;

(S)-2-(3-(4-amino-3-(4-(2,3-difluorophenoxy)phenyl)-1H-pyrazolo[3,4-d]pyrimidin-1-yl)piperidine-1-carbonyl)-3-cyclopropylacrylamide;

(R)-2-(3-(4-amino-3-(4-(2,6-difluorophenoxy)phenyl)-1H-pyrazolo[3,4-d]pyrimidin-1-yl)piperidine-1-carbonyl)-3-cyclopropylacrylamide;

(S)-2-(3-(4-amino-3-(4-(2,6-difluorophenoxy)phenyl)-1H-pyrazolo[3,4-d]pyrimidin-1-yl)piperidine-1-carbonyl)-3-cyclopropylacrylamide;

(R)-2-(3-(4-amino-3-(4-(2,5-difluorophenoxy)phenyl)-1H-pyrazolo[3,4-d]pyrimidin-1-yl)piperidine-1-carbonyl)-3-cyclopropylacrylamide;

(S)-2-(3-(4-amino-3-(4-(2,5-difluorophenoxy)phenyl)-1H-pyrazolo[3,4-d]pyrimidin-1-yl)piperidine-1-carbonyl)-3-cyclopropylacrylamide;

(R)-2-(2-((4-amino-3-(4-(2-fluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(4-(2-fluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(4-(2,5-difluorophenoxy)phenyl)-1H-pyrazolo[3,4-d]pyrimidin-1-yl)methyl)pyrrolidine-1-carbonyl)-3-cyctopropylacrylonitrile;

(S)-2-(2-((4-amino-3-(4-(2,5-difluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-fluoro-4-(3,5-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-fluoro-4-(3,5-difluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(3-fluoro-4-(phenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(3-fluoro-4-(phenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-fluoro-4-(2,3-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-fluoro-4-(2,3-difluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-fluoro-4-(2,6-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-fluoro-4-(2,6-difluorophenoxy)phenyl)-1H-pyrazolo[3,4-d]pyrimidin-1-yl)methyl)pyrrolidine-1-carbonyl)-3-cyclopropylacrylonitrile;

N-(2-(4-amino-3-(2-fluoro-4-phenoxyphenyl)-1H-pyrazolo[3,4-d]pyrimidin-1-yl)ethyl)-2-cyano-3-cyclopropylacrylamide;

N-(2-(4-amino-3-(2-fluoro-4-phenoxyphenyl)-1H-pyrazolo[3,4-d]pyrimidin-1-yl)-2-methylpropyl)-2-cyano-3-cyclopropylacrylamide;

N-(1-(4-amino-3-(2-fluoro-4-phenoxyphenyl)-1H-pyrazolo[3,4-d]pyrimidin-1-yl)-2-methylpropan-2-yl)-2-cyano-3-cyclopropylacrylamide;

N-(2-(4-amino-3-(2-fluoro-4-phenoxyphenyl)-1H-pyrazolo[3,4-d]pyrimidin-1-yl)ethyl)-1-cyano-2-cyclopropylethenesulfonamide;

N-(2-(4-amino-3-(2-fluoro-4-phenoxyphenyl)-1H-pyrazolo[3,4-d]pyrimidin-1-yl)ethyl)-1-cyano-2-cyclopropyl-N-methylethenesulfonamide;

2-(4-amino-3-(2-fluoro-4-phenoxyphenyl)-1H-pyrazolo[3,4-d]pyrimidin-1-yl)ethyl 2-cyano-3-cyclopropylacrylate;

1-(4-amino-3-(2-fluoro-4-phenoxyphenyl)-1H-pyrazolo[3,4-d]pyrimidin-1-yl)-2-methylpropan-2-yl 2-cyano-3-cyclopropylacrylate;

2-((2-(4-amino-3-(2-fluoro-4-phenoxyphenyl)-1H-pyrazolo[3,4-d]pyrimidin-1-yl)ethyl)sulfonyl)-3-cyclopropylacrylonitrile;

2-(5-((4-amino-3-(2-fluoro-4-phenoxyphenyl)-1H-pyrazolo[3,4-d]pyrimidin-1-yl)methyl)oxazol-2-yl)-3-cyclopropylacrylonitrile;

(R)-2-(3-(4-amino-5-(4-(3,5-difluorophenoxy)phenyl)-7H-pyrrolo[2,3-d]pyrimidin-7-yl)piperidine-1-carbonyl)-3-cyclopropylacrylonitrile;

(S)-2-(3-(4-amino-5-(4-(3,5-difluorophenoxy)phenyl)-7H-pyrrolo[2,3-d]pyrimidin-7-yl)piperidine-1-carbonyl)-3-cyclopropylacrylonitrile;

(R)-2-(3-(4-amino-5-(2-fluoro-4-phenoxyphenyl)-7H-pyrrolo[2,3-d]pyrimidin-7-yl)piperidine-1-carbonyl)-3-cyclopropylacrylonitrile;

(S)-2-(3-(4-amino-5-(2-fluoro-4-phenoxyphenyl)-7H-pyrrolo[2,3-d]pyrimidin-7-yl)piperidine-1-carbonyl)-3-cyclopropylacrylonitrile;

(R)-2-(2-((4-amino-5-(4-(3,5-difluorophenoxy)phenyl)-7H-pyrrolo[2,3-d]pyrimidin-7-yl)methyl)pyrrolidine-1-carbonyl)-3-cyclopropylacrylonitrile;

(S)-2-(2-((4-amino-5-(4-(3,5-difluorophenoxy)phenyl)-7H-pyrrolo[2,3-d]pyrimidin-7-yl)methyl)pyrrolidine-1-carbonyl)-3-cyclopropylacrylonitrile;

(R)-2-(2-((4-amino-5-(2-fluoro-4-phenoxyphenyl)-7H-pyrrolo[2,3-d]pyrimidin-7-yl)methyl)pyrrolidine-1-carbonyl)-3-cyclopropylacrylonitrile;

(S)-2-(2-((4-amino-5-(2-fluoro-4-phenoxyphenyl)-7H-pyrrolo[2,3-d]pyrimidin-7-yl)methyl)pyrrolidine-1-carbonyl)-3-cyclopropylacrylonitrile;

(R)-2-(3-(4-amino-5-(4-(3,5-difluorophenoxy)phenyl)-6-methyl-7H-pyrrolo[2,3-d]pyrimidin-7-yl)piperidine-1-carbonyl)-3-cyclopropylacrylonitrile;

(S)-2-(3-(4-amino-5-(4-(3,5-difluorophenoxy)phenyl)-6-methyl-7H-pyrrolo[2,3-d]pyrimidin-7-yl)piperidine-1-carbonyl)-3-cyclopropylacrylonitrile;

2-((3R)-3-(4-amino-5-(2-fluoro-4-phenoxyphenyl)-6-methyl-7H-pyrrolo[2,3-d]pyrimidin-7-yl)piperidine-1-carbonyl)-3-cyclopropylacrylonitrile;

2-((3S)-3-(4-amino-5-(2-fluoro-4-phenoxyphenyl)-6-methyl-7H-pyrrolo[2,3-d]pyrimidin-7-yl)piperidine-1-carbonyl)-3-cyclopropylacrylonitrile;

(R)-2-(2-((4-amino-5-(4-(3,5-difluorophenoxy)phenyl)-6-methyl-7H-pyrrolo[2,3-d]pyrimidin-7-yl)methyl)pyrrolidine-1-carbonyl)-3-cyclopropylacrylonitrile;

(S)-2-(2-((4-amino-5-(4-(3,5-difluorophenoxy)phenyl)-6-methyl-7H-pyrrolo[2,3-d]pyrimidin-7-yl)methyl)pyrrolidine-1-carbonyl)-3-cyclopropylacrylonitrile;

(R)-2-(2-((4-amino-5-(2-fluoro-4-phenoxyphenyl)-6-methyl-7H-pyrrolo[2,3-d]pyrimidin-7-yl)methyl)pyrrolidine-1-carbonyl)-3-cyclopropylacrylonitrile;

(S)-2-(2-((4-amino-5-(2-fluoro-4-phenoxyphenyl)-6-methyl-7H-pyrrolo[2,3-d]pyrimidin-7-yl)methyl) pyrrolidine-1-carbonyl)-3-cyclopropylacrylonitrile;

(R)-2-(2-((4-amino-3-(2-methyl-4-phenoxyphenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-methyl-4-phenoxyphenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-chloro-4-phenoxyphenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-chloro-4-phenoxyphenyl)-1H-pyrazolo[3,4-d]pyrimidin-1-yl)methyl)pyrrolidine-1-carbonyl)-3-cyclopropylacrylonitrile;

(R)-2-(2-((4-amino-3-(4-(2,5-difluorophenoxy)phenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,5-difluorophenoxy)phenyl)-1H-pyrazolo[3,4-d]pyrimidin-1-yl)methyl)pyrrolidine-1-carbonyl)-4-methylpent-2-enenitrile;

(R)-4-amino-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;

(S)-4-amino-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;

(R)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;

(S)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4,4-dimethylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4,4-dimethylpent-2-enenitrile;

(R)-2-(2-((4-amino-3-(4-(2,6-difluorophenoxy)phenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,6-difluorophenoxy)phenyl)-1H-pyrazolo[3,4-d]pyrimidin-1-yl)methyl) pyrrolidine-1-carbonyl)-4-methylpent-2-enenitrile;

(R)-2-(2-((4-amino-3-(4-(2,3-difluorophenoxy)phenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,3-difluorophenoxy)phenyl)-1H-pyrazolo[3,4-d]pyrimidin-1-yl)methyl)pyrrolidine-1-carbonyl)-4-methylpent-2-enenitrile;

(R)-2-(2-((4-amino-3-(4-(2,6-difluorophenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,6-difluorophenoxy)-2-fluorophenyl)-1H-pyrazolo[3,4-d]pyrimidin-1-yl)methyl)pyrrolidine-1-carbonyl)-4-methylpent-2-enenitrile;

(R)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-3-cyclopropylacrylonitrile;

(S)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-3-cyclopropylacrylonitrile;

(R)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-4-methylpent-2-enenitrile;

(S)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(S)-4-amino-2-(2-((4-amino-3-(2-fluoro-4-phenoxyphenyl)-1H-pyrazolo[3,4-d]pyrimidin-1-yl)methyl) pyrrolidine-1-carbonyl)-4-methylpent-2-enenitrile;

(R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(methylamino) pent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(methylamino)pent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(dimethylamino)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(dimethylamino)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(isopropylamino)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(isopropylamino)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropylamino)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropylamino)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-((2-methoxyethyl)amino)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-((2-methoxyethyl)amino)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-ethoxy-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-ethoxy-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-aminocyclopropyl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-aminocyclopropyl)acrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(methylamino)cyclopropyl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(methylamino)cyclopropyl)acrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(ethylamino)cyclopropyl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(ethylamino)cyclopropyl)acrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(isopropylamino)cyclopropyl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(isopropylamino)cyclopropyl)acrylonitrile;

2-((S)-2-((4-amino-3-(2-fluoro-4-phenoxyphenyl)-1H-pyrazolo[3,4-d]pyrimidin-1-yl)methyl)pyrrolidine-1-carbonyl)-3-(pyrrolidin-2-yl)acrylonitrile;

2-((R)-2-((4-amino-3-(2-fluoro-4-phenoxyphenyl)-1H-pyrazolo[3,4-d]pyrimidin-1-yl)methyl)pyrrolidine-1-carbonyl)-3-(pyrrolidin-2-yl)acrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-((dimethylamino)methyl)cyclopentyl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-((dimethylamino)methyl)cyclopentyl)acrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-methylpiperidin-4-yl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-methylpiperidin-4-yl)acrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(tetrahydro-2H-pyran-4-yl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(tetrahydro-2H-pyran-4-yl)acrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(piperidin-4-yl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(piperidin-4-yl)acrylonitrile;

2-((S)-2-((4-amino-3-(2-fluoro-4-phenoxyphenyl)-1H-pyrazolo[3,4-d]pyrimidin-1-yl)methyl)pyrrolidine-1-carbonyl)-3-(piperidin-3-yl)acrylonitrile;

2-((R)-2-((4-amino-3-(2-fluoro-4-phenoxyphenyl)-1H-pyrazolo[3,4-d]pyrimidin-1-yl)methyl)pyrrolidine-1-carbonyl)-3-(piperidin-3-yl)acrylonitrile;

(S)-2-(2-((4-amino-3-(4-(2,3-difluorophenyl)-1H-pyrazolo[3,4-d]pyrimidin-1-yl)methyl)pyrrolidine-1-carbonyl)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4,4-dimethylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4,4-dimethylpent-2-enenitrile;

(S)-4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;

(R)-4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-(methylamino)pent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-(methylamino)pent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(dimethylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(dimethylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(ethylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(ethylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(isopropylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(isopropylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(cyclopropylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(cyclopropylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-((2-methoxyethyl)amino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-((2-methoxyethyl)amino)-4-methylpent-2-enenitrile;

(S)-2-(2-((4-amino-3-(4-(2,3-di fluorophenyl)-1H-pyrazolo[3,4-d]pyrimidin-1-yl)methyl)pyrrolidine-1-carbonyl)-4-ethoxy-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-ethoxy-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-aminocyclopropyl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-aminocyclopropyl)acrylonitrile;

(S)-2-(2-((4-amino-3-(4-(2,3-difluorophenyl)-1H-pyrazolo[3,4-d]pyrimidin-1-yl)methyl)pyrrolidine-1-carbonyl)-3-(1-(methylamino)cyclopropyl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(methylamino)cyclopropyl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(ethylamino)cyclopropyl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(ethylamino)cyclopropyl)acrylonitrile;

(S)-2-(2-((4-amino-3-(4-(2,3-difluorophenyl)-1H-pyrazolo[3,4-d]pyrimidin-1-yl)methyl)pyrrolidine-1-carbonyl)-3-(1-(isopropylamino)cyclopropyl)-acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(isopropylamino)cyclopropyl)-acrylonitrile;

2-((S)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(pyrrolidin-2-yl)acrylonitrile;

2-((R)-2-((4-amino-3-(4-(2,3-difluorophenyl)-1H-pyrazolo[3,4-d]pyrimidin-1-yl)methyl)pyrrolidine-1-carbonyl)-3-(pyrrolidin-2-yl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-morpholinopent-2-enenitrile;

(R)-2-(2-((4-amino-3-(4-(2,3-difluorophenyl)-1H-pyrazolo[3,4-d]pyrimidin-1-yl)methyl)pyrrolidine-1-carbonyl)-4-methyl-4-morpholinopent-2-enenitrile;

(S)-2-(2-((4-amino-3-(4-(2,3-difluorophenyl)-1H-pyrazolo[3,4-d]pyrimidin-1-yl)methyl)pyrrolidine-1-carbonyl)-3-(1-((diethylamino)methyl)cyclopentyl)-acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((diethylamino)methyl)cyclopentyl)-acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((dimethylamino)methyl)cyclopentyl)-acrylonitrile;

(R)-2-(2-((4-amino-3-(4-(2,3-difluorophenyl)-1H-pyrazolo[3,4-d]pyrimidin-1-yl)methyl)pyrrolidine-1-carbonyl)-3-(1-((dimethylamino)-methyl)-cyclopentyl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-methylpiperidin-4-yl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-methylpiperidin-4-yl)acrylonitrile;

(S)-2-(2-((4-amino-3-(4-(2,3-difluorophenyl)-1H-pyrazolo[3,4-d]pyrimidin-1-yl)methyl)pyrrolidine-1-carbonyl)-3-(tetrahydro-2H-pyran-4-yl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(tetrahydro-2H-pyran-4-yl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-4-yl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-4-yl)acrylonitrile;

2-((S)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-3-yl)acrylonitrile;

2-((R)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-3-yl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;

(R)-4-amino-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;

(S)-4-amino-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(methylamino)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(methylamino)pent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(dimethylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(dimethylamino)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(ethylamino)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(ethylamino)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(isopropylamino)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(isopropylamino)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(cyclopropylamino)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(cyclopropylamino)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-((2-methoxyethyl)amino)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-((2-methoxyethyl)amino)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-aminocyclopropyl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-aminocyclopropyl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-(methylamino)cyclopropyl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-(methylamino)cyclopropyl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-(ethylamino)cyclopropyl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-(ethylamino)cyclopropyl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-(isopropylamino)cyclopropyl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-(isopropylamino)cyclopropyl)acrylonitrile;

2-((R)-3-(4-amino-3-(2-fluoro-4-phenoxyphenyl)-1H-pyrazolo[3,4-d]pyrimidin-1-yl)piperidine-1-carbonyl)-3-(pyrrolidin-2-yl)acrylonitrile;

2-((S)-3-(4-amino-3-(2-fluoro-4-phenoxyphenyl)-1H-pyrazolo[3,4-d]pyrimidin-1-yl)piperidine-1-carbonyl)-3-(pyrrolidin-2-yl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-morpholinopent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-((diethylamino)methyl)-cyclopentyl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-((diethylamino)methyl)-cyclopentyl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-((dimethylamino)methyl)cyclopentyl)-acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-((dimethylamino)methyl)cyclopentyl)-acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-methylpiperidin-4-yl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-methylpiperidin-4-yl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(tetrahydro-2H-pyran-4-yl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(tetrahydro-2H-pyran-4-yl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(piperidin-4-yl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(piperidin-4-yl)acrylonitrile;

2-((R)-3-(4-amino-3-(2-fluoro-4-phenoxyphenyl)-1H-pyrazolo[3,4-d]pyrimidin-1-yl)piperidine-1-carbonyl)-3-(piperidin-3-yl)acrylonitrile;

2-((S)-3-(4-amino-3-(2-fluoro-4-phenoxyphenyl)-1H-pyrazolo[3,4-d]pyrimidin-1-yl)piperidine-1-carbonyl)-3-(piperidin-3-yl)acrylonitrile;

(R)-2-(3-(4-amino-3-(4-(2,3-difluorophenyl)-1H-pyrazolo[3,4-d]pyrimidin-1-yl)piperidine-1-carbonyl)-3-cyclopropylacrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-cyclopropylacrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4,4-dimethylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4,4-dimethylpent-2-enenitrile;

(R)-4-amino-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(S)-4-amino-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-(methylamino)pent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-(methylamino)pent-2-enenitrile;

(R)-2-(3-(4-amino-3-(4-(2,3-difluorophenoxy)-2-frophenyl)-1H-pyrazolo[3,4-d]pyrimidin-1-yl)piperidine-1-carbonyl)-4-(dimethylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(dimethylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(ethylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(ethylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(isopropylamino)-4-methylpent-2-enenitrile;

(S)-2-(3-(4-amino-3-(4-(2,3-difluorophenoxy)-(2-fluorophenyl)-1H-pyrazolo[3,4-d]pyrimidin-1-yl)piperidine-1-carbonyl)-4-(isopropylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(cyclopropylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(cyclopropylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-((2-methoxyethyl)amino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-((2-methoxyethyl)amino)-4-methylpent-2-enenitrile;

(R)-2-(3-(4-amino-3-(4-(2,3-difluorophenyl)-1H-pyrazolo[3,4-d]pyrimidin-1-yl)piperidine-1-carbonyl)-4-ethoxy-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-ethoxy-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-aminocyclopropyl)-acrylonitrile;

(S)-2-(3-(4-amino-3-(4-(2,3-di fluorophenyl)-1H-pyrazolo[3,4-d]pyrimidin-1-yl)piperidine-1-carbonyl)-3-(1-aminocyclopropyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(methylamino)cyclopropyl)-acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(methylamino)cyclopropyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(ethylamino)cyclopropyl)-acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(ethylamino)cyclopropyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(isopropylamino)-cyclopropyl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(isopropylamino)-cyclopropyl)acrylonitrile;

2-((R)-3-(4-amino-3-(4-(2,3-difluorophenoxy)-2-fluorophenyl)-1H-pyrazolo[3,4-d]pyrimidin-1-yl)piperidine-1-carbonyl)-3-(pyrrolidin-2-yl)acrylonitrile;

2-((S)-3-(4-amino-3-(4-(2,3-difluorophenyl)-1H-pyrazolo[3,4-d]pyrimidin-1-yl)piperidine-1-carbonyl)-3-(pyrrolidin-2-yl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-morpholinopent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-morpholinopent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((diethylamino)methyl)-cyclopentyl)acrylonitrile;

(S)-2-(3-(4-amino-3-(4-(2,3-di fluorophenoxy)-2-fluorophenyl)-1H-pyrazolo[3,4-d]pyrimidin-1-yl)piperidine-1-carbonyl)-3-(1-((diethylamino)methyl)-cyclopentyl)acrylonitrile;

(R)-2-(3-(4-amino-3-(4-(2,3-difluorophenyl)-1H-pyrazolo[3,4-d]pyrimidin-1-yl)piperidine-1-carbonyl)-3-(1-((dimethylamino)-methyl)cyclopentyl)-acrylonitrile;

(S)-2-(3-(4-amino-3-(4-(2,3-difluorophenyl)-1H-pyrazolo[3,4-d]pyrimidin-1-yl)piperidine-1-carbonyl)-3-(1-((dimethylamino)-methyl)cyclopentyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-methyl piperidin-4-yl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-methylpiperidin-4-yl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(tetrahydro-2H-pyran-4-yl)acrylonitrile;
(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(tetrahydro-2H-pyran-4-yl)acrylonitrile;
(R)-2-(3-(4-amino-3-(4-(2, 3-difluorophenoxy)-2-fluorophenyl)-1H-pyrazolo[3,4-d]pyrimidin-1-yl)piperidine-1-carbonyl)-3-(piperidin-4-yl)acrylonitrile;
(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(piperidin-4-yl)acrylonitrile;
2-((R)-3-(4-amino-3-(4-(2,3-difluorophenoxy)-2-fluorophenyl)-1H-pyrazolo[3,4-d]pyrimidin-1-yl)piperidine-1-carbonyl)-3-(piperidin-3-yl)acrylonitrile;
2-((S)-3-(4-amino-3-(4-(2,3-difluorophenoxy)-2-fluorophenyl)-1H-pyrazolo[3,4-d]pyrimidin-1-yl)piperidine-1-carbonyl)-3-(piperidin-3-yl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;
(R)-2-(2-((4-amino-5-(2-fluoro-4-phenoxyphenyl)-7H-pyrrolo[2,3-d]pyrimidin-7-yl)methyl)pyrrolidine-1-carbonyl)-4-(dimethylamino)-4-methylpent-2-enenitrile;
(S)-2-(2-((4-amino-5-(2-fluoro-4-phenoxyphenyl)-7H-pyrrolo[2,3-d]pyrimidin-7-yl)methyl)pyrrolidine-1-carbonyl)-4-(dimethylamino)-4-methylpent-2-enenitrile;
(R)-2-(2-((4-amino-5-(4-(2,3-difluorophenoxy)phenyl)-7H-pyrrolo[2,3-d]pyrimidin-7-yl)methyl)pyrrolidine-1-carbonyl)-3-cyclopropylacrylonitrile;
(S)-2-(2-((4-amino-5-(4-(2,3-difluorophenoxy)phenyl)-7H-pyrrolo[2,3-d]pyrimidin-7-yl)methyl)pyrrolidine-1-carbonyl)-3-cyclopropylacrylonitrile;
(R)-2-(2-((4-amino-5-(4-(2,3-difluorophenoxy)phenyl)-7H-pyrrolo[2,3-d]pyrimidin-7-yl)methyl)pyrrolidine-1-carbonyl)-4-methylpent-2-enenitrile;
(S)-2-(2-((4-amino-5-(4-(2,3-difluorophenoxy)phenyl)-7H-pyrrolo[2,3-d]pyrimidin-7-yl)methyl)pyrrolidine-1-carbonyl)-4-methylpent-2-enenitrile;
(R)-2-(2-((4-amino-5-(4-(2,3-difluorophenoxy)phenyl)-7H-pyrrolo[2,3-d]pyrimidin-7-yl)methyl)pyrrolidine-1-carbonyl)-4,4-dimethylpent-2-enenitrile;
(S)-2-(2-((4-amino-5-(4-(2,3-difluorophenoxy)phenyl)-7H-pyrrolo[2,3-d]pyrimidin-7-yl)methyl)pyrrolidine-1-carbonyl)-4,4-dimethylpent-2-enenitrile;
(R)-2-(2-((4-amino-5-(4-(2,3-difluorophenoxy)phenyl)-7H-pyrrolo[2,3-d]pyrimidin-7-yl)methyl)pyrrolidine-1-carbonyl)-4-(dimethylamino)-4-methylpent-2-enenitrile;
(S)-2-(2-((4-amino-5-(4-(2,3-difluorophenoxy)phenyl)-7H-pyrrolo[2,3-d]pyrimidin-7-yl)methyl)pyrrolidine-1-carbonyl)-4-(dimethylamino)-4-methylpent-2-enenitrile;
(R)-4-amino-2-(2-((4-amino-5-(2-fluoro-4-phenoxyphenyl)-7H-pyrrolo[2,3-d]pyrimidin-7-yl)methyl)pyrrolidine-1-carbonyl)-4-methylpent-2-enenitrile;
(S)-4-amino-2-(2-((4-amino-5-(2-fluoro-4-phenoxyphenyl)-7H-pyrrolo[2,3-d]pyrimidin-7-yl)methyl)pyrrolidine-1-carbonyl)-4-methylpent-2-enenitrile;
(R)—N-(1-(4-amino-3-(2-fluoro-4-phenoxyphenyl)-1H-pyrazolo[3,4-d]pyrimidin-1-yl) propan-2-yl)-2-cyano-4,4-dimethylpent-2-enamide;
(S)—N-(1-(4-amino-3-(2-fluoro-4-phenoxyphenyl)-1H-pyrazolo[3,4-d]pyrimidin-1-yl)propan-2-yl)-2-cyano-4,4-dimethylpent-2-enamide;
(R)—N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;
(S)—N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;
(R)—N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide;
(S)—N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide;
(R)—N-(1-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide;
(S)—N-(1-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide;
2-((R)-2-((4-amino-3-(2-fluoro-4-phenoxyphenyl)-1H-pyrazolo[3,4-d]pyrimidin-1-yl)methyl)pyrrolidine-1-carbonyl)-3-((S)-pyrrolidin-2-yl)acrylonitrile;
2-((R)-2-((4-amino-3-(2-fluoro-4-phenoxyphenyl)-1H-pyrazolo[3,4-d]pyrimidin-1-yl)methyl)pyrrolidine-1-carbonyl)-3-((R)-pyrrolidin-2-yl)acrylonitrile;
(R)-4-amino-N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;
(S)-4-amino-N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;
(S)—N-(1-(4-amino-3-(2-fluoro-4-phenoxyphenyl)-1H-pyrazolo[3,4-d]pyrimidin-1-yl)propan-2-yl)-2-cyano-4,4-dimethylpent-2-enamide;
(S)—N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;
(S)—N-(1-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide;
(S)—N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide;
(S)-4-amino-N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;
(S)—N-(1-(4-amino-3-(2-fluoro-4-phenoxyphenyl)-1H-pyrazolo[3,4-d]pyrimidin-1-yl)propan-2-yl)-2-cyano-3-cyclopropylacrylamide;
2-[(2R)-2-[[4-amino-3-(2-fluoro-4-phenoxy-phenyl)pyrazolo[3,4-d]pyrimidin-1-yl]methyl]-pyrrolidine-1-carbonyl]-3-(3-methyloxetan-3-yl)prop-2-enenitrile; or 2-[(2S)-2-[[4-amino-3-(2-fluoro-4-phenoxy-phenyl)pyrazolo[3,4-d]pyrimidin-1-yl]methyl]-pyrrolidine-1-carbonyl]-3-(3-methyloxetan-3-yl)prop-2-enenitrile;
or a mixture of R and S isomers thereof;
or an individual (E) or (Z) isomer thereof;
and/or a pharmaceutically acceptable salt of any of the foregoing compounds.

5. The method of claim 4 wherein the BTK inhibitor is:
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;
or a mixture of R and S isomers thereof;
or an individual (E) or (Z) isomer thereof;
and/or a pharmaceutically acceptable salt of any of the foregoing compounds.

6. The method of claim 2 wherein $R^b$ is cyano.

7. The method of claim 1 wherein $R^b$ is hydrogen.

8. The method of claim 2 wherein $R^b$ is hydrogen.

9. A method of treating dry eye disease in a patient in need of such treatment comprising topically administering to the eye of said patient a therapeutically effective amount of a BTK inhibitor, wherein the BTK inhibitor is:
(R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;
or a mixture of R and S isomers thereof;
or an individual (E) or (Z) isomer thereof;
and/or a pharmaceutically acceptable salt of any of the foregoing compounds.

* * * * *

UNITED STATES PATENT AND TRADEMARK OFFICE
CERTIFICATE OF CORRECTION

PATENT NO. : 9,572,811 B2
APPLICATION NO. : 14/418484
DATED : February 21, 2017
INVENTOR(S) : Martin Babler and Mary E. Gerritsen It is certified that error appears in the above-identified patent and that said Letters Patent is hereby corrected as shown below:

In the Claims

Claim 4, Column 122, Lines 4-5, "(R)-2-(2-((4-amino 3-(4-(2,6-difluorophenyl)-1H-pyrazolo" should read -- (R)-2-(2-((4-amino 3-(4-(2,6-difluorophenoxy)-2-fluorophenyl)-1H-pyrazolo --.

Claim 4, Column 124, Lines 26-28, "(S)-2-(2-((4-amino 3-(4-(2,3-difluorophenyl)-1H-pyrazolo" should read -- (S)-2-(2-((4-amino 3-(4-(2,3-difluorophenoxy)-2-fluorophenyl)-1H-pyrazolo --.

Claim 4, Column 125, Lines 30-31, "(S)-2-(2((4-amino 3-(4-(2,3-difluorophenyl)-1H-pyrazolo" should read -- (S)-2-(2-((4-amino 3-(4-(2,3-difluorophenoxy)-2-fluorophenyl)-1H-pyrazolo --.

Claim 4, Column 125, Lines 46-47, "(S)-2-(2-((4-amino 3-(4-(2,3-difluorophenyl)-1H-pyrazolo" should read -- (S)-2-(2-((4-amino 3-(4-(2,3-difluorophenoxy)-2-fluorophenyl)-1H-pyrazolo --.

Claim 4, Column 125, Lines 61-62, "(S)-2-(2-((4-amino 3-(4-(2,3-difluorophenyl)-1H-pyrazolo" should read -- (S)-2-(2-((4-amino 3-(4-(2,3-difluorophenoxy)-2-fluorophenyl)-1H-pyrazolo --.

Claim 4, Column 126, Lines 5-6, "2-((R)-2-((4-amino-3-(4-(2,3-difluorophenyl)-1H-pyrazolo" should read -- 2-((R)-2-((4-amino-3-(4-(2,3-difluorophenoxy)-2-fluorophenyl)-1H-pyrazolo --.

Claim 4, Column 126, Lines 12-13, "(R)-2-(2-((4-amino 3-(4-(2,3-difluorophenyl)-1H-pyrazolo" should read -- (R)-2-(2-((4-amino 3-(4-(2,3-difluorophenoxy)-2-fluorophenyl)-1H-pyrazolo --.

Signed and Sealed this
Fifteenth Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,572,811 B2

Claim 4, Column 126, Lines 16-17, "(S)-2-(2-((4-amino 3-(4-(2,3-difluorophenyl)-1H-pyrazolo" should read -- (S)-2-(2-((4-amino 3-(4-(2,3-difluorophenoxy)-2-fluorophenyl)-1H-pyrazolo --.

Claim 4, Column 126, Lines 28-29, "(R)-2-(2-((4-amino 3-(4-(2,3-difluorophenyl)-1H-pyrazolo" should read -- (R)-2-(2-((4-amino 3-(4-(2,3-difluorophenoxy)-2-fluorophenyl)-1H-pyrazolo --.

Claim 4, Column 126, Lines 40-41, "(S)-2-(2-((4-amino 3-(4-(2,3-difluorophenyl)-1H-pyrazolo" should read -- (S)-2-(2-((4-amino 3-(4-(2,3-difluorophenoxy)-2-fluorophenyl)-1H-pyrazolo --.

Claim 4, Column 128, Lines 62-63, "(R)-2-(3-4-amino-3-(4-(2,3-difluorophenyl)-1H-parazolo" should read -- (R)-2-(3-4-amino-3-(4-2,3-difluorophenoxy)-2-fluorophenyl)-1H-parazolo --.

Claim 4, Column 129, Lines 27-28, "-2-frophenyl)" should read -- -2 fluorophenyl --.

Claim 4, Column 130, Lines 54-55, "(R)-2-(3-4-amino-3-(4-(2,3-difluorophenyl)-1H-parazolo" should read -- (R)-2-(3-4-amino-3-(4-2,3-difluorophenoxy)-2-fluorophenyl)-1H-parazolo --.

Claim 4, Column 130, Lines 58-59, "(S) -2-(3-(4-amino-3-(4-(2,3-difluorophenyl)-1H-pyrazolo" should read -- (S) -2-(3-(4-amino-3-(4-(2,3-difluorophenoxy)-2-fluorophenyl)-1H-pyrazolo --.

Claim 4, Column 130, Line 64, "(1-methyl piperidin-4-yl)" should read -- (1-methylpiperidin-4-yl) --.